(12) United States Patent
Stone et al.

(10) Patent No.: US 11,904,029 B2
(45) Date of Patent: Feb. 20, 2024

(54) PARTICLES FUNCTIONALIZED WITH IMAGEABLE RADIOISOTOPES AND METHODS OF MAKING AND USE THEREOF

(71) Applicants: University of Virginia Patent Foundation, Charlottesville, VA (US); Boston Scientific Medical Device Limited, Galway (IE)

(72) Inventors: James Radford Stone, Charlottesville, VA (US); Kiel Douglas Neumann, Charlottesville, VA (US); Matthew Robert Dreher, Rockville, MD (US)

(73) Assignees: Boston Scientific Medical Device Limited, Galway (IE); University of Virginia Patent Foundation, Charlottesville, VA (US)

( * ) Notice: Subject to any disclaimer, the term of this patent is extended or adjusted under 35 U.S.C. 154(b) by 53 days.

(21) Appl. No.: 17/166,820

(22) Filed: Feb. 3, 2021

(65) Prior Publication Data
US 2021/0236669 A1 Aug. 5, 2021

Related U.S. Application Data

(60) Provisional application No. 62/970,587, filed on Feb. 5, 2020.

(51) Int. Cl.
*A61K 51/12* (2006.01)
*A61N 5/10* (2006.01)
(Continued)

(52) U.S. Cl.
CPC .......... *A61K 51/1244* (2013.01); *A61B 6/037* (2013.01); *A61K 51/02* (2013.01);
(Continued)

(58) Field of Classification Search
CPC .... A61N 5/10–1084; A61N 2005/1085–1098; A61K 51/1244; A61K 51/1251
See application file for complete search history.

(56) References Cited

U.S. PATENT DOCUMENTS

| | | | | |
|---|---|---|---|---|
| 2006/0177373 A1* | 8/2006 | Ruys | .......... | A61P 1/16 424/1.11 |
| 2015/0118495 A1* | 4/2015 | Day | .......... | C01B 25/32 424/1.61 |

(Continued)

OTHER PUBLICATIONS

Chen et al., "In Vivo Integrity and Biological Fate of Chelator-Free Zirconium-89-Labeled Mesoporous Silica Nanoparticles," ACS Nano 2015, vol. 9 No. 8, p. 7950-7959 (Year: 2015).*

*Primary Examiner* — Thaddeus B Cox
(74) *Attorney, Agent, or Firm* — Seager, Tufte & Wickhem, LLP

(57) ABSTRACT

Some embodiments relate to imageable radioisotopic microspheres. In some embodiments, the imageable microspheres are radiolabeled with imageable radioisotopes. In some embodiments, the imageable radioisotope is directly coupled to a surface of a substrate of the microsphere. In some embodiments, the imageable microspheres can be used as surrogate particles to predict the distribution of therapeutic microspheres comprising radiotherapeutic isotopes.

20 Claims, 9 Drawing Sheets

(51) Int. Cl.
*A61K 51/02* (2006.01)
*A61B 6/03* (2006.01)
(52) U.S. Cl.
CPC .... *A61N 5/1001* (2013.01); *A61N 2005/1021* (2013.01); *A61N 2005/1052* (2013.01)

(56) References Cited

U.S. PATENT DOCUMENTS

2017/0143857 A1* 5/2017 Day .................... A61B 6/4057
2022/0177351 A1* 6/2022 Legere ................ A61N 5/1014

* cited by examiner

FIG. 1

| Lung Shunt and Volumes | | | | | |
|---|---|---|---|---|---|
| Stat | PT 1 | | | PT 2 | |
| Lung Shunt = | 3.1 | % | | 3.1 | % |
| Lungs Counts = | 1179.8 | kCNTS | | 13902.5 | kCNTS |
| Whole Liver Counts = | 36305.2 | kCNTS | | 435053.2 | kCNTS |
| Normal Liver Counts = | 31987.6 | kCNTS | | 383129.2 | kCNTS |
| Tumor Counts = | 4348 | kCNTS | | 52290.6 | kCNTS |
| Lungs Volume = | 30.6 | CC | | 30.6 | CC |
| Whole Liver Volume = | 54.7 | CC | | 54.7 | CC |
| Normal Liver Volume = | 44.2 | CC | | 44.2 | CC |
| Tumor Volume = | 10.6 | CC | | 10.6 | CC |

FIG. 7A–7B

PARTICLES FUNCTIONALIZED WITH IMAGEABLE RADIOISOTOPES AND METHODS OF MAKING AND USE THEREOF

CROSS REFERENCE TO RELATED APPLICATIONS

The present application claims the benefit of priority to U.S. Provisional Patent Application No. 62/970,587, filed Feb. 5, 2020, the entirety of which is hereby incorporated by reference herein.

FIELD

The present disclosure pertains to particles functionalized with imageable radioisotopes, their use as surrogates for therapeutic particles, methods of making such imageable particles, and methods of using the particles for biological imaging and dosimetry.

BACKGROUND

Description of the Related Art

One approach to the treatment of patients with certain cancers is to introduce radioactive isotopes into the patient's circulatory system. A measured amount of radioactive isotopes are injected into the patient such that they accumulate at the site of the cancer sufficiently to treat the cancer.

SUMMARY

In one method for the radio-treatment of cancer, radioactive microspheres are delivered to a point in the vasculature of a patient such that they will be carried by blood flow into a tissue of interest. Once at the tissue of interest, they lodge in the capillaries and deliver a dose of therapeutic radiation. This treatment has been termed selective internal radiation therapy (SIRT). The goal is to have a sufficient dose of radiation to cause localised tissue death of cancerous tissues.

However, because therapeutic microparticles are not readily imageable, their distribution in the body is difficult to determine. The properties of these therapeutic microspheres make them difficult and impractical to predict distributions of therapeutic doses within the body. In turn, it is difficult to track and accurately assess where therapeutic microspheres have ultimately lodged. Without the ability to accurately determine where the microparticles reside in the body, the dose of radiation at a target location for therapeutic microspheres is difficult to predict or measure. Moreover, the dose of harmful radiation to healthy areas of the body is also difficult to determine. Some embodiments disclosed herein pertain to particles (e.g., microspheres) decorated with imageable radioactive isotopes that are viewable using an imaging modality. In some embodiments, when introduced to the body, these imageable radioisotopic particles can be used as surrogates to approximate the distribution of therapeutic microspheres in the body. In some embodiments, the use of imageable surrogates as disclosed herein can allow more accurate prediction of radiation dosing, more effective treatment, and/or lower incidences of side effects for patients.

As disclosed elsewhere herein, some embodiments pertain to an imageable particle. In some embodiments, the particle is a microsphere. In some embodiments, the imageable microsphere comprises at least one imageable radioisotope. In some embodiments, the imageable microsphere also comprises a substrate. In some embodiments, the substrate provides a surface onto which the at least one imageable radioisotope can be bound. In some embodiments, the substrate comprises an inorganic material. In some embodiments, the inorganic material comprises metalloid or metal atoms. In some embodiments, the substrate comprises a core extending to a surface of the particle. In some embodiments, the core comprises a first portion of metalloid or metal atoms and the surface comprises a second portion of metalloid or metal atoms. In some embodiments, the second portion of the metalloid or metal atoms are bonded to non-metal atoms. In some embodiments, the imageable radioisotope is bound directly to the substrate through at least a portion of the non-metal atoms at the surface of the substrate. In some embodiments, the first portion of metalloid or metal atoms are also bonded to non-metal atoms.

In some embodiments, the substrate comprises a substantially homogeneous mixture of constituent elements (i.e., elements from the periodic table). In some embodiments, the surface comprises at least a portion of the constituent elements. For example, in some embodiments, the metalloid, metal, or non-metal atoms at the surface of the substrate comprise the same elements as those metalloid, metal, or non-metal atoms found in the core.

In some embodiments, the non-metal atoms are oxygen atoms. In some embodiments, at least a portion of the oxygen atoms at the surface of the substrate are provided as hydroxyl groups.

Some embodiments pertain to an imageable microsphere comprising an inorganic substrate with a surface layer. In some embodiments, the imageable microsphere comprises at least one imageable radioisotope. In some embodiments, the inorganic substrate comprises at least one non-metal, a metalloid, or a transition metal oxide. In some embodiments, the imageable radioisotope is bound to the surface of the inorganic substrate by a Lewis acid-base coordination bond (so as to provide a Lewis acid-base adduct) e.g., to an inorganic Lewis base.

Some embodiments disclosed herein pertain to an imageable microsphere comprising an inorganic substrate comprising a surface having one or more electron donating functionalities. In some embodiments, the imageable microsphere comprises a surface layer comprising at least one imageable radioisotope. In some embodiments, the imageable radioisotope is bound to the surface of the inorganic substrate during preparation of the imageable microsphere via coupling with the one or more electron donating functionalities.

Some embodiments pertain to an imageable microsphere, comprising a ceramic microsphere substrate and at least one imageable radioisotope. The imageable radioisotope is coupled to the surface of the ceramic microsphere substrate, for example, as a Lewis acid-base adduct (e.g., of an inorganic Lewis base).

Any of the embodiments described above, or described elsewhere herein, can include one or more of the following features.

In some embodiments, the imageable radioisotope is bound to the substrate via a chemical bond. In some embodiments, the chemical bond is selected from an ionic bond, a covalent bond, or a coordinate bond. In some embodiments, the chemical bond is a coordinate bond.

In some embodiments, the imageable isotope is configured for imaging by an imaging modality selected from single photon imaging and double photon imaging. In some embodiments, the imageable radioisotope is configured for imaging by an imaging modality selected from positron emission tomography (PET), single photon emission computed tomography (SPECT), and gamma camera imaging. In some embodiments, the imageable radioisotope is a positron emitter or a gamma emitter. In some embodiments, the at least one imageable radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, and/or combinations thereof. In some embodiments, the at least one imageable radioisotope is a metallic radioisotope. In some embodiments, the at least one imageable radioisotope is selected from $^{99m}$Tc and $^{89}$Zr. In some embodiments, the at least one imageable radioisotope is $^{89}$Zr. In some embodiments, the at least one imageable radioisotope is $^{99m}$Tc.

In some embodiments, a surface of the imageable microsphere comprises a structure of Formula (V):

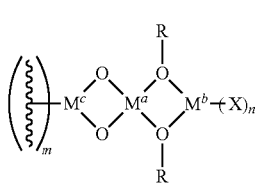

(V)

where the substrate comprises $M^c$ and where $M^c$ is independently selected from Pb, Al, Si, Y, Mn, Ga, Fe, Sr, and Ti; m is an integer selected from 1, 2, or 3; $M^a$ is either an atom of the substrate or a bridging atom and $M^a$ is selected from Pb, Al, Si, Y, Mn, Ga, Fe, Ti, Sr and Sn; $M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof; each instance of R is either not present or is H; X is selected from —OH, =O, and —O$^-$; and n is an integer selected from 0, 1, 2, 3, or 4. $M^a$ may either be an atom of the substrate or a bridging metal atom that chemically connects (through chemical bonds) the imageable radioisotope to the substrate. In some embodiments, where $M^a$ is an atom of the substrate, $M^a$ is selected from Pb, Al, Si, Y, Mn, Ga, Fe, Sr, and Ti. In some embodiments, where $M^a$ is an atom of the substrate, $M^a$ is selected from Pb, Al, Si, Y, Mn, Ga, Fe, and Ti. In some embodiments, $M^a$ is a Sn bridging metal atom. In some embodiments, $M^a$ is Al; the substrate comprises $M^a$ and $M^a$ is Si; $M^b$ is $^{89}$Zr; each X is independently —OH or =O; and n is 1 or 2. In some embodiments, $M^c$ and $M^a$ are independently selected from Al, Si, and Y; $M^b$ is $^{89}$Zr; each X is independently —OH or =O; and n is 1 or 2. In some embodiments, $M^b$ is $^{89}$Zr, X is —OH, and n is 2. In some embodiments, $M^c$ is Si, Al, or Y; $M^a$ is Sn; $M^b$ is $^{99m}$Tc; each X is independently —OH or =O; and n is 2 or 3. In some embodiments, $M^b$ is $^{99m}$Tc, X is —OH, and n is 2 or 3.

In some embodiments, a surface of the imageable microsphere comprises a structure of Formula (VI):

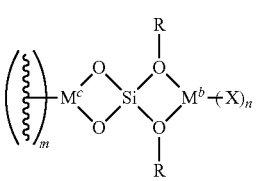

(VI)

where the substrate comprises $M^c$ and $M^c$ is selected from Pb, Al, Si, Y, Mn, Ga, Fe, Sr and Ti; the surface layer comprises $M^b$ and $M^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^4$Sc, $^{51}$Cr, Al$^{18}$F, $^{177}$Lu, and/or combinations thereof; each instance of R is not present or is —H; each instance of X is independently selected from is selected from —OH, =O, and —O$^-$; m is an integer selected from 1, 2, or 3; and n is an integer selected from 0, 1, 2, 3, or 4. In some embodiments, m is 1. In some embodiments, $M^c$ is Al; $M^b$ is $^{89}$Zr; X is —OH or O$^-$; and n is 1 or 2. In some embodiments, $M^c$ is Y or Al; $M^b$ is $^{89}$Zr; X is —OH or O$^-$; and n is 2. In some embodiments, $M^c$ is Y or Al; $M^b$ is $^{89}$Zr; X is —OH or O$^-$; and n is 1 or 2. In some embodiments, $M^b$ is AlF$^{18}$. In some embodiments, $M^b$ is $^{99m}$Tc. In some embodiments, $M^b$ is $^{89}$Zr. In some embodiments, X is OH.

In some embodiments, a surface layer of the imageable microsphere comprises a structure of Formula (VIII):

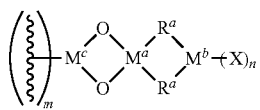

(VIII)

where the substrate comprises $M^a$ and $M^c$ and where $M^a$ and $M^c$ are independently selected from Pb, Al, Si, Y, Mn, Ga, Fe, Sr, and Ti; m is an integer selected from 1, 2, or 3; $M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof; each instance of $R^a$ is independently OH, O, or —O—Sn—O—; X is selected from —OH, =O, and —O$^-$; and n is an integer selected from 0, 1, 2, 3, or 4. In several embodiments, $M^a$ and $M^c$ are independently selected from Sn, Pb, Al, Si, Y, Mn, Ga, Fe, Sr, and Ti; m is an integer selected from 1, 2, or 3; $M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof; each instance of $R^a$ is independently OH or O; X is selected from —OH, =O, and —O$^-$; and n is an integer selected from 0, 1, 2, 3, or 4. In some embodiments, $M^c$ is independently selected from Sn, Pb, Al, Si, Y, Mn, Ga, Fe, Sr, and Ti and particularly from Al, Si, Y, Mn and Sr; $M^a$ is Sn; $R^a$ is O; $M^b$ is $^{99m}$Tc X is OH, —O—, or =O and n is 2 or 3.

In some embodiments, the Sn in —O—Sn—O— could have one or more OH, O—or a hydrate groups coordinated to it. In some embodiments, $M^c$ and $M^a$ are independently Si, Al, or Y; $M^b$ is $^{99m}$Tc; each X is independently —OH, =O, or —O$^-$; and n is 2 or 3. In some embodiments, $M^c$ and $M^a$ are independently Si, Al, or Y; $M^b$ is $^{99m}$Tc; at least an instance of $R^a$ is —O—Sn—O—; each X is independently —OH, =O, or —O$^-$; and n is 2 or 3. In some embodiments, $M^c$ is Al; $M^a$ is Si; $M^b$ is $^{99m}$Tc; each X is independently —OH or =O; and n is 2 or 3. In some embodiments, $M^c$ is Al; $M^a$ is Si; $M^b$ is $^{99m}$Tc; at least an instance of $R^a$ is —O—Sn—O—, each X is independently —OH or =O; and n is 2 or 3. In some embodiments, $M^b$ is $^{99m}$Tc; at least an instance of $R^a$ is —O—Sn—O—; each X is independently —OH or =O; and n is 2 or 3. In some embodiments, $M^b$ is $^{99m}$Tc; an instance of $R^a$ is —O—Sn—O—, an instance of $R^a$ is —O— or —OH—; each X is independently —OH or =O; and n is 2 or 3.

In some embodiments, as disclosed elsewhere herein, the inorganic substrate may comprise or be a ceramic material. In some embodiments the ceramic material may comprise or be a glass.

The inorganic substrate, ceramic or glass may comprise at least one non-metal, a metalloid, or transition metal oxide. In some embodiments, the ceramic material or glass may comprise at least one element selected from yttrium, silicon, manganese, aluminium, gallium, strontium, and titanium. In some embodiments, the inorganic substrate, ceramic or glass comprises silicon dioxide and at least one other element selected from yttrium, manganese, aluminium, gallium, boron, strontium, and titanium. In some embodiments, the inorganic substrate, ceramic or glass comprises at least one of $Y_2O_3$, $SiO_2$, $MnO_2$, $AlO_3$, $Ga_2O_3$, $Fe_2O_3$, $TiO_2$, $SrO_2$, $SrCO_3$, or combinations thereof. In some embodiments, the inorganic substrate, ceramic or glass may comprise $SiO_2$ and at least one of $Y_2O_3$, $MnO_2$, $AlO_3$, $Ga_2O_3$, $Fe_2O_3$, $TiO_2$, $SrO_2$, $SrCO_3$, or combinations thereof.

The inorganic substrate, ceramic or glass may comprise or be an yttrium aluminum silicon oxide. Yttrium aluminum silicon oxide are described, for example, in U.S. Pat. No. 4,789,501, which is hereby incorporated by reference in its entirety.

In some embodiments, the imageable microsphere lacks a therapeutic radioisotope.

In some embodiments, the imageable microsphere has a diameter of between 5 μm and 1000 μm. In some embodiments, the diameter is a mean diameter of a population of imageable microspheres. In some embodiments, the diameter is measured by light or electron microscopy.

In some embodiments, the inorganic substrate is non porous. In some embodiments, the inorganic substrate is porous. In some embodiments, the imageable element is confined to the surface of the microsphere and/or the core of the inorganic substrate lacks the imageable radioisotope. In some embodiments, the imageable element is confined to the surface of the non porous microsphere.

Some embodiments pertain to an imageable microsphere made by a method comprising providing the substrate and chemically coupling the at least one imageable radioisotope to the substrate to provide the imageable microsphere.

Some embodiments pertain to an imageable microsphere made by a method comprising providing a substrate comprising an inorganic material as described elsewhere herein (e.g., metalloid or metal atoms bonded that may or may not also be bonded to non-metal atoms). In some embodiments, the substrate comprises a core comprising a first portion of the metalloid or metal atoms and a surface layer comprising a second portion of the metalloid or metal atoms. In some embodiments, at least one imageable radioisotope is provided. In some embodiments, the at least one imageable radioisotope is chemically coupled to the surface layer of the substrate to provide the imageable microsphere. In some embodiments, the chemical coupling is through non-metal atoms at the surface of the inorganic material.

In some embodiments, the at least one imageable radioisotope is provided as a salt prior to chemically coupling the at least one imageable radioisotope to the surface layer of the inorganic substrate. In some embodiments the salt may be water soluble or substantially water soluble. In some embodiments, the salt is a halogen salt (such as a fluoride, chloride, bromide, or iodide salt), and/or a polyatomic salt. or may be a salt with an organic acid (such as an oxalate).

In some embodiments, the chemical functionalization is carried out in the presence of a reducing agent. In some embodiments, the reducing agent is selected from one or more of a tin salt (e.g., a stannous salt such as stannous chloride, in order to provide stannous ions), a tin hydrate (e.g., stannous hydrate), HCl, sodium borohydride, sodium diothionite, ferrous sulfate, ferric chloride plus ascorbic acid, hypophosphorous acid (e.g., phosphinic acid), and/or hydrazine. In some embodiments, the reducing agent is a tin salt (e.g., a stannous salt such as stannous chloride, in order to provide stannous ions) or a tin hydrate (e.g., stannous hydrate).

Some embodiments pertain to a process for the preparation of an imageable ceramic microsphere comprising reacting a ceramic microsphere comprising at least one non-metal, metalloid, or transition metal oxide with $^{99m}$Tc pertechnetate ions in the presence of a reducing agent.

Some embodiments pertain to a process for the preparation of an imageable ceramic microsphere comprising reacting a ceramic microsphere comprising at least one non-metal or transition metal oxide with $^{89}$Zr ions, for example as $^{89}$Zr oxalate or $^{89}$Zr chloride. In some embodiments the reaction is carried out in the presence of a base. Where the $^{89}$Zr is provided as a halide salt, such as the chloride, it is typically provided in acidic solution (e.g. in 1M HCl or 1M oxalic acid), in this case, the acid may be neutralised with a base and the reaction therefore may proceed in presence of a base.

Some embodiments pertain to a method of making the imageable microsphere comprising providing the inorganic substrate and chemically functionalizing the inorganic substrate with the at least one imageable radioisotope to provide the imageable microsphere.

In some embodiments, the at least one imageable radioisotope is provided in an ionic form, for example, as a salt prior to chemically functionalizing the at least one imageable radioisotope to a surface of the inorganic substrate. In some embodiments the salt may be water soluble or substantially water soluble. In some embodiments, the salt is an alkali metal (such as sodium or potassium) salt, an alkali earth metal (such as calcium magnesium barium or strontium) salt, a halogen salt (such as a chloride), and/or a polyatomic salt. or may be a salt with an organic acid, such as an oxalate. In some embodiments, the salt is a halogen salt (such as a chloride), and/or a polyatomic salt, or may be a salt with an organic acid, such as an oxalate. In some embodiments, one or more counter ions (e.g., 1, 2, 3, 4, 5, etc.) can be associated with the imageable radioisotope. In some embodiments, the at least one imageable radioisotope is provided in combination with a chelator. In some embodiments, the chelator is selected from one or more of 6-hydrazinonicotinyl (HYNIC), dodecane tetraacetic acid (DOTA), deferoxamine (DFO), or the like.

In some embodiments, a reducing agent is added during the chemical functionalization step, such as when the imageable isotope is $^{99m}$Tc. In some embodiments, the reducing agent is selected from one or more of a tin salt (e.g., a stannous salt such as stannous chloride, in order to provide stannous ions), a tin hydrate (e.g., stannous hydrate), HCl, sodium borohydride, sodium diothionite, ferrous sulfate, ferric chloride plus ascorbic acid, hypophosphorous acid, and/or hydrazine. In some embodiments the radioisotope is $^{99m}$Tc and the reaction is carried out in the presence of a tin salt (e.g., a stannous salt such as stannous chloride, in order to provide stannous ions). In some embodiments the $^{99m}$Tc is provided in the form of a pertechnetate ion.

Some embodiments pertain to a method for preparing an imageable microsphere as described elsewhere herein, the method comprising providing a microsphere comprising a ceramic microsphere substrate, as described elsewhere herein, and reacting the microsphere with an imageable radioisotope, as described elsewhere herein, under conditions suitable to couple the imageable radioisotope to the surface of the ceramic microsphere substrate in the form of a Lewis acid-base adduct.

In some embodiments, the radioisotope is provided in the form of a salt. In some embodiments, the radioisotope is provided in ionic form such as in the form of a salt. In some embodiments, the salt may be water soluble or substantially water soluble. In some embodiments, the salt is an alkali metal (such as sodium or potassium) salt, an alkali earth metal (such as calcium magnesium barium or strontium) salt, a halogen salt (such as a chloride), and/or a polyatomic salt. or may be a salt with an organic acid, such as an oxalate.

In some embodiments, such as where $^{89}$Zr is the imageable isotope, the radioisotope may be provided in the form of a salt. The radioisotope may be reacted with the microsphere in the presence of a base. The base may be, for example, selected from alkali or alkali earth metal carbonates (such as sodium carbonate and calcium carbonate), alkali hydroxides, or the like. In some embodiments, the base may be selected from NaOH, KOH, or the like. In some embodiments, the base is a weak base. In some embodiments, the base is a weak base whose conjugate acid has a pKa equal to or greater than about: 3, 5, 7, 9, 11, 13, 14, or ranges including and/or spanning the aforementioned values. In some embodiments, the base is an inorganic base. In some embodiments the imageable radioisotope may be $^{89}$Zr, for example provided as salt, such as $^{89}$Zirconium oxalate or a halide salt such as $^{89}$Zirconium chloride.

In some embodiments, the radioisotope is provided in the form of a salt and is reacted with the ceramic microsphere in the presence of a reducing agent. In some embodiments the reducing agent is selected from one or more of tin salt (e.g a stannous salt such as stannous chloride), a tin hydrate (e.g., stannous hydrate), HCl, sodium borohydride, sodium diothionite, ferrous sulfate, ferric chloride plus ascorbic acid, hypophosphorous acid, and/or hydrazine. In one approach the reducing agent is a tin salt which may be a stannous salt, for example with a halogen such as chlorine.

In one approach the imageable isotope may be $^{99m}$Tc, which may be provided as a pertechnetate salt. The reducing agent may be stannous ions, such as stannous chloride.

In any of the methods described, the method may be carried out in aqueous media and may additionally include recovering the imageable microsphere and/or washing the microsphere to remove unreacted radioisotope. In some embodiments, the method may additionally comprise resuspending the imageable microsphere in a pharmaceutically acceptable injectable aqueous medium. Such as a sterile aqueous medium.

Some embodiments pertain to an imageable microsphere obtainable by any of the preparative methods described herein.

Some embodiments pertain to a method for determining an amount of therapeutic microspheres to provide to the body of a patient. In some embodiments, a population of imageable microspheres is provided. In some embodiments, the population of imageable microspheres is provided to the patient by introducing the population of imageable microspheres to a first position in the vasculature of the patient. In some embodiments, the population of imageable microspheres is allowed to distribute within the body of the patient. In some embodiments, a distribution of at least a portion of the population of the imageable microspheres within the body of the patient is determined by imaging at least a target section of the body of the patient using an imaging modality. In some embodiments, the distribution of the imageable microspheres is used to calculate an amount of therapeutic microspheres to be delivered to the body of the patient. In some embodiments, the target section of the body is a portion of the body having a tumor to be treated.

In some embodiments, the target section of the body is a liver of the patient. In some embodiments, the target section of the body is a brain of the patient. In some embodiments, the target section of the body is a lung of the patient. In some embodiments, the target section of the body is the prostate of the patient. In some embodiments, the target section of the body is a kidney of the patient. In some embodiments, the target section of the body is a spleen of the patient. In some embodiments, the target section of the body is the gastrointestinal tract of the patient. In some embodiments, the target section of the body is the pancreas of the patient. In some embodiments, the target section of the body is the adrenal gland of the patient. In some embodiments, the target section of the body is the gallbladder of the patient. In some embodiments, the target section of the body is the bladder of the patient. In some embodiments, the target section of the body is muscle of the patient. In some embodiments, the target section of the body is bone of the patient. In some embodiments, the target section of the body is the thyroid of the patient. In some embodiments, the target section of the body is an ovary of the patient. In some embodiments, the target section of the body is the uterus of the patient. In some embodiments, the method of treatment includes treating a tumor in any of the aforementioned target sections.

In some embodiments, the imaging modality is SPECT. In some embodiments, the detection modality is PET. In some embodiments, the detection modality is a gamma camera imaging. In some embodiments, the imageable microspheres are the imageable microspheres as disclosed elsewhere herein.

Some embodiments pertain to a method for treating a patient. In some embodiments, a population of imageable microspheres is provided. In some embodiments, the population of imageable microspheres is delivered to the patient by introducing the population of imageable microspheres to a first position in the vasculature of a body of the patient. In some embodiments, the population of imageable microspheres is allowed to distribute within the body of the patient. In some embodiments, a distribution of at least a portion of the population of the imageable microspheres is determined within the body of the patient by imaging at least a target section of the body of the patient using an imaging modality. In some embodiments, the distribution of the imageable microspheres is used to calculate an amount of therapeutic microspheres to be delivered to the body of the patient. In some embodiments, data regarding a distribution of an imageable therapeutic microsphere surrogate in a patient is obtained. In some embodiments, the data is used to determine a dose of a therapeutic amount of microspheres to administer to the body of the patient. In some embodiments, a population of therapeutic microspheres is delivered to the patient by introducing the population of therapeutic microspheres to a second position in the vasculature of the body of the patient. In some embodiments, the population of therapeutic microspheres is allowed to distribute within the body of the patient, thereby treating the patient. In some embodiments, the second position in the vasculature of the patient is the same as the first position in the vasculature of the patient.

In some embodiments, the imaging modality is SPECT. In some embodiments, the detection modality is PET. In some embodiments, the detection modality is a gamma camera imaging. In some embodiments, the imageable microspheres are the imageable microspheres as disclosed herein.

Some embodiments pertain to a method for treating a patient with therapeutic microspheres. In some embodiments, data calculated from the distribution of an imageable therapeutic microsphere surrogate in a patient is obtained. In some embodiments, the data is used to determine an amount of therapeutic microspheres to be dosed to a body of the patient. In some embodiments, the amount of therapeutic microspheres is administered to the patient by introducing the amount of therapeutic microspheres to a first position in the vasculature of the patient. In some embodiments, the therapeutic microspheres are allowed to distribute within the body of the patient. In some embodiments, the therapeutic microspheres are allowed to reside in the body of the patient, thereby treating the patient.

In some embodiments, a population of imageable microspheres is provided to the patient. In some embodiments, the population of imageable microspheres is delivered to the patient by introducing the population of imageable microspheres to the first position in the vasculature of the body of the patient. In some embodiments, the population of imageable microspheres is allowed to distribute within the body of the patient. In some embodiments, a distribution of at least a portion of the population of the imageable microspheres is determined within the body of the patient by imaging at least a target section of the body of the patient using an imaging modality. In some embodiments, the distribution of the imageable microspheres is used to calculate the amount of therapeutic microspheres to be delivered to the body of the patient.

Some embodiments pertain to a method of treating malignant tumors or benign tumors (e.g., non-malignant tumors) in a patient in need of treatment. Some embodiments pertain to a method of treating vascularized tumors having a vascular supply (e.g., malignant or benign tumors), such as those found in liver cancer (e.g., hepatic neoplasias such as hepatocellular carcinoma —HCC, as well as tumors derived from metastasis of other tumors to the liver, such as neuroendocrine tumors and colorectal tumors), as well as those of the brain, prostate, lung, spleen and kidney, for example. In some embodiments, a population of imageable microspheres is introduced to the patient. In some embodiments, the imageable microspheres are allowed to distribute within the patient over a period of time. In some embodiments, the imageable microspheres are imaged directly after injection or in real time (during injection). In some embodiments, the imageable microspheres are allowed to distribute within the patient over a period of time that is less than two half-lives of the imageable radioisotope associated with the imageable microsphere. In some embodiments, the distribution of the imageable microspheres at a cancer site within the patient is determined by imaging the imageable microspheres using an imaging modality. In some embodiments, an estimated effective dose at the cancer site is determined based on the distribution of the imageable microspheres had the imageable microspheres been replaced by therapeutic microspheres. In some embodiments, an amount of the therapeutic microspheres is administered to the patient based on the estimated effective dose (i.e., an estimated absorbed dose). In some embodiments, the population of imageable microspheres comprises the imageable microsphere as disclosed elsewhere herein. In some embodiments, the cancer is a liver cancer.

In some embodiments, after injection the imageable microspheres are imaged. In some embodiments, prior to imaging, the imageable microspheres are allowed to distribute within the patient for a period of at least about: 2 minutes, 5 minutes, 10 minutes, 30 minutes, 1 hour, 4 hours, 6 hours, or ranges including and/or spanning the aforementioned values. In some embodiments, the imageable microspheres distribute in the body soon after injection (e.g., in a matter of minutes). In some embodiments, the imageable microspheres distribute within the patient (e.g., in target and or off-target areas) within a period of equal to or less than about: 2 minutes, 5 minutes, 10 minutes, 30 minutes, or ranges including and/or spanning the aforementioned values. In some embodiments, prior to imaging, the imageable microspheres are allowed to distribute within the patient for a period of equal to or less than about: 2 minutes, 5 minutes, 10 minutes, 30 minutes, or ranges including and/or spanning the aforementioned values.

Some embodiments pertain to a method of predicting the degree of lung shunt (off target delivery) for a patient for radioisotopic cancer treatment. In some embodiments, a population of imageable microspheres is administered to the patient. In some embodiments, the imageable microspheres are allowed to distribute within the patient over a period of time. In some embodiments, the distribution of the imageable microspheres within a lung of the patient is determined by imaging the imageable microspheres using an imaging modality. In some embodiments, an estimated dose of radiation to the lung of the patient is determined by calculating the dose of radiation that would have been received had a specific quantity of radioisotopic therapeutic particles been administered instead of imageable microspheres. In some embodiments, a dose of the radioisotopic therapeutic microspheres that is sufficient to cause clinically relevant pulmonary changes due to lung shunt is determined. In some embodiments, a determination is made as to whether the patient is a candidate that can receive treatment. In some embodiments, a dose of radioisotopic therapeutic microspheres is administered to the patient that is below the dose of the radioisotopic therapeutic microspheres determined to be sufficient to cause clinically relevant pulmonary changes due to lung shunt. In some embodiments, the population of imageable microspheres comprises the imageable microsphere as disclosed elsewhere herein.

Some embodiments pertain to a method of reducing gastrointestinal damage during treatment of a patient in need of radioisotopic cancer treatment. In some embodiments, the method comprises introducing a population of imageable microspheres to the patient. In some embodiments, the imageable microspheres are allowed to distribute within the patient over a period of time. In some embodiments, the distribution of the imageable microspheres within a gastrointestinal tract of the patient is determined by imaging the imageable microspheres using an imaging modality. In some embodiments, an estimated dose of radiation in the gastrointestinal tract of the patient if the imageable microspheres had a specific quantity of been replaced by radioisotopic therapeutic microspheres is determined. In some embodiments, a dose of the radioisotopic therapeutic microspheres that is sufficient to cause gastrointestinal tract damage is determined. In some embodiments, a determination is made as to whether the patient is a candidate that can receive treatment. In some embodiments, a dose of the radioisotopic therapeutic microspheres that is below the dose of the radioisotopic therapeutic microspheres determined to be sufficient to cause damage gastrointestinal tract is administered to the patient. In some embodiments, the population of imageable microspheres comprises the imageable microsphere as disclosed elsewhere herein.

Some embodiments pertain to a kit. In some embodiments, the kit comprises underivatized versions of the imageable microspheres described further herein and instructions to derivatize the microspheres with the imageable radioisotopes described herein. In some embodiments, for example the kit comprises a microsphere comprising a substrate that comprises an inorganic material that comprises metalloid or metal atoms bonded to non-metal atoms, the substrate may comprise a core extending to a surface, the core comprising a first portion of the metalloid or metal atoms bonded to the non-metal atoms and the surface comprising a second portion of the metalloid or metal atoms bonded to the non-metal atoms. The kit may also comprise instructions for reacting an imageable radioisotope with the substrate such as to bind the imageable radioisotope directly to the substrate through at least a portion of the non-metal atoms at the surface of the substrate.

In some embodiments, the kit may comprise a microsphere comprising an inorganic substrate; wherein the inorganic substrate comprises at least one non-metal, a metalloid, or a transition metal oxide. The kit may additionally comprise instructions for binding an imageable radioisotope to the surface of the inorganic substrate through a Lewis acid-base coordination bond.

In some embodiments the kit may comprise a microsphere comprising a ceramic microsphere substrate and instructions for carrying out a reaction in which an imageable radioisotope is coupled to the ceramic microsphere substrate as a Lewis acid base adduct.

In some embodiments the kit may additionally comprise a reducing agent as further described herein, In some embodiments the kit may additionally comprise therapeutic microspheres, which may be for example microspheres suitable for selective internal radiation therapy as described further herein.

In some embodiments, the kit comprises instructions for using a catheter to introduce the imageable microsphere into a patient. In some embodiments, the kit comprises one or more of a vascular access needle, a vascular guidewire, a vascular sheath (e.g., 4-6Fr), a vascular catheter (4-5Fr), a microcatheter, syringes, and a vial.

BRIEF DESCRIPTION OF THE DRAWINGS

The features of the imageable particles disclosed herein are described below with reference to the drawings of certain embodiments. The illustrated embodiments are intended to demonstrate, but not to limit, the present disclosure.

FIG. 1 depicts the periodic table.

FIG. 5A was performed using T2-weighted MRI imaging. FIG. 5B depicts a PET-CT image that demonstrates uptake of $^{89}$Zr functionalized YAS microspheres following catheter-directed delivery.

FIG. 6A provides an axial image from woodchuck with large single dominant hepatoma as shown in T2-weighted MRI image. FIG. 6B is a digital subtraction angiography of catheter located within the common hepatic artery just prior to delivery of $^{89}$Zr functionalized YAS microspheres.

FIGS. 7A and 7B provide imaging following a scout dose (PT1; 7A) and full dose (PT2; 7B) catheter directed delivery of $^{89}$Zr functionalized microspheres. Negligible lung uptake is noted, with appreciable differential uptake within tumor vs. normal liver.

DETAILED DESCRIPTION

Figure 2:
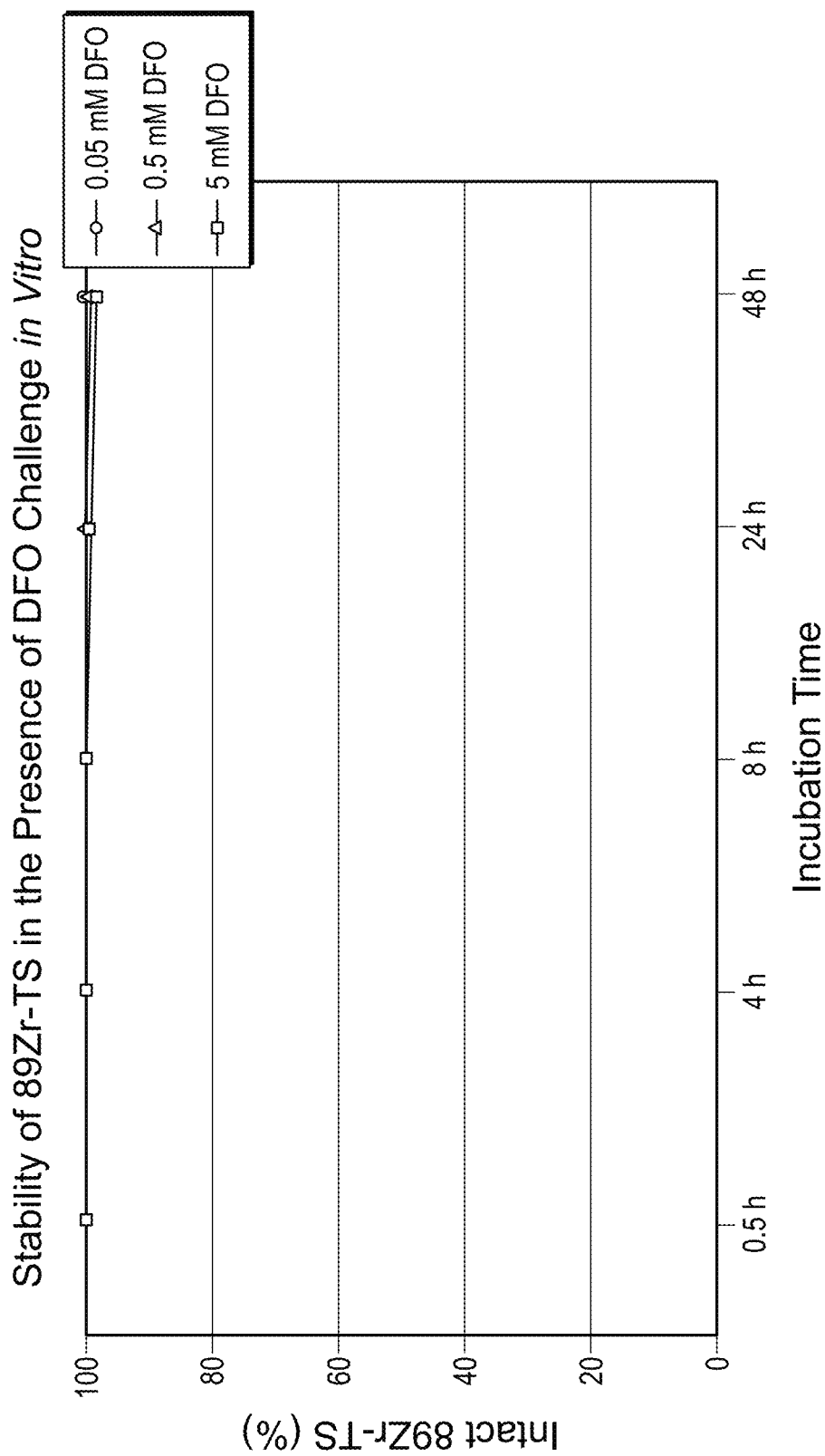
FIG. 2 depicts results of a detachment study for an embodiment of an imageable radioisotopic particle.

Some embodiments disclosed herein pertain to particles (e.g., microspheres) comprising imageable radioisotopes which may be used as surrogates for therapeutic particles (e.g., therapeutic radioisotopic microspheres surrogates) such as those suitable for use in selective internal radiation therapy (SIRT), methods of making imageable radioisotopic particles, methods of using imageable radioisotopic particles for biological imaging and for dosimetry, and methods of treatment of patients using information gathered using imageable radioisotopic particles. In some embodiments, an imageable radioisotope is functionalized (via chemical bonding) to the surface of a particle to prepare the imageable radioisotopic particle. In some embodiments, the chemical bond is a Lewis acid-base interaction between the imageable radioisotope and a surface of the substrate of the particle. In some embodiments, the imageable particle is used as a proxy (e.g., a surrogate) for a therapeutic microsphere to determine where a therapeutic microsphere will travel in the body upon introduction thereto and how a population of therapeutic microspheres will distribute within the body when delivered to a blood vessel. Some embodiments relate to the field of therapy using microspheres, including SIRT.

As used herein, the term "chemical bond" is given its plain and ordinary meaning and refers to a lasting attraction between atoms, ions or molecules that enables the formation of chemical compounds. The bond may result from the electrostatic force of attraction between oppositely charged ions as in ionic bonds or through the sharing of electrons as in covalent bonds. Chemical bonds include "strong" or "primary bonds" such as covalent, ionic and metallic bonds, and "weak bonds" or "secondary bonds" such as dipole-dipole interactions, the London dispersion force and hydrogen bonding.

As used herein, the term "coordinate bond" is given its plain and ordinary meaning and refers to a covalent bond in which both electrons come from the same atom.

As used herein, the term "covalent bond" is given its plain and ordinary meaning and refers to a bond between atoms formed by sharing a pair of electrons.

As used herein, the term "Lewis acid" is given its plain and ordinary meaning and refers to any species (molecule or ion) that is an electron-pair acceptor.

As used herein, the term "Lewis base" is given its plain and ordinary meaning and refers to any species (molecule or ion) that is an electron-pair donor.

As used herein, the term "Lewis acid-base adduct" is given its plain and ordinary meaning and refers to a compound that contains a coordinate covalent bond between a Lewis acid and a Lewis base.

As used herein, the term "half-life" or $t_{1/2}$ is given its plain and ordinary meaning and refers to the time required for one-half of the atoms of a radioisotope to decay.

Figure 1:
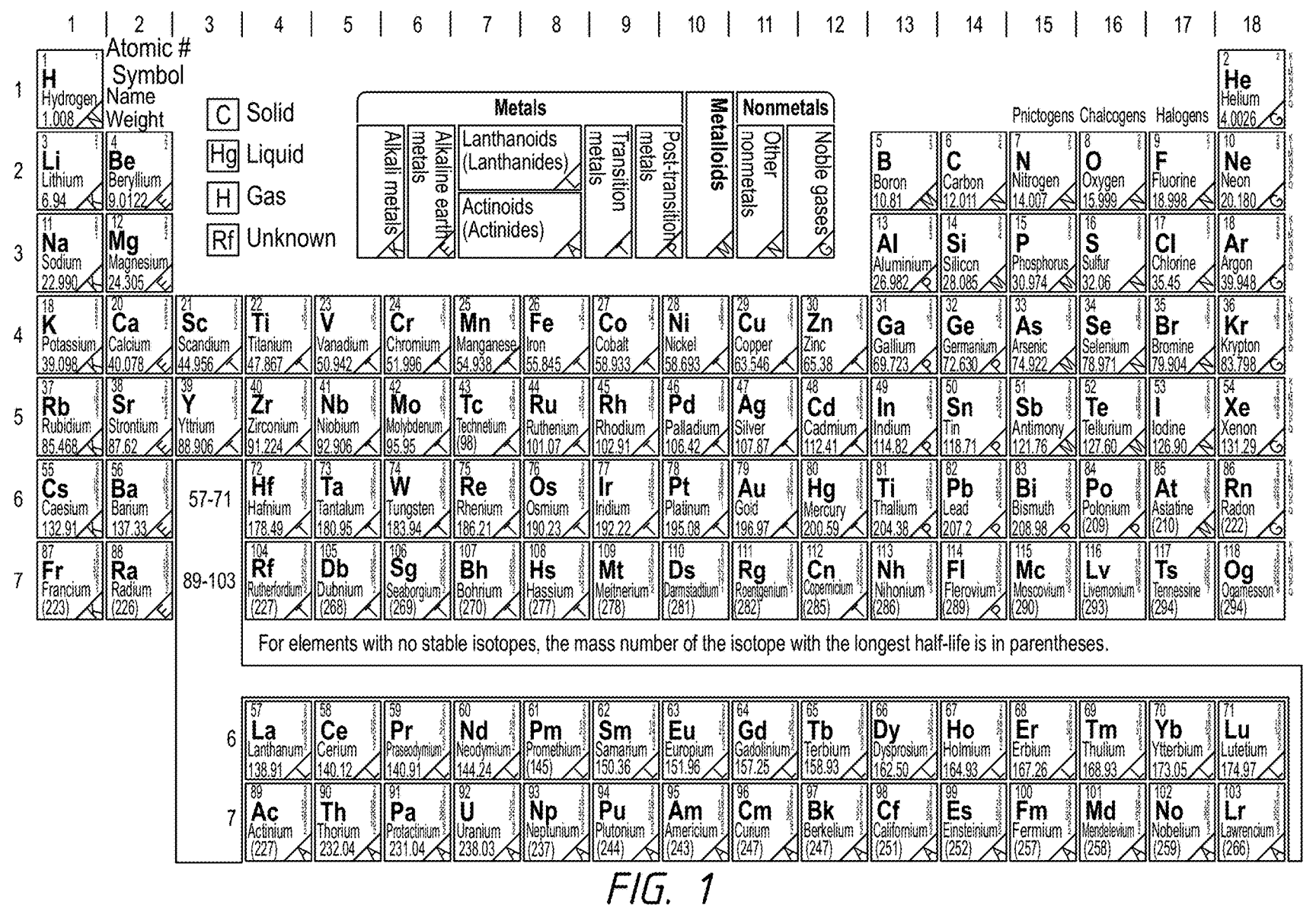

As used herein, the term "metalloid" refers to a type of chemical element which has properties in between, or that are a mixture of, those of metals and non-metals. Metalloids include, at least, boron (B), silicon (Si), germanium (Ge), arsenic (As), antimony (Sb), and tellurium (Te). The metalloids are shown in the periodic table of FIG. 1.

As used herein, the term "metal" refers to a type of chemical element of the periodic table that includes the alkali metals, the alkaline earth metals, and the transition metals. The transition metals further include the post-transition metals, lanthanides, and actinides. The metals are shown in the periodic table of FIG. 1.

As used herein, the term "non-metal" refers to a type of chemical element of the periodic table. The non-metals include (C), nitrogen (N), oxygen (O), sulfur (S), and others as shown in the periodic table of FIG. 1.

As used herein the term "ceramic microsphere substrate" refers to a ceramic microsphere which forms the substrate to which the imageable radioisotope is bound.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, children, juveniles, adults and geriatric subjects. The subject can be a subject "in need of" the methods disclosed herein can be a subject that is experiencing a disease state, and the methods and compounds of the invention are used for assessing treatment options.

The term "effective amount," as used herein, refers to that amount of a recited particle and/or composition that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, particle, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Actual dosage levels of active ingredients in an active composition of the presently disclosed subject matter can be varied so as to administer an amount of the active particle(s) that is effective to achieve the desired response for a particular subject and/or application. The selected dosage level will depend upon a variety of factors including, but not limited to, the activity of the composition, route of administration, distribution of the composition, severity of the condition being treated, and the physical condition and prior medical history of the subject being treated. In some embodiments, a minimal dose is administered. Determination and adjustment of an effective dose, as well as evaluation of when and how to make such adjustments, are contemplated herein.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, hydroxy, alkoxy, cyano, halogen, C-amido, N-amido, C-carboxy, O-carboxy, haloalkyl, haloalkoxy, a mercapto, an amino, a mono-substituted amino group, and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, or heteroaryl group. That is, the alkyl, alkenyl, alkynyl, ring of the cycloalkyl, ring of the cycloalkenyl, ring of the cycloalkynyl, ring of the aryl, or the ring of the heteroaryl can contain from "a" to "b", inclusive, carbon atoms. Thus, for example, a "$C_1$ to $C_4$ alkyl" group refers to all alkyl groups having from 1 to 4 carbons (e.g., 1, 2, 3, or 4), that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. A "$C_1$ to $C_6$ alkyl" group refers to all alkyl groups having from 1 to 6 carbons (e.g., 1, 2, 3, 4, 5, or 6). If no "a" and "b" are designated with regard to an alkyl, alkenyl, alkynyl, cycloalkyl cycloalkenyl, cycloalkynyl, aryl, or heteroaryl group, the broadest range described in these definitions is to be assumed.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by $\sim\!\!\sim\!\!\sim$, followed by the number of carbon atoms, followed by a "*". For example,

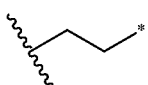

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g.,

).

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including, but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s), or as otherwise noted herein. A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include, but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, the term "amino" refers to a —NH$_2$ group.

As used herein, the term "hydroxy" refers to a —OH group.

As used herein, the term "cyano" refers to a "—CN" group.

As used herein, the term "mercapto" refers to an "—SH" group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl)

is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, the term "C-amido" refers to a "—C(=O)N($R_A R_B$)" group in which $R_A$ and $R_B$ can be independently hydrogen, alkyl, alkenyl, alkynyl, cycloalkyl, cycloalkenyl, aryl, or heteroaryl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, or heteroaryl. An N-amido may be substituted or unsubstituted.

As used herein, the term "O-carboxy" refers to a "RC(=O)O—" group in which R can be hydrogen, alkyl, alkenyl, alkynyl, cycloalkyl, cycloalkenyl, aryl, or heteroaryl, as defined herein. An O-carboxy may be substituted or unsubstituted.

As used herein, the terms "ester" and "C-carboxy" refer to a "—C(=O)OR" group in which R can be the same as defined with respect to O-carboxy. An ester and C-carboxy may be substituted or unsubstituted.

As used herein, the term "halogen atom" or "halogen" refers to any one of the radio-stable atoms of column 7 of the Periodic Table of the Elements, such as, fluorine, chlorine, bromine and iodine.

As used herein, "haloalkyl" refers to an alkyl group in which one or more of the hydrogen atoms are replaced by a halogen (e.g., mono-haloalkyl, di-haloalkyl and tri-haloalkyl). Such groups include, but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "diamino group" refers to a compound having two amino groups that are connected by an $C_{1-10}$alkyl chain, where the two amino groups independently optionally substituted (e.g., di-substituted amino groups or tri-substituted amino groups optionally substituted with additional $C_{1-6}$alkyl groups).

As used herein, "triamino group" refers to a compound having three amino groups that are connected by two or three $C_{1-10}$alkyl chains (e.g., forming a cyclic structure or a straight chain), where the three amino groups are independently optionally substituted (e.g., di-substituted amino groups or tri-substituted amino groups optionally substituted with additional $C_{1-6}$alkyl groups).

As disclosed elsewhere herein, radioactive microspheres for use in SIRT can be delivered (e.g., via the trans catheter route) to a point in the vasculature from where they are carried by blood flow and/or injected fluid into the tissue of interest. Here they lodge in the capillaries and deliver a dose of therapeutic radiation, which is typically sufficient to cause localised tissue death. Therapeutic radiation typically is delivered in the form of beta or gamma radiation from beta or gamma emitting radioactive isotopes. A variety of therapeutic isotopes, including but not limited to yttrium-90 and holmium-166 may be used in SIRT. In one approach, glass microspheres comprising yttrium-90 (a beta emitter) are used for SIRT. These are prepared by neutron bombardment of non-radioactive glass microspheres comprising naturally occurring yttrium-89, which converts it to yttrium-90 by neutron capture.

The section headings used herein are for organizational purposes only and are not to be construed as limiting the described subject matter in any way. All literature and similar materials cited in this application including, but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the general description and the following detailed description are exemplary and explanatory only and are not restrictive. The term "and/or" denotes that the provided possibilities can be used together or be used in the alternative. Thus, the term "and/or" denotes that both options exist for that set of possibilities.

Introduction

Because the circulatory system of different people can vary widely, patient receiving SIRT may meet with various levels of success. This may be in part due to off-target distribution of therapeutic radioisotopic microspheres. If introduced into the blood vessels, therapeutic radioisotopic microspheres may distribute in unexpected ways and in unintended areas of the body, this can be due for example to blood vessels present in a small percentage of the population which shunt a proportion of the blood supply to a tissue not normally supplied by the vessels main trunk. These vessels can lead to the delivery of radioactive microspheres to inappropriate tissues. Off-target distribution of microspheres is undesirable because, for example, it results in irradiation of non-target tissue, leading to unintended tissue death that can be clinically observed as an adverse patient effect. For example, if a lung shunt is present (i.e., a vessel directing blood unexpectedly to the lung from the tissue of primary interest, such as the liver) therapeutic radioisotopic particles aggregate in the lungs, they may damage the lung tissue.

Additionally, another problem with off-target delivery is that it also reduces the number of microspheres delivered to the target tissue. Hence other tissues receive radiation instead of the target tissue, reducing the dose of radiation delivered to that target tissue. This can cause the cancer to be treated ineffectively, leading to higher incidences of mortality.

Moreover, beta radiation does not lend itself to accurate imaging techniques. Beta radiation which, while very desirable for tumor treatment, has a very short effective range and is difficult, if not impossible, to detect outside the body. Additionally, the low Bremsstrahlung from beta emission and positron emission from these therapeutic microspheres lends itself to poor imaging quality and poor accuracy.

Prior to treatment, it is usual for the local vasculature to be mapped using an iodinated contrast agent, which allows the vessels to be visualised by X-ray based techniques. This allows the physician to better understand the local vascular anatomy and to plan delivery of the radioactive microspheres to the appropriate vessels feeding the tissue of interest. For a number of reasons, however, these contrast agents may be difficult to detect in small quantities and are poor proxies for therapeutic radioisotopic microspheres. Because the contrast agents may be different shapes and sizes and may have different properties than the therapeutic radioisotopic microspheres, there remains a risk that a proportion of the radioactive microspheres may lodge in off-target locations (e.g. due to passage through the tissue of interest into vessels flowing to remote tissues). Thus, mapping the vasculature by itself suffers from several drawbacks.

In addition to mapping the vasculature, it would also be of benefit to map the predicted distribution of microspheres before treatment. This may be achieved using an imageable particulate surrogate, injected into the patient's vasculature to mimic the planned SIRT procedure. One imaging particulate surrogate used currently is a macro-aggregated albumen preparation, which is labelled with technetium-99m immediately before use (known as $^{99m}$TcMAA). Technetium-99m is a short-lived gamma emitter and may be imaged using a gamma-detecting camera. Single photon emission computed tomography (SPECT) combines a gamma-detecting camera with x-ray imaging to yield images of the $^{99m}$TcMAA emissions in context of the patient's anatomy. These images can then be used to elucidate the distribution of the $^{99m}$TcMAA within the body and this information can be used to predict the final likely distribution of SIRT treatment microspheres. In this way, the proportion of delivered radiation dose that is predicted to be delivered to the tissue of interest can be calculated. Predictive dosimetry may be used to adjust the treatment plan to optimize the SIRT therapeutic dosing. The predicted distribution may also be used to triage patients suitable for treatment with SIRT. For example, if large amounts of microspheres are predicted to distribute to sensitive tissues such as lung or gut wall, it may be necessary to use angiographic techniques (e.g. coil embolization) to correct the flow of particles beyond the target tissue before proceeding with SIRT. If it is not possible to correct the non-target flow, then the SIRT dosing may need to be reduced to a safer level, or the patient may be considered unsuitable for treatment.

While $^{99m}$TcMAA has been widely used as an imaging particulate surrogate prior to SIRT therapy, $^{99m}$TcMAA is not an optimal surrogate for the treatment microspheres. For instance, the final distribution of the SIRT microspheres may not match that of the $^{99m}$TcMAA surrogate particles completely or accurately. In the case of differing distribution between $^{99m}$TcMAA surrogate particles and therapeutic particles, patients may receive one or more of an inappropriate dose of radiation to the tissue to be treated (too low or too high) or radiation to non-target tissues that was poorly predicted. Additionally, the patient may be rejected for treatment based on a faulty $^{99m}$TcMAA surrogate reading when they were, in fact, suitable.

One approach to resolve this problem was to prepare a resin or crystalline ceramic cores with imaging radioactive materials coated thereon. However, microspheres comprise a core material having an external surface coating which contains the radioactive isotope carry a high risk that the radioactive coating will separate from the underlying microsphere core. Any mechanical breakage of the coating can release unwanted radioactivity to other parts of the human body which is highly undesirable (exacerbating the issues noted above). Further disadvantages are presented by the special handling and precautions that are necessary to coat a radioactive isotope onto a ceramic core.

In still another application, microspheres may be prepared having a precursor to a radioactive isotope incorporated into a ceramic material. While the inadvertent release of radioactive isotopes from a radioactive coating into other parts of the human body is reduced by incorporating the radioisotope precursors into ceramic spheres, the latter product form is nevertheless not without its disadvantages. For example, their preparation typically requires activation of non-radioactive elements by neutron bombardment in a nuclear reactor. Further the preparation requires the use of ultrapure starting materials to avoid the production of unwanted long-lived isotopes and their commercial distribution is hampered by the necessarily short half-life of the radioisotopes and safety issues relating to transport. An additional disadvantage is a lack of flexibility in design.

Some embodiments disclosed herein address one or more of the above issues or others by providing imageable radioisotopic particles (e.g., imageable radioisotopic microspheres). In some embodiments, as disclosed in more detail elsewhere herein, imageable radioisotopes are chemically bonded to surfaces of particles to provide imageable radioisotopic particles.

Imageable Radioisotopic Particles

As noted previously, some embodiments pertain to imageable radioisotopic particles. In some embodiments, an imageable radioisotope is functionalized to the surface of a supporting substrate. In some embodiments, the supporting substrate is a particle. In some embodiments, the substrate provides the bulk of the particle (e.g., most of the size and/or weight of the particle may be attributed to the substrate). In some embodiments, the particle is a microsphere. In some embodiments, the imageable radioisotope is bound to the substrate (e.g., bound directly to the substrate). In some embodiments, the imageable radioisotope is bound to the substrate via an irreversible linkage or substantially irreversible linkage. In some embodiments, the imageable radioisotope is chemically bonded to the surface via one or more chemical bonds. In some embodiments, by providing a particle with an imageable radioisotope chemically bonded to the surface, risks associated with the imageable radioisotope detaching are lowered and/or extinguished. Moreover, because in some embodiments the imageable radioisotope can be functionalized to the substrate in its radioactive form, there is no need for neutron activation of the imageable radioisotope. For example, in some embodiments, the imageable radioisotope is bound to the surface of the substrate during preparation of the imageable particle via coupling to the substrate. In other embodiments, however, activation of nonradioactive isotopes to form imageable radioisotopes while functionalized to the surface of a particle is envisioned.

The imageable radioisotope may be functionalized to a surface of a substrate of a particle via a chemical bond. In some embodiments, the chemical bond is a primary bond. For example, in some embodiments, the imageable radioisotope is bonded to the surface of the particle (e.g., microsphere) through one or more covalent bonds. In some embodiments, the imageable radioisotope is bonded to the surface of the microsphere through one or more coordinate bonds. In some embodiments, the imageable radioisotope is bonded to the surface of the microsphere through a dative bond. In some embodiments, the imageable radioisotope is bonded to the surface of the microsphere through covalent bonds, coordinate bonds, dative bonds, ionic bonds, or combinations thereof. In some embodiments, the imageable radioisotope is bonded to the surface of the microsphere through a Lewis Acid-Base interaction (e.g., a Lewis acid-base coordination bond). For example, in some embodiments, one or more functional groups on the surface of a substrate of the particle act as Lewis bases and form a Lewis acid-base adduct with the imageable radioisotope (which acts as a Lewis acid).

As noted elsewhere herein, in some embodiments, the substrate of the particle provides a foundation to which the imageable radioisotope may be bound. In some embodiments, the substrate includes a core of the particle that extends outwardly (e.g., from the center of the particle) to the surface of the particle. In some embodiments, the substrate is an inorganic material.

As noted elsewhere herein, the substrate may be homogeneous or substantially homogeneous. To illustrate, the surface of the particle may comprise a number of atoms that are of overlapping elements and/or are the same elements (e.g., are atoms of the same elements) as found in the core of the substrate. In some embodiments, as disclosed elsewhere herein, a portion of the atoms that provide the surface of the substrate may be bound directly to the imageable radioisotope. The portion of atoms that are bound (e.g., chemically bonded) to the imageable radioisotope may be the same type of chemical element as atoms in the core of the particle. In some embodiments, the particle comprising the imageable radioisotope that lacks any intervening molecular species or differing molecular species (such as linker groups) between the substrate and the imageable radioisotope.

In some embodiments, as disclosed elsewhere herein, the substrate comprises an inorganic material. In some embodiments, the inorganic material comprises one or more elements that are metalloids, metals, or both (as defined on the periodic table). In some embodiments, the inorganic material further comprises an element that is a non-metal. In some embodiments, the inorganic material comprises at least one non-metal, a metalloid, a metal oxide, or a transition metal oxide. In some embodiments, the metalloid atoms, metal atoms, or both are bonded to non-metal atoms, forming the substrate structure. For example, in a substrate comprising a transition metal oxide, the oxygen of the oxide is considered the non-metal chemical element providing at least a portion of the substrate. In some embodiments, the substrate comprises a crystal lattice, an amorphous structure, or combinations thereof. In some embodiments, the core of the substrate comprises a first portion of metalloid or metal atoms bonded to the non-metal atoms while the surface comprising a second portion of the metalloid or metal atoms bonded to the non-metal atoms. In some embodiments, as disclosed elsewhere herein, the imageable radioisotope is bound directly to the substrate through at least a portion of the non-metal atoms at the surface of the substrate.

As will be readily apparent, the substrate of the particles may be made of a variety of materials, such as one or more inorganic materials. In some embodiments, the substrate is an inorganic material. In some embodiments, the inorganic material comprises a ceramic material and/or is ceramic. In some embodiments, the inorganic material comprises at least one element selected from silicon, yttrium, manganese, aluminium, gallium, strontium, and titanium. In some embodiments, the inorganic material comprises glass or is glass. In some embodiments, the inorganic material comprises silicon dioxide. In some embodiments, the inorganic material comprises silicon dioxide and at least one other element selected from yttrium, manganese, aluminium, gallium, boron, strontium, and titanium. In some embodiments, the inorganic material comprises one or more of $SiO_2$, $Y_2O_3$, $MnO_2$, $AlO_3$, $Ga_2O_3$, $Fe_2O_3$, $SrO_2$, $SrCO_3$ and/or $TiO_2$. In some embodiments, the inorganic material comprises $SiO_2$ and one or more of $Y_2O_3$, $MnO_2$, $AlO_3$, $Ga_2O_3$, $Fe_2O_3$, $SrO_2$, $SrCO_3$ and/or $TiO_2$. In some embodiments, the inorganic material comprises $SiO_2$ and one or more of $Al_2O_3$ and/or $Y_2O_3$.

In some embodiments, the substrate comprises a ceramic material and/or is ceramic. In some embodiments, the substrate (e.g., ceramic substrate) comprises at least one element selected from silicon, yttrium, manganese, aluminium, gallium, strontium, and titanium. In some embodiments, the inorganic material (e.g., ceramic substrate) comprises glass or is glass. In some embodiments, the substrate (e.g., ceramic substrate) comprises silicon dioxide. In some embodiments, the substrate (e.g., ceramic substrate) comprises silicon dioxide and at least one other element selected from yttrium, manganese, aluminium, gallium, boron, strontium, and titanium. In some embodiments, the substrate (e.g., ceramic substrate) comprises one or more of $SiO_2$, $Y_2O_3$, $MnO_2$, $Al_2O_3$, $Ga_2O_3$, $Fe_2O_3$, $SrO_2$, $SrCO_3$ and/or $TiO_2$. In some embodiments, the substrate (e.g., ceramic substrate) comprises $SiO_2$ and one or more of $Y_2O_3$, $MnO_2$, $Al_2O_3$, $Ga_2O_3$, $Fe_2O_3$, $SrO_2$, $SrCO_3$ and/or $TiO_2$. In some embodiments, the substrate (e.g., ceramic substrate) comprises $SiO_2$ and one or more of $Al_2O_3$ and/or $Y_2O_3$.

In some embodiments, substrate comprises yttrium aluminum silicon oxide. In some embodiments, the yttrium aluminum silicon oxide is $17Y_2O_3$-$19Al_2O_3$-$64SiO_2$ by mol %. As disclosed elsewhere herein, in some embodiments, the imageable surrogates disclosed herein are used as surrogates for TheraSphere® (Biocompatibles UK Ltd). TheraSphere® consists of insoluble glass microspheres where yttrium is an integral constituent of the glass (i.e., the TheraSphere® comprises an yttrium aluminum silicon oxide). The yttrium in the precursor particles in TheraSphere® is in the form of the naturally occurring non-radioactive isotope $^{89}Y$. $^{89}Y$ is not a beta emitter and is not radiotherapeutic. Prior to use as a radiotherapeutic, the precursor particles are bombarded with neutrons to convert $^{89}Y$ in the particles to the beta emitting form of yttrium, $^{90}Y$ (thereby resulting in active TheraSphere® particles). In some embodiments, the substrate used for the imageable radioisotopic particles disclosed herein are precursor TheraSphere® particles including $^{89}Y$ and lacking $^{90}Y$. In other words, the yttrium in yttrium aluminum silicon oxide as disclosed herein is provided in its abundant natural form ($^{89}Y$), which does not emit beta radiation. In some embodiments, however, the imageable radioisotopes may be coupled to activated yttrium containing microspheres and the microspheres may comprise $^{90}Y$.

In some embodiments, as disclosed elsewhere herein, the substrate comprises a single material, while in others, it can comprise more than one material. Where the substrate is a substantially homogeneous material, in some embodiments, it may comprise a substantially homogeneous mixture of constituent elements (e.g., Si and O in $SiO_2$). Where the substrate is homogeneous, the surface also comprises at least a portion of those constituent elements (e.g., Si and O atoms), though the surface may also comprise a terminating atom (such as a —H in an —OH). In some embodiments, atoms that are provided within the core are also provided on the surface as part of terminal functional groups (e.g., an O in a —OH). As noted above, the terminal functional groups may additionally comprise terminal atoms (e.g., the —H of an —OH). Such an arrangement is provided below for illustration.

The particle, where made from $SiO_2$, may be represented by the following structure (I):

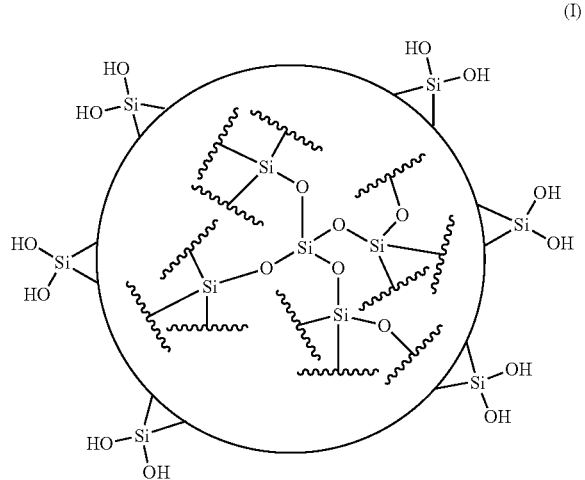

(I)

While the structure of Formula (I) comprises terminal groups that may be substantially absent in the core of the substrate, this particle would still be considered homogeneous because the elements at the surface that are not constituents of the core are provided as terminal groups.

More generally, in some embodiments, the particle may be represented as the structure having Formula (II):

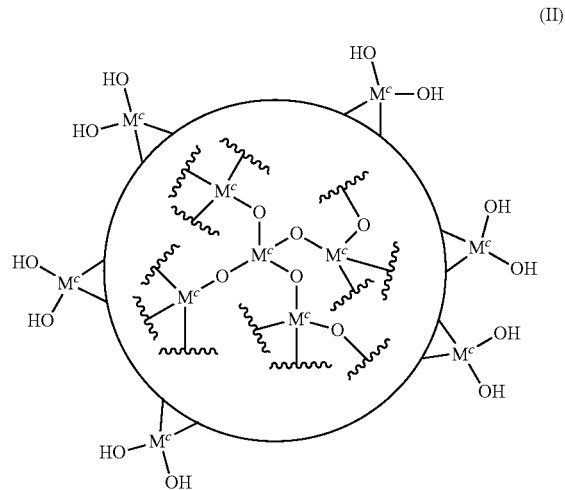

(II)

where each instance of $M^c$ is independently selected from the group consisting of Pb, Al, Si, Y, Mn, Ga, Sr, Fe, and Ti. In some embodiments, $M^c$ is selected from the group consisting of Pb, Al, Si, Y, Mn, Ga, Fe, and Ti. In some embodiments, each instance of $M^c$ is independently selected from Si, Y, and Al. In some embodiments, when the surface of the substrate is functionalized, the one or more OH groups at the surface can comprise $M^b(X)_n$ as disclosed elsewhere herein.

In some embodiments, the terminal groups of the substrate provide functional groups that may interact with an imageable radioisotope to chemically bond to the imageable radioisotope, thereby forming the imageable particle. Thus, in some embodiments, the imageable radioisotope is chemically bonded directly to the surface of the substrate of the particle. In some embodiments, as exemplified in the structures above, an inorganic substrate may comprise a surface having one or more electron donating functionalities (e.g., —OH) that coordinate or covalently bond to an imageable radioisotope, thereby bonding it to the surface.

As noted above, the imageable radioisotope may decorate the surface of the particle to provide an imageable particle. In some embodiments, on average, each particle (e.g., microsphere) comprises a plurality of radioisotopes bound to the substrate (e.g., 2, 3, or 4). In some embodiments, on average, each particle (e.g., microsphere) comprises a single radioisotope bound to the substrate. In some embodiments, not every microsphere is labelled with an imageable radioisotope. In some embodiments, the number of imageable radioisotopes per particle (e.g., functionalized to each particle) is equal to or less than about: $1 \times 10^{-6}$, 0.0001, 0.001, 0.01, 0.1, 0.5, 1, 2, or ranges including and/or spanning the aforementioned values.

In some embodiments, the imageable radioisotope is characterized by the emission of a detectable radiation. In some embodiments, the detectable radiation is one that is detectable with standard medical imaging techniques. In some embodiments, the imageable radioisotope emits radiation that is directly detectable, indirectly detectable, or both (e.g., where the radiation is detectable by an imaging modality). For instance, a directly detectable radiation may include gamma rays from a gamma emitting radioisotope. In other embodiments, the radiation may itself not be detected, but instead can lead to the production of another different form of radiation that is imageable. To illustrate, the imageable radioisotope may be a positron emitter. Once ejected from the imageable radioisotope, the positron collides with an electron inside the patient's body where the positron and electron are annihilated to produce two gamma rays. The gamma ray may then be detected. In some embodiments, the imageable radioisotope is a positron emitter, a gamma emitter, or both. In some embodiments, radiation from the imageable radioisotope is directly or indirectly detectable by an imaging modality.

In some embodiments, as disclosed elsewhere herein, the imageable isotope is one that is configured for imaging by an imaging modality. In some embodiments, the imaging modality is selected from single photon imaging and double photon imaging. In some embodiments, the imageable radioisotope is configured for imaging by an imaging modality selected from positron emission tomography (PET), single photon emission computed tomography (SPECT), and gamma camera imaging.

In some embodiments, the imageable radioisotope may be a metal. In some embodiments, the imageable radioisotope is selected from technetium-99m ($^{99m}Tc$), thallium-201 ($^{201}Th$), chromium-51 ($^{51}Cr$), gallium-67 ($^{67}Ga$), gallium-68 ($^{68}Ga$), indium-111 ($^{111}In$), copper-64 ($^{64}Cu$), zirconium-89 ($^{89}Zr$), iron-59 ($^{59}Fe$), potassium-42 ($^{42}K$), rubidium-82 ($^{82}Rb$), sodium-24 ($^{24}Na$), titanium-45 ($^{45}Ti$), scandium-44 ($^{44}Sc$), chromium-51 ($^{51}Cr$), fluorine-18 ($^{18}F$), lutetium-177 ($^{177}Lu$), and/or combinations thereof.

As noted above, in some embodiments, the imageable radioisotope is chemically bonded to the surface of the substrate via one or more chemical bonds. In some embodiments, the imageable radioisotope may also be (or alternatively be) functionalized to a surface of the substrate of a particle at least in part through an inorganic bridge. An inorganic bridge is a series of atoms bonded together that lacks an organic portion. As used herein, the term inorganic is used in its conventional sense and would be understood one of skill in the art to refer to compounds (or portions thereof or atoms thereof) that lack organic carbon-based portions (such as alkyls, etc.). Inorganic, as used herein, does not include organometallic entities.

Where present, the inorganic bridge comprises a metal atom or metalloid atom that is not the radioisotope (e.g., a bridging metal atom). The inorganic bridge also comprises one or more nonmetal atoms chemically bonded with the bridging atom (e.g., the bridging metal atom) in a series that spans between the imageable radioisotope and the substrate, in other words, bridging between the imageable radioisotope and the substrate. In some embodiments, each atom making the inorganic bridge is chemically bonded to another atom in the inorganic bridge thereby connecting the substrate and the imageable radioisotope through chemical bonds. In some embodiments, the inorganic bridge comprises a non-metal atom of the substrate, a bridging atom (e.g., a bridging metal atom), and a non-metal atom that is, in turn, chemically bonded to the imageable radioisotope. In some embodiments, the non-metal atom of the substrate is chemically bonded to the bridging atom (e.g., a bridging metal atom) and the bridging atom is chemically bonded to the non-metal atom that is chemically bonded to the imageable radioisotope.

In some embodiments, the bridging metal atom (e.g., Sn) initially acts as a reducing agent for the imageable radioisotope (e.g., $^{99m}$Tc) during functionalization of the substrate with the imageable radioisotope. The bridging atom then may remain chemically bonded (e.g., through chemical bonding such as covalent bonding, coordinate bonding, and/or Lewis acid base interactions) between the imageable radioisotope and the substrate. The imageable radioisotope and the bridging metal atom may be separated by a nonmetal atom (e.g., O) that may be chemically bonded to both the imageable radioisotope and the bridging metal atom. This non-metal atom may be part of the inorganic bridge. Similarly, a nonmetal atom of the substrate (e.g., O) may be directly bonded to the bridging metal atom connecting the bridging metal atom to the substrate. Without being bound by any particular mechanism, it is believed that tin (Sn) is a bridging atom for $^{99m}$Tc and acts as part of an inorganic bridge between $^{99m}$Tc and the substrate. In some embodiments, the inorganic bridge comprises or consists of —O—Sn—O— that chemically connects (e.g., through chemical bonding) the substrate to the imageable radioisotope (e.g., $^{99m}$Tc). In some embodiments, for example those of formula VIII, the inorganic bridge comprising an —O—Sn—O— bridge may be further bonded to one or more of —OH, ═O, and —O— (e.g., as —O—Sn(X)$_n$—O—, where each instance of X is —OH, ═O, and —O⁻ and n is 1 or 2).

In some embodiments, the imageable radioisotope may bind both directly to the substrate through atoms of the substrate (e.g., nonmetal atoms such as O) and via an inorganic bridge (e.g., through the metal atom that is not the radioisotope) simultaneously. Such a configuration is shown in certain configurations of Formula (VIII) below. In other embodiments, the metal atom that is not the radioisotope forms chemically bonded bridge between the radioisotope and the surface of the substrate and the radioisotope itself is chemically bonded to the substrate only through the bridging metal atom (or multiple bridging metal atoms), as shown in some configurations of Formula (V) below. For example, as shown in Formula (V), the bridging metal can be chemically bonded to two non-metals where the two non-metal atoms (e.g., O) are further both chemically bonded to the imageable radioisotope.

In some embodiments, the imageable radioisotope may be a non-metal. In some embodiments, the imageable particle may comprise an imageable feature that may be a metal bonded to an imageable radioactive isotope that is not a metal. For instance, a complex between a metal and an imageable non-metal radioisotope such as Al$^{18}$F. In some embodiments, this imageable complex chemically bonds to the surface via the aluminium atom with $^{18}$F being complexed to the aluminium atom. In some embodiments, the imageable complex is Al$^{18}$F.

As noted above, in some embodiments, the radioisotope is coupled to the surface of a particle via the substrate of the particle. In some embodiments, the functionalization of the surface of the particle can be represented by the following Formula

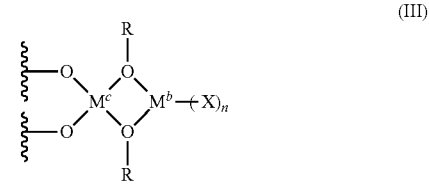

(III)

where the substrate comprises $M^c$ and $M^b$ is an imageable radioisotope. In some embodiments, $M^c$ is selected from Si, Mn, Y Al, Sr, Ga, Fe, Ti, and Pb (particularly Si, Mn, Ti, and Pb); $M^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, Al$^{18}$F, and $^{177}$Lu; each instance of R is not present or is —H; each instance of X is independently selected from —OH, ═O, and —O⁻; and n is an integer selected from 0, 1, 2, 3, or 4. In some embodiments, M is selected from Sn, Si, Mn, Al, Ga, Fe, Ti, and Pb; $M^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, Al$^{18}$F, and $^{177}$Lu; each instance of R is not present or is —H; each instance of X is independently selected from —OH, ═O, and —O⁻; and n is an integer selected from 0, 1, 2, 3, or 4. In some embodiments, the substrate comprises $M^c$ and $M^b$ is an imageable radioisotope, $M^c$ is selected from Si, Mn, Al, Ga, Fe, Ti, and Pb, (particularly Si, Mn, Ti, and Pb); $M^b$ is $^{89}$Zr; each instance of R is —H; each instance of X is —OH; and n is 2.

In some embodiments, the functionalization of the surface of the particle can be represented by the following Formula (IIIa):

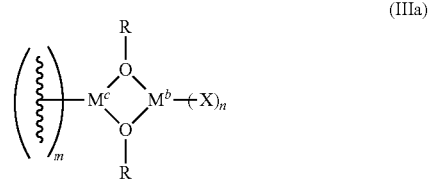

(IIIa)

where variables are as disclosed elsewhere herein. For example, in several embodiments, the substrate comprises $M^c$ and $M^b$ is an imageable radioisotope. In some embodiments, $M^c$ is selected from Si, Mn, Y Al, Sr, Ga, Fe, Ti, and Pb (particularly Si, Mn, Ti, and Pb); m is an integer selected from 1, 2, or 3; $M^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{4}$Sc, $^{51}$Cr, Al$^{18}$F, and $^{177}$Lu; each instance of R is not present or is —H; each instance of X is independently selected from —OH, =O, and —O$^-$; and n is an integer selected from 0, 1, 2, 3, or 4. In some embodiments, M$^c$ is selected from Sn, Si, Mn, Al, Ga, Fe, Ti, and Pb; M$^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{4}$Sc, $^{51}$Cr, Al$^{18}$F, and $^{177}$Lu; each instance of R is not present or is —H; each instance of X is independently selected from —OH, =O, and —O$^-$; and n is an integer selected from 0, 1, 2, 3, or 4. In some embodiments, the substrate comprises M$^c$ and M$^b$ is an imageable radioisotope, M$^c$ is selected from Si, Mn, Al, Ga, Fe, Ti, and Pb, (particularly Si, Mn, Ti, and Pb); M$^b$ is $^{89}$Zr; each instance of R is —H; each instance of X is-OH; and n is 2.

In some embodiments, the imageable particle may be represented by the following structure (IV):

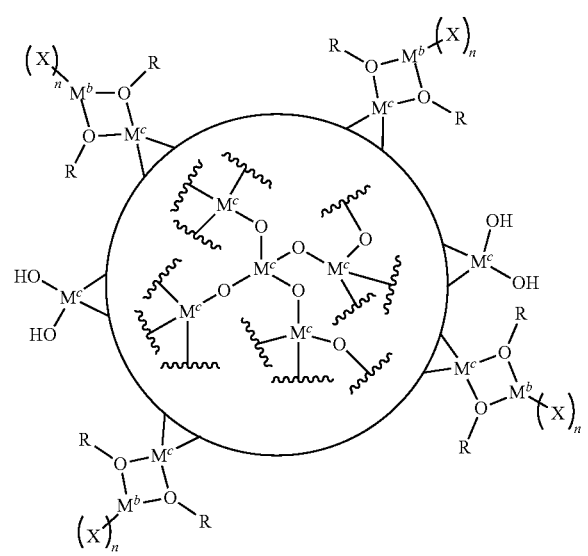

(IV)

where the variables are as defined elsewhere herein, for example according to Formula III. In some embodiments, as disclosed elsewhere herein, the substrate comprises M$^c$ and M$^b$ is an imageable radioisotope. In some embodiments, each instance of M$^c$ is independently selected from Pb, Al, Si, Y, Mn, Ga, Fe, and Ti; each instance of M$^b$ is independently selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, Al$^{18}$F, $^{177}$Lu; each instance of R is either not present or is —H; each instance of X is independently selected from —OH, =O, and —O$^-$; and n is an integer selected from 0, 1, 2, 3, or 4. In some embodiments, each instance of M$^c$ is selected from Si, Al, and Y; M$^b$ is $^{89}$Zr; each instance of X is selected from —OH; and n is 2 or 3. In some embodiments, each instance of M$^c$ is selected from Si, Al, and Y; M$^b$ is $^{89}$Zr; each instance of X is-OH; and n is 2. In some embodiments, M$^c$ is Si; M$^b$ is $^{89}$Zr; X is —OH; and n is 2. In some embodiments, R is —H. In several embodiments, where R is H, the structure of Formula (IV) may be represented by Formula (IVa) below:

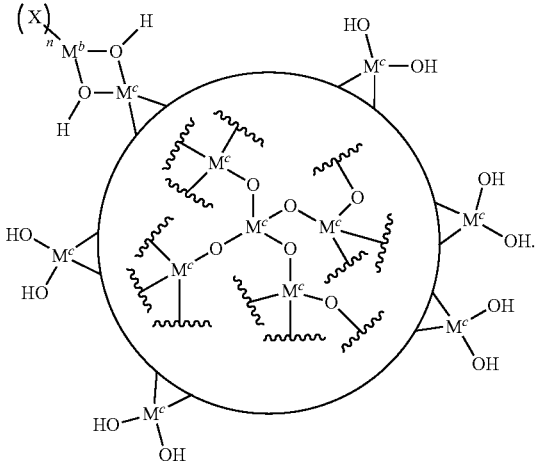

(IVa)

In several embodiments, where R is absent, the structure of Formula (IV) may be represented by Formula (IVb) below:

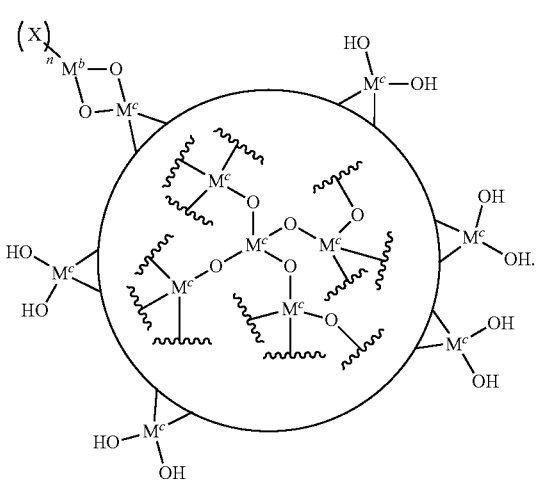

(IVb)

In some embodiments, the surface of the particle can be represented by Formula (V):

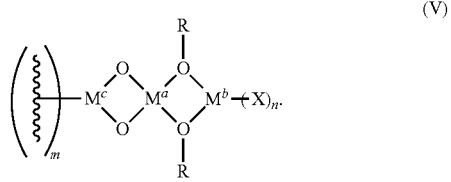

(V)

M$^a$ may either be an atom of the substrate or a bridging metal atom that connects the imageable radioisotope to the substrate through chemical bonds. In some embodiments, for example, M$^a$ is either an atom of the substrate or a bridging atom and M$^a$ is selected from Pb, Al, Si, Y, Mn, Ga, Fe, Ti, Sr, and Sn; the substrate comprises M$^c$ and M$^c$ is independently selected from Pb, Al, Si, Y, Mn, Ga, Fe, and Ti; m is an integer selected from 1, 2, or 3; M$^b$ is selected from $^{99m}$Tc $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof; each instance of R is independently either not present or is —H; each instance of X is independently selected from —OH, =O, —O$^-$, a mono-substituted amino group, a di-substituted amino group, halogen, —CN, —CF$_3$, an optionally substituted diamino group, an optionally substituted triamino group, wherein the substituent or substituents of the amino group, where present, are independently C$_{1-6}$ alkyl, heteroaryl, or aryl; n is an integer selected from 0, 1, 2, 3, or 4; and m is an integer equal to 1, 2, or 3. In some embodiments, each instance of R is either not present or is H; X is selected from —OH, =O, and —O$^-$; and n is an integer selected from 0, 1, 2, 3, or 4. In some embodiments, M$^a$ is Sn and M$^a$ is a bridging metal atom. In some embodiments, the substrate comprises M$^a$ and M$^c$ while M$^b$ is an imageable radioisotope. In some embodiments, M$^a$ and M$^c$ are independently selected from Pb, Al, Si, Y, Mn, Ga, Fe, and Ti; M$^b$ is selected from $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{4}$Sc, $^{51}$Cr, Al$^{18}$F, and $^{177}$Lu; each instance of R is independently either not present or is —H; each instance of X is independently selected from =O, —O$^-$, —OH, a mono-substituted amino group, a di-substituted amino group, halogen, —CN, —CF$_3$, an optionally substituted diamino group, an optionally substituted triamino group, wherein the substituent or substituents of the amino group, where present, are independently C$_{1-6}$ alkyl, heteroaryl, or aryl; n is an integer selected from 0, 1, 2, 3, or 4; and m is an integer equal to 1, 2, or 3.

In some embodiments, the substrate comprises M$^c$ and M$^c$ is independently selected from Pb, Al, Si, Y, Mn, Ga, Fe, and Ti; m is an integer selected from 1, 2, or 3; M$^b$ is $^{99m}$Tc; M$^a$ is Sn; each instance of R is either not present or is H; X is —OH or =O; and n is 2 or 3.

In some embodiments, M$^a$ is Si, Y, and Al; M$^b$ is $^{89}$Zr, M$^c$ is selected from Si, Al, and Y; X is —OH; and n is 2. In some embodiments, M is Si, Al, or Y; M$^a$ is Sn; M$^b$ is $^{99m}$Tc; each X is independently —OH or =O; and n is 2 or 3. In some embodiments, M$^b$ is $^{99m}$Tc, X is —OH, and n is 2 or 3.

Alternatively, in some embodiments, M$^b$ may be an imageable radioisotope comprising a host metal bonded to a radioactive isotope that is not a metal. For instance, the complex with a non-metal imageable radioisotope such as Al$^{18}$F. In some embodiments, this complex chemically bonds to the surface via the aluminium atom with $^{18}$F being complexed to the aluminium atom. In some embodiments, M$^a$ and M$^c$ are independently selected from Si, Al, Y, and Sn; M$^b$ is selected from $^{99m}$Tc and $^{89}$Zr; each instance of X is —OH; and n is 2 or 3. In some embodiments, M$^a$ and M$^c$ are independently selected from Si, Al, Y, and Sn; M$^b$ is $^{99m}$Tc; each instance of X is —OH; and n is 2 or 3. In some embodiments, M$^a$ and M$^c$ are independently selected from Si, Al, Y, and Sn; M$^b$ is $^{99m}$Tc; each instance of X is selected from —OH and Sn; and n is 3. In some embodiments, M$^a$ and M$^c$ are independently from Si, Al, and Y; M$^b$ is $^{89}$Zr; each instance of X is —OH; and n is 2. In some embodiments, M$^a$ is Si; M$^c$ is Al; M$^b$ is $^{89}$Zr; X is —OH; and n is 2. In some embodiments, M$^a$ is Si; M$^c$ is Al; M$^b$ is $^{99m}$Tc; each instance of X is independently selected from —OH and Sn; and n is 3. In some embodiments, R is —H.

In some embodiments, the surface of the particle can be represented by Formula (VI):

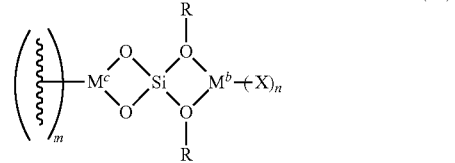

(VI)

where M$^c$, M$^b$, R, X, m, and n are as disclosed elsewhere herein. M$^c$, M$^b$, R, X, m, and n may be, for example, as disclosed in relation to Formula (V).

In some embodiments, the surface of the particle can be represented by Formula (VII):

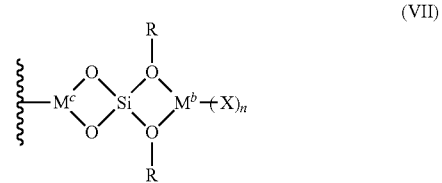

(VII)

where M$^c$, M$^b$, R, X, and n are as disclosed elsewhere herein. M$^c$, M$^b$, R, X, m, and n may be, for example, as disclosed in relation to Formula (V).

In some embodiments, the surface of the particle can be represented by Formula (VIII):

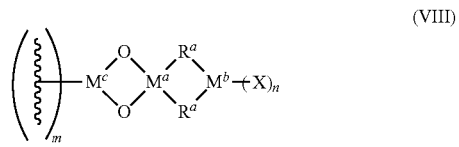

(VIII)

where M$^c$, M$^b$, X, and n are as disclosed elsewhere herein. In some embodiments, the substrate comprises M$^a$ and M$^c$ and M$^a$ and M$^c$ are independently selected from Pb, Al, Si, Y, Mn, Ga, Fe, Sr, and Ti; m is an integer selected from 1, 2, or 3; M$^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof; M$^a$ is either an atom of the substrate or a bridging atom and M$^a$ is selected from Sn, Pb, Al, Si, Y, Mn, Ga, Fe, and Ti; each instance of R$^a$ is independently OH, O—, —O—Sn(X)$_n$—O or —O—Sn—O—; each instance of X is selected from —OH, =O, and —O$^-$; and each instance of n is an integer selected from 0, 1, 2, 3, or 4. In some embodiments, M$^c$ is Al; M$^a$ is Si; M$^b$ is $^{99m}$Tc; each X is independently —OH or =O; and n is 2 or 3. In some embodiments, M$^c$ is Al; M$^a$ is Si; M$^b$ is $^{99m}$Tc; at least an instance of R$^a$ is —O—Sn—O—, each X is independently —OH or =O; and n is 2 or 3. In some embodiments, M$^c$ is Al; M$^a$ is Si; M$^b$ is $^{99m}$Tc; at least an instance of R$^a$ is —O—Sn(X)$_n$—O—, each X is independently —OH or =O; and each instance of n is independently 2 or 3. In some embodiments, M$^b$ is $^{99m}$Tc; at least an instance of R$^a$ is —O—Sn—O—, each X is independently —OH or =O; and n is 2 or 3. In some embodiments, M$^b$ is $^{99m}$Tc; at least an instance of R$^a$ is —O—Sn(X)$_n$—O—, each X is —OH; and n is 2. In some embodiments, M$^b$ is $^{99m}$Tc; an instance of $R^a$ is —O—Sn—O—, an instance of $R^a$ is —O— or —OH—; each X is independently —OH or =O; and n is 2 or 3. In some embodiments, $M^b$ is $^{99m}$Tc; an instance of $R^a$ is —O—Sn(X)$_n$—O—, an instance of $R^a$ is —O— or —OH—; each X is independently —OH or =O; and n is 2 or 3.

In some embodiments, the imageable particle may be represented by a structure as depicted in Formula (IX):

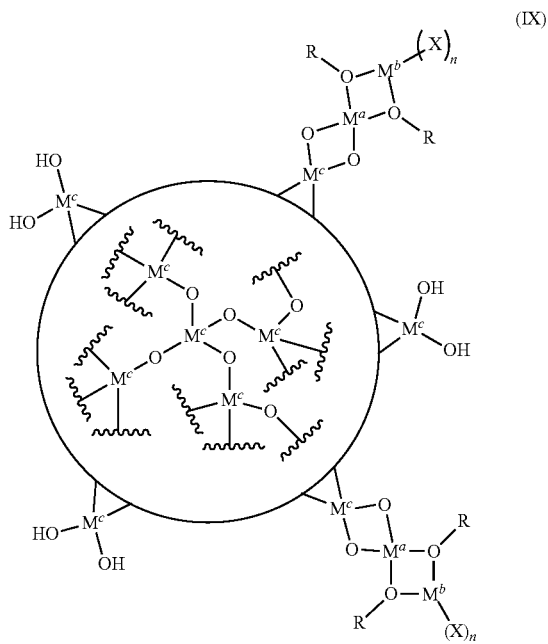

(IX)

where the variables are as defined elsewhere herein.

In some embodiments, the imageable particle may be represented by a structure as depicted in Formula (X):

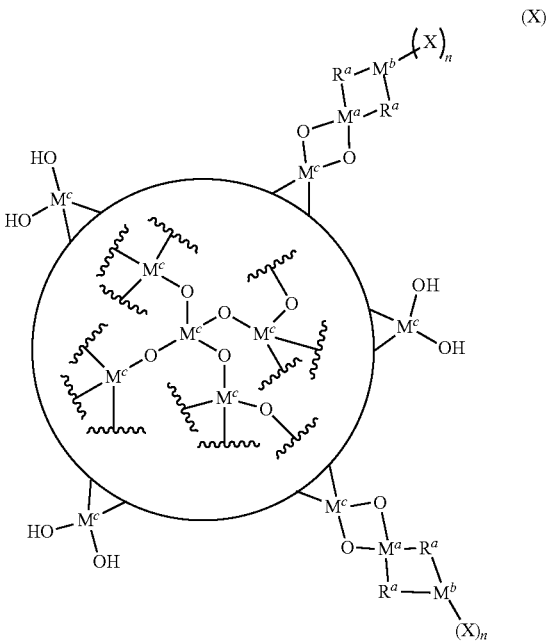

(X)

where the variables are as defined elsewhere herein.

In some embodiments, the imageable radioisotope may be selected based on its half-life. For instance, in some embodiments, imageable radioisotopes with shorter half-lives are selected so that the body is exposed to radiation from the imageable radioisotope for shorter periods of time. In some embodiments, the imageable radioisotope has a half-life of less than or equal to about: 1 day, 3 days, 7 days, 2 weeks, one month, two months, or ranges including and/or spanning the aforementioned values.

In some embodiments, as disclosed elsewhere herein, the imageable element is confined to the surface of the microsphere. In some embodiments, the substrate lacks an imageable radioisotope.

As noted elsewhere herein, in some embodiments, the substrate is porous. In other embodiments, the substrate is non-porous. In some embodiments, porosity of the particles herein is measured by their surface area per unit weight. In some embodiments, the surface area of the substrate of the particles as disclosed herein is less than or equal to about: 1 m$^2$/g, 0.5 m$^2$/g, 0.25 m$^2$/g, 0.1 m$^2$/g, 0.05 m$^2$/g, or ranges including and/or spanning the aforementioned values. In some embodiments, where the particle is substantially non-porous or lacks porous, the radioisotope may be bound to a peripheral surface of the particle (e.g., a surface that is not within a pore and that is not internal to the outer circumference of the particle). In other embodiments, where the particle is porous, the radioisotope may be bound to any surface of the particle, including within a cavity or pore of the particle and/or to a peripheral surface of the particle.

In some embodiments, the particles are microspheres. A microsphere is a particle having microscale dimensions. In some embodiments, the microspheres have an average size of between 5 μm and 1000 μm. In some embodiments, the particles are microspheres with an average size between 20 μm and 30 μm or between 15 μm and 100 μm. In some embodiments, the average size of the imageable particles is less than or equal to about: 500 nm, 1000 nm, 5 μm, 20 μm, 25 μm, 30 μm, 40 μm, 50 μm, 100 μm, 250 μm, 500 μm, 750 μm, 1000 μm, or ranges including and/or spanning the aforementioned values.

The diameter of the microspheres can be easily determined by light or scanning electron microscopy.

In some embodiments, the substrate for the imageable particles is selected for its similarity for example in size, shape, density and/or chemical composition, to particles currently used for SIRT and for which they are used as surrogates (except that they lack a therapeutic radioisotope). For example, TheraSphere consists of insoluble glass microspheres where yttrium-90 is an integral constituent of the glass. These radioactive glass microspheres are about 20 μm to 30 μm in diameter. By providing an imageable particle of similar dimensions and properties to the therapeutic particle, the imageable particle can act as a more accurate surrogate for the therapeutic particle. In some embodiments, the composition of the imaging particles is chosen such that the density of the imaging microspheres is the same as, or close to, the density of the treatment microspheres, so that the movement and distribution of the imaging particles will be similar to that of the treatment microspheres. In some embodiments, each milligram of imageable radioisotopic particles comprises equal to or less than about: 5,000 particles, 10,000 particles, 20,000 particles, 30,000 particles, 50,000 particles, 70,000 particles, 80,000 particles, 100,000 particles, or ranges including and/or spanning the aforementioned values.

While in several embodiments disclosed herein, reference is made to the use of a microsphere, the term particle broadly includes microspheres and other particles onto which the imageable radioisotope may be bound. For example, the particle can vary in size and shape (e.g., cylindrical, cubic, pyramidal, box-shaped, etc.). In some embodiments, the shape of the particle is selected depending on the corresponding size and shape of the therapeutic particle the imageable particle is meant to act as a surrogate for.

As noted elsewhere herein, in some embodiments, the imageable microsphere lacks a therapeutic radioisotope. In some embodiments, the imageable isotope and/or the imageable microsphere is non-therapeutic (e.g., it emits doses sufficient for and/or configured for imaging but insufficient to treat a patient). In some embodiments, the imageable microsphere is configured to not be delivered simultaneously with a therapeutic microsphere. In some embodiments, the imageable microsphere is not exposed to neutron bombardment and/or neutron activation to transform a non-imageable isotope of an element into the imageable radioisotope of the imageable microsphere. In some embodiments, the imageable radioisotope is imageable due to its radioactivity and not due to paramagnetism. In some embodiments, the imageable agent is not a paramagnetic material and/or is not an imageable agent selected from the group consisting of H-1, He-3, Li-7, B-7, B-9, N-15, 0-17, F-19, Mg-27, Al-27, Si-29, S-33, Cl-37, Ca-43, Ti-47, V-51, Cr-53, Mn-55, Fe-57, Ni-61, Cu-63, Zn-67, Ga-69, Ge-73, Kr-83, Sr-87, Y-89, Zr-91, Mo-95, Mo-97, Ru-99, Rh-103, Pd-105, Cd-11, Sn-115, Te-125, I-127, Ba-135, Ba-137, Xe-129, Xe-131, Nd-145, Gd-155, Dy-161, Er-167, Yb-171, W-183, Os-187, Pt-195, Hg-199, T1-205, Pb-207, Pt-198, and H-2. In some embodiments, the imageable microsphere lacks one or more of strontium phosphate, phosphate, or phosphorous. In some embodiments, the imageable microsphere does not comprise a strontium phosphate and/or phosphate layer over a substrate into which an imageable isotope is bound. In some embodiments, the substrate is not organic, lacks organic materials, and/or is not a resin. In some embodiments, the imageable radioisotope is not bound to the substrate by any one of a carboxylic acid group, a diphosphonic acid group, or a sulfonic acid group. In some embodiments, the imageable radioisotope is not bound to the substrate through any alkyl linker and/or through a non-metal bridge.

Methods of Manufacturing and Products Made Therefrom

Some embodiments pertain to an imageable radioisotopic particle made by a method that includes obtaining a particle as disclosed elsewhere herein. As disclosed herein, in some embodiments, the particle comprises a substrate material. In some embodiments, the substrate material comprises Lewis basic constituents about a surface of the substrate (and/or throughout the substrate). In some embodiments, a radioisotope is combined with the substrate and a chemical bond between the substrate of the particle and the radioisotope is formed. In some embodiments, an imageable radioisotope is combined with the substrate and a chemical bond is formed between the imageable radioisotope, a non-metal atom, a bridging atom, a non-metal atom, and the substrate of the particle. In some embodiments, a chemical bond between a non-metal atom and the radioisotope is also formed to provide a bridge from the radioisotope to the substrate. In some embodiments, the constituent atoms of the bridge are bound to each other through chemical bonding as disclosed herein (e.g., coordinate, covalent bonding, etc.).

Some embodiments pertain to an imageable microsphere made by a method comprising providing a substrate comprising an inorganic material comprising a metalloid or a metal. In some embodiments, the core of the substrate comprises a first portion of metalloid or metal atoms bonded to the non-metal atoms, while the surface comprising a second portion of the metalloid or metal atoms bonded to the non-metal atoms. In some embodiments, as disclosed elsewhere herein, the imageable radioisotope is bound directly to the substrate (e.g., to at least a portion of the non-metal atoms at the surface of the substrate), via a bridging metal atom through chemical bonds, or both. In some embodiments, the method further comprises obtaining at least one imageable radioisotope. In some embodiments, the method further comprises chemically coupling the at least one imageable radioisotope to the surface layer of the substrate to provide the imageable microsphere.

In some embodiments, the method comprises providing the at least one imageable radioisotope in ionic form such as in the form of a salt prior to chemically coupling the at least one imageable radioisotope to the surface layer of the inorganic substrate. In some embodiments, the imageable radioisotope (e.g., in a radioisotope salt) has an oxidation number equal to or greater than 1, 2, 3, 4, or 5. In some embodiments, the imageable radioisotope salt has one or more counter ions associated with it. In some embodiments, the counter ion has an oxidation number equal to or greater than −1 or −2. In some embodiments, the salt is a halogen salt or a polyatomic salt.

In some embodiments, the chemical functionalization is carried out in the presence of a reducing agent. In some embodiments, the substrate is contacted with the radioisotope in the presence of a reducing agent. In some embodiments, the reducing agent is selected from one or more of a tin salt (such as a stannous salt to provide stannous ions), HCl, sodium borohydride, sodium diothionite, ferrous sulfate, ferric chloride plus ascorbic acid, hypophosphorous acid, and/or hydrazine.

In some embodiments, the imageable radioisotope may be any imageable radioisotope as disclosed elsewhere herein. In some embodiments, the imageable ceramic microsphere is obtainable by reacting the ceramic microsphere with a $^{99m}$Tc, which may for example be in the form of a pertechnetate ion, in the presence of a reducing agent, such as a stannous ion (for example as a stannous halide such as stannous chloride).

Some embodiments pertain to a process for the preparation of an imageable ceramic microsphere comprising reacting a ceramic microsphere substrate (e.g. comprising at least one non-metal, metalloid, or transition metal oxide) with $^{99m}$Tc ions, such as $^{99m}$Tc pertechnetate or other Tc(VII) ions in the presence of a reducing agent as described elsewhere. The ceramic microsphere may be in the form of a glass microsphere as described elsewhere herein.

Some embodiments pertain to a process for the preparation of an imageable ceramic microsphere comprising reacting a ceramic microsphere substrate with a zirconium salt, such as $^{89}$Zr oxalate or $^{89}$Zr chloride. The reaction may be carried out in the presence of a base.

Some embodiments pertain to a method of making an imageable microsphere comprising providing the inorganic substrate and chemically functionalizing the inorganic substrate with the at least one imageable radioisotope to provide the imageable microsphere.

Some embodiments pertain to a method of making an imageable radioisotopic particle. In some embodiments, the method includes a step for providing the at least one imageable radioisotope as a salt prior to chemically functionalizing the at least one imageable radioisotope to a surface of the inorganic substrate. In some embodiments, salt is an alkali metal salt, an alkali earth metal salt, (for example when the imageable isotope is $^{18}F$) a halogen salt, or a polyatomic salt (for example when the imageable isotope is $^{89}Zr$). In some embodiments, the method comprises adding a reducing agent during the chemical functionalization step. In some embodiments, (for example where the imageable isotope is $^{99m}Tc$) the reducing agent is selected from one or more of a tin salt (such as stannous salt, such as a stannous halide, to provide stannous ions), HCl, sodium borohydride, sodium diothionite, ferrous sulfate, ferric chloride plus ascorbic acid, hypophosphorous acid, and/or hydrazine. In some embodiments, the reducing agent is one that is capable of reducing Tc(VII) to Tc(V).

In several embodiments, the radioisotope is added to the substrate (e.g., the microsphere) by adding the radioisotope (or a salt thereof) to a solution comprising the substrate. In several embodiments, the radioisotope is added to the substrate (e.g., the microsphere) by adding substrate to a solution comprising the radioisotope (or a salt thereof). In several embodiments, the solution comprises water. In several embodiments, the solution comprises saline. In several embodiments, the solution has a pH of greater than or equal to about: 3.0, 4.0, 5.0, 5.5, 6.0, 6.5, 7.0, 7.5, 8.0, 9.0, 10.0, or ranges spanning and/or including the aforementioned values. In several embodiments, the solution comprises a buffer. In several embodiments, the buffer is selected from the group consisting of phosphate buffered saline (PBS), citrate, acetate, or combinations of the foregoing. In several embodiments, the solution lacks a buffer. Suitable pH ranges include pH 3 to pH 10, and pH 5 to pH 8.

Some embodiments provide imageable microspheres obtained or obtainable by methods or processes described herein.

Methods of Using Imageable Radioisotopic Particles

As disclosed elsewhere herein, in some embodiments, a method of using imageable radioisotopic particles is provided. In some embodiments, imageable radioisotopic particles can be used as a surrogate for therapeutic radioisotopic particles without the need to expose the patient to harmful therapeutic radiation. For example, as noted above, in SIRT, therapeutic radioactive particles are introduced into a blood vessel of the body of a patient through a catheter. These therapeutic particles are often used for the treatment of vascularized tumors such as liver cancer (e.g., hepatic neoplasias such as hepatocellular carcinoma —HCC, as well as tumors derived from metastasis of other tumors to the liver, such as neuroendocrine tumors and colorectal tumors), as well as those of the brain, prostate, lung, spleen and kidney, for example.

At the outset, patients have different vascular systems generally and the blood vessels surrounding a tumor also vary person-to-person. Thus, what is therapeutic for one person may not be therapeutic or may be harmful for a different person. In some patients, the therapeutic particles may travel to unwanted areas of the body (off-target delivery), causing damage to off-target tissues. When treating the liver for example, atypical vasculature can lead to off-target localization of microspheres causing gastrointestinal tract damage, lung damage, or other unwanted site effects. A portion of microspheres delivered, or shunted, to the lungs as an off-target tissue (such as, for example, when a liver tumor is the intended target), is known as the lung shunt portion, or lung shunt fraction, for example. Further, though proxies for therapeutic particles exist, they are not well-matched and do not resemble the actual therapeutic particles. Thus, candidates who would actually have high rates of success could be rejected for treatment, while poor candidates could be treated, causing unwanted damage to other portions of the body.

The particles disclosed herein, however, are well-matched to SIRT therapeutic particles (including TheraSphere). These particles serve as more effective predictors of therapeutic distribution in the body. To that end, some of the methods disclosed herein pertain to the use of the imageable radioisotopic particles disclosed herein to predict the distribution of therapeutic radioisotopic particles in a patient. In some embodiments, as disclosed elsewhere herein, to achieve an image of a site in a patient, a population of imageable particles is administered to the patient. As disclosed elsewhere herein, different areas of the body (target and non-target sites) can then be imaged using an imaging modality. In some embodiments, the population of imageable particles can comprise particles having one imageable radioisotope type. In other embodiments, the population can comprise particles having a plurality of different radioisotope types (e.g., 2, 3, 4, or more). For example, in some embodiments, only a single radioisotope (e.g., $^{99m}Tc$) is present in the population of particles. In other embodiments, multiple types of imageable radioisotopes (e.g., $^{99m}Tc$ and $^{89}Zr$) are present in the population of particles. Some embodiments disclosed herein pertain to a population of imageable particles as disclosed comprising one or more imageable radioisotopes.

In some embodiments, the imageable radioisotopic particles can be used in methods of treating cancer, in that an appropriate dose of therapeutic radioisotopic particles can be calculated based on the distribution of the imageable radioisotopic particles. In some embodiments, the imageable radioisotopic particles may be used in methods of avoiding damage from therapeutic radioisotopic particles to off-target tissues. In some embodiments, an off-target tissue is a normal and/or healthy tissue. In some embodiments, an off-target area can include the lung or gastrointestinal tract (e.g., when liver cancer is being treated). In some embodiments, the imageable radioisotopic particles can be used in methods to calculate an appropriate dose of radiation from the therapeutic radioisotopic particles. In some embodiments, the imageable radioisotopic particles can be used in methods to determine whether a patient is likely to have success when treated with therapeutic radioisotopic particles. In some embodiments, the imageable radioisotopic particles can be used in methods of treating cancer by calculating a dose of therapeutic particles to administer.

In some embodiments, the imageable radioisotopic particles are used in a method to determine an amount of therapeutic microspheres to provide to a body of a patient. In some embodiments of the method, a population of imageable particles is acquired. In some embodiments, the signal intensity per unit dose of the imageable radioisotopic particles is calculated. In some embodiments, a patient relative calibration is used, for example, where only the treated volume and anticipated therapeutic activity is needed. In some embodiments, the population of imageable particles is then administered to the patient by introducing the population of imageable microspheres to a first position in the vasculature of the patient. In some embodiments, the microspheres are injected to multiple positions within the vasculature that may or may not overlap.

In some embodiments, after injecting the population of imageable microspheres into the patient (e.g., by a transcatheter, etc.), the particles are allowed to distribute within the body of the patient for a period of time, typically at least until the particles become lodged in the capillaries at their destination. In some embodiments, the imageable radioisotopic particles are allowed to distribute within the body for a period of time that is less than or equal to about: 5 minutes, 10 minutes, 15 minutes, 30 minutes, an hour, or ranges including and/or spanning the aforementioned values. In some embodiments, the imageable radioisotopic particles are allowed to distribute within the body for a period of time that is equal to or at least about: 5 minutes, 10 minutes, 15 minutes, 30 minutes, an hour, or ranges including and/or spanning the aforementioned values.

In some embodiments, once the imageable radioisotopic particles are distributed in the patient's body, the location and/or abundance of those particles in the body can be mapped. For example, one or more portions or sections of the body of the patient can be imaged using an imaging modality (such as a gamma camera imaging, PET (such as for $^{89}$Zr particles), SPECT scanner (such as for $^{99m}$Tc particles), or other techniques as disclosed elsewhere herein). Those portions of the body can include target sites of the body where treatment is desired. Additionally, off-target sites of the body (e.g., where treatment and/or radiation damage is not desired) can be imaged to determine whether damaging amounts of particles would reach those sites. The relative dose of imageable radioisotopic particles at each target area and/or off-target area can be determined, for example by comparing the intensity of signal at each area. In some embodiments, the dose at a particular site (e.g., at an organ or portion of the body) is determined by comparing the intensity of the radiation signal at that site versus the total intensity of radiation in the body or in some other area of the body, or in the treated volume. The relative dose of imageable radioisotopic particles at each target area and/or off-target area can be determined, for example by comparing the intensity of signal at each area. In some embodiments, the dose of therapeutic particles that would be delivered to a particular area is calculated by comparing the intensity of the radiation signal from the imageable particles at the target area and/or off-target area to the signal intensity per unit dose for the imageable radioisotopic particles.

In some embodiments the predicted dose of therapeutic particles that would be delivered to a target area is calculated by calculating the total imageable signal from the target area and any off-target area and determining the proportion of the total signal obtained from the target area. This proportion may then be used to determine the total dose of therapeutic particles to be delivered in order to deliver the required dose of therapeutic particles to the target area. This approach can also be used to determine the proportion of dose of therapeutic particles that will be delivered to any off-target tissues (e.g. lung, GI tract, brain, reproductive tissues, mucus membranes or any other radiosensitive organs). In some embodiments these calculations may be carried out on a volumetric basis, in other words on the basis of signal obtained from a volume of target and/or off-target tissue. To illustrate, when 60% of the signal from the radioisotopes is at the target site and 40% is at an off-target site, the approximate radiation dose at the target site can be calculated to be 60% of the total dose given. Similarly, the radiation dose at the off-target site can be calculated as 40%.

In some embodiments, off-target areas or sections of the body may include those that are most susceptible to unwanted damage from therapeutic radioisotopic particles. For example, the lungs and gastrointestinal system (though other portions of the body could also be imaged, such as the reproductive tissues, mucus membranes or any other radiosensitive organs, brain, kidneys, heart, etc. or any other radiosensitive organs or tissues). The target sections of the body are those that are selected for treatment (e.g., the liver of a patient suffering from a liver cancer). Target areas may include malignant tumors or benign tumors in a patient in need of treatment. Target areas may include vascularized tumors (e.g., cancerous or benign tumors) such as those found in liver cancer (e.g., hepatic neoplasias such as hepatocellular carcinoma (HCC), as well as tumors derived from metastasis of other tumors to the liver, such as neuroendocrine tumors and colorectal tumors), as well as those of the brain, prostate, lung, spleen and kidney, for example.

In some embodiments, once the relative doses at one or more target areas or off-target areas is determined, a determination can be made as to whether the patient is a good candidate for treatment. For instance, if the dose of therapeutic particles required to treat the patient's liver cancer would be so high that it might also cause lung damage or gastrointestinal damage, the patient's candidacy for treatment can be withdrawn. Such damage might occur for example if vasculature that might shunt radioactive microspheres to the lung or gastrointestinal tract, were present. If the dose of therapeutic microspheres required to treat the liver is insufficient to cause side effects (such as lung or gastrointestinal damage), the patient can be selected for treatment.

In some embodiments, the distribution of imageable radioisotopic particles can also be used to calculate an amount of therapeutic microspheres to be delivered to the body of the patient. For instance, the amount of radiation per unit dose of imageable particles at a site (target or off-target) can be used to determine the amount of therapeutic particles to administer where the amount of therapeutic radiation per unit dose of therapeutic particles is known. In some embodiments, using the imageable particles herein a target radiation dose to the liver of 80 Gy to 150 Gy can be achieved. In some embodiments, using the imageable particles herein a target radiation dose to the liver of 80 Gy to 300 Gy can be achieved. In some embodiments, using the imageable particles herein a target radiation dose to the liver of 200 Gy to 300 Gy can be achieved.

In some embodiments, the method includes obtaining data regarding a distribution of an imageable therapeutic microsphere surrogate in a patient. In some embodiments, the method includes using the data to determine a dose of a therapeutic amount of microspheres to administer to the body of the patient. In some embodiments, the method includes allowing the population of therapeutic microspheres to distribute within the body of the patient, thereby treating the patient Some embodiments pertain to a method of predicting the degree of damage to off-target tissue such as lung or gastrointestinal damage, or liver treatment during treatment of a patient in need of radioisotopic cancer treatment. In some embodiments, the method comprises introducing a population of imageable microspheres to the patient. In some embodiments, the method comprises allowing the imageable microspheres to distribute within the patient over a period of time. In some embodiments, the method comprises determining the distribution of the imageable microspheres within a lung, gastrointestinal tract, or liver of the patient by imaging the imageable microspheres using an imaging modality. In some embodiments, the method comprises determining an estimated dose of radiation in the lung, gastrointestinal tract, or liver of the patient if the imageable microspheres had been replaced by radioisotopic therapeutic microspheres. In some embodiments, the method comprises determining a dose of the radioisotopic therapeutic microspheres that is sufficient to cause clinically relevant pulmonary changes due to off-target delivery of microspheres to the lung. In some embodiments, the method comprises administering a dose of the radioisotopic therapeutic microspheres to patient that is below the dose of the radioisotopic therapeutic microspheres determined to be sufficient to cause clinically relevant pulmonary changes due to off-target delivery. In some embodiments, the method comprises determining a dose of the radioisotopic therapeutic microspheres that is sufficient to cause clinically relevant damage due to off-target delivery of microspheres to the gastrointestinal tract. In some embodiments, the method comprises administering a dose of the radioisotopic therapeutic microspheres to patient that is below the dose of the radioisotopic therapeutic microspheres determined to be sufficient to cause clinically relevant gastrointestinal tract damage due to off-target delivery.

Some embodiments provide the imageable particles and microspheres described herein for use in methods for determining or estimating the distribution of treatment microspheres or for determining the treatment dose of therapeutic microspheres as described herein.

In some embodiments, at the time of injection, a dose of microspheres having a radioactivity intensity of equal to or less than about 50 microcuries ($\mu$Ci), 100 $\mu$Ci, 150 $\mu$Ci, 250 $\mu$Ci, 1000 $\mu$Ci, 2000 $\mu$Ci, or 4000 $\mu$Ci, (or ranges including and/or spanning the aforementioned values) is injected. In some embodiments, a dose of 10 mg to 100 mg of microspheres is injected. In some embodiments, to the subject is administered a dose of less microspheres (in mg) of less than or equal to about: 10 mg, 25 mg, 50 mg, 75 mg, 100 mg, 250 mg, 500 mg, or ranges including and/or spanning the aforementioned values.

Kits and Methods of Use Thereof

Some embodiments pertain to a kit comprising the imageable radioisotopic particles as disclosed herein.

In some embodiments the kit comprises the underivatized microspheres as described herein and instructions for carrying out the methods described herein to react the imageable radio isotope with the microspheres.

In some embodiments, a kit comprises a microsphere comprising a substrate comprising an inorganic material that comprises metalloid or metal atoms bonded to non-metal atoms, the substrate comprising: a core extending to a surface, the core comprising a first portion of the metalloid or metal atoms bonded to the non-metal atoms and the surface comprising a second portion of the metalloid or metal atoms bonded to the non-metal atoms; and instructions for reacting an imageable radioisotope with the substrate such as to bind the imageable radioisotope directly to the substrate through at least a portion of the non-metal atoms at the surface of the substrate.

In some embodiments, a kit comprises a microsphere comprising: an inorganic substrate; wherein the inorganic substrate comprises at least one non-metal, a metalloid, or a transition metal oxide; and instructions for binding an imageable radioisotope to the surface of the inorganic substrate through a Lewis acid-base coordination bond.

In some embodiments a kit comprises a microsphere comprising a ceramic microsphere substrate and instructions for carrying out a reaction in which an imageable radioisotope is coupled to the ceramic microsphere substrate. In some embodiments the instructions are for carrying out a reaction in which an imageable radioisotope is coupled to the ceramic microsphere substrate as a Lewis acid base adduct.

In some embodiments the kit comprises 50 $\mu$l to 2 ml of microspheres by packed volume, in a sealed unit. In some embodiments the sealed unit may be a container such as a vial, e.g. a glass vial, in other embodiments the sealed unit may be a syringe. The microspheres may be provided sterile.

In some embodiments the kit may additionally comprise a reducing agent.

In some embodiments, the kit comprises instructions for using a catheter to introduce the imageable microsphere into a patient. In some embodiments, the kit comprises therapeutic microspheres. In some embodiments, the kit contains one or more of a vascular access needle, a vascular guidewire, a vascular sheath (e.g., 4-6Fr), a vascular catheter (4-5Fr), a microcatheter, syringes, and a vial.

In some embodiments, an imageable radioisotopic particle Administration Set is acquired. In some embodiments, the set comprises a sterile disposable tubing set and one empty sterile vial. In some embodiments, the tubing set is made of pre-assembled, sterile components and is for single use only. In some embodiments, the pre-assembled tubing set contains a needle plunger assembly and an integrated 20 cc syringe. In some embodiments, the one way valves incorporated in the administration set control the flow of liquid such that it will only flow in the appropriate direction. In some embodiments, the pulling back on the syringe plunger will fill the syringe from the fluid source. In some embodiments, the pushing the syringe plunger will move fluid toward the needle plunger assembly. In some embodiments, prior to the infusion, the Administration Set is manually pre-primed by pushing the sterile flushing solution through the set to purge air from the lines.

In some embodiments, the Administration Accessory Kit is acquired. In some embodiments, the Administration Accessory Kit contains re-usable accessories including one or more of an acrylic box base, top shield, removable side shield and bag hook. In some embodiments, the Administration Accessory Kit facilitates monitoring of the infusion process and provides beta radiation shielding. In some embodiments, the Administration Accessory Kit should be placed on a sturdy cart or table that is positioned beside the patient, close to the infusion catheter inlet luer fitting. In some embodiments, an extension arm on the Accessory Kit facilitates alignment and positioning of the Administration Set/patient catheter connection.

In some embodiments, throughout the administration procedure, an imageable radioisotopic particle dose vial remains sealed within the clear acrylic vial shield in which it is supplied. In some embodiments, the removable plug at the top of the acrylic vial shield provides access to the septum of the imageable radioisotopic particle dose vial. In some embodiments, the needle plunger assembly is designed to snap into the top of the acrylic shield, and is not easily removed once snapped into place. In some embodiments, this provides stability and alignment for the needles which are inserted through the septum when the tabs are pushed down on the plunger assembly.

In some embodiments, the constant syringe pressure should be maintained for the duration of each flush, with a flow rate equal to or greater than 20 cc per minute. One flush is 20 cc as indicated on the barrel of the syringe. In some embodiments, using a flow rate of less than 20 cc per minute (i.e. appropriate to the flow of the native vessel) may decrease the delivery efficiency of the administration system. In some embodiments, flushing should be continued until optimal delivery of imageable radioisotopic particle is achieved. In some embodiments, a minimum of three flushes for a total of 60 cc is recommended. In some embodiments, the infusion pressure should not exceed 30 psi on any flush.

In some embodiments, the pressure relief valve in the Administration Set has been included to prevent over pressurization.

In some embodiments, in order to minimize the potential of a high radiation hand dose, use a hemostat, forceps, or towels/gauze when handling parts of the Administration Set after infusion. In some embodiments, before administration, the acrylic shield containing the dose is measured at a distance of 30 cm from the detector.

Some embodiments provide a sealed unit containing 50 µl to 2 ml of the underivatized microspheres described herein by packed volume. The sealed unit may be a vial or a syringe for example.

In some embodiments the underivatized microspheres comprise a substrate comprising an inorganic material that comprises metalloid or metal atoms bonded to non-metal atoms, the substrate comprising: a core extending to a surface, the core comprising a first portion of the metalloid or metal atoms bonded to the non-metal atoms and the surface comprising a second portion of the metalloid or metal atoms bonded to the non-metal atoms.

In some embodiments the underivatized microspheres comprise a substrate comprising an inorganic material that comprises metalloid or metal atoms bonded to non-metal atoms, the substrate comprising: a core extending to a surface, the core comprising a first portion of the metalloid or metal atoms bonded to the non-metal atoms and the surface comprising a second portion of the metalloid or metal atoms bonded to the non-metal atoms as described herein.

In some embodiments the underivatized microspheres comprise a ceramic microsphere substrate as described herein. The microspheres may be provided sterile.

Enumerated Embodiments

Various example embodiments of particles, microspheres, and methods as disclosed herein can be found in the following non-limiting clauses:

1. An imageable microsphere, comprising:
at least one imageable radioisotope; and a substrate comprising an inorganic material that comprises metalloid or metal atoms bonded to non-metal atoms, the substrate comprising:
a core extending to a surface, the core comprising a first portion of the metalloid or metal atoms bonded to the non-metal atoms and the surface comprising a second portion of the metalloid or metal atoms bonded to the non-metal atoms;
wherein the imageable radioisotope is bound directly to the substrate through at least a portion of the non-metal atoms at the surface of the substrate.

2. An imageable microsphere, comprising:
at least one imageable radioisotope; and a substrate comprising an inorganic material that comprises metalloid or metal atoms bonded to non-metal atoms, the substrate comprising:
a core extending to a surface, the core and the surface comprising metalloid or metal atoms and non-metal atoms of the substrate;
wherein the imageable radioisotope is bound directly to the substrate through non-metal atoms of the surface of the substrate and/or wherein the imageable radioisotope is bound to the substrate through an inorganic bridge comprising non-metal atoms of the surface of the substrate.

3. An imageable microsphere, comprising:
at least one imageable radioisotope; and
a substrate comprising an inorganic material that comprises metalloid or metal atoms bonded to non-metal atoms, the substrate comprising:
a core extending to a surface, the core and the surface comprising metalloid or metal atoms and non-metal atoms of the substrate;
wherein the imageable radioisotope is bound directly to the substrate through non-metal atoms of the surface of the substrate and/or wherein the imageable radioisotope is bound to the substrate through an inorganic bridge comprising non-metal atoms of the surface of the substrate.

4. The imageable microsphere of any one of embodiments 1 to 3, wherein the non-metal atoms are oxygen atoms.

5. The imageable microsphere of embodiment 4, wherein at least a portion of the oxygen atoms at the surface of the substrate are provided as hydroxyl groups.

6. An imageable microsphere, comprising:
an inorganic substrate with a surface layer; and
at least one imageable radioisotope;
wherein the substrate comprises at least one non-metal, a metalloid, or a transition metal oxide; and
wherein the imageable radioisotope is bound to the surface of the substrate by a Lewis acid-base coordination bond.

7. An imageable microsphere, comprising:
an inorganic substrate comprising a surface having one or more electron donating functionalities; and
a surface layer comprising at least one imageable radioisotope;
wherein the imageable radioisotope is bound to the surface of the substrate during preparation of the imageable microsphere via chemical coupling with the one or more electron donating functionalities.

8. The imageable microsphere of any one of embodiments 1 to 7, wherein the imageable radioisotope is bound via a chemical bond selected from an ionic bond, a covalent bond, or a coordinate bond.

9. The imageable microsphere of embodiment 8, wherein the imageable radioisotope is bound via a coordinate bond.

10. An imageable microsphere, comprising:
a ceramic microsphere substrate and at least one imageable radioisotope;
wherein the imageable radioisotope is coupled to the surface of the ceramic microsphere substrate as a Lewis acid-base adduct.

11. An imageable microsphere, comprising:
at least one imageable radioisotope; and
a substrate comprising an inorganic material that comprises metalloid or metal atoms bonded to non-metal atoms, the substrate comprising:
a core extending to a surface, the core comprising a first portion of the metalloid or metal atoms bonded to the non-metal atoms and the surface comprising a second portion of the metalloid or metal atoms bonded to the non-metal atoms;
wherein the imageable radioisotope is bound directly to the substrate through non-metal atoms of the surface of the substrate and/or wherein the imageable radioisotope is bound to the substrate through an inorganic bridge comprising non-metal atoms of the surface of the substrate.

12. The imageable microsphere of embodiment 1 to 11, wherein the imageable radioisotope is bound directly to the substrate through non-metal atoms of the surface of the substrate.

13. The imageable microsphere of embodiment 1 to 12, wherein the substrate is bound to the substrate through an inorganic bridge through non-metal atoms of the surface of the substrate.

14. The imageable microsphere of any one of embodiments 1 to 13, wherein the substrate comprises a substantially homogeneous mixture of constituent chemical elements.

15. The imageable microsphere of embodiment 14, wherein the surface comprises at least a portion of the constituent chemical elements.

16. The imageable microsphere of any one of embodiments 1 to 15, wherein the non-metal atoms are oxygen atoms.

17. The imageable microsphere of embodiment 16, wherein at least a portion of the oxygen atoms at the surface of the substrate are hydroxyl groups.

18. An imageable microsphere, comprising:
an inorganic substrate with a surface; and
at least one imageable radioisotope;
wherein the substrate comprises at least one non-metal and at least a metalloid or a metal; and
wherein the imageable radioisotope is bound to the surface of the substrate by a Lewis acid-base coordination bond to an inorganic Lewis base.

19. An imageable microsphere, comprising:
an inorganic substrate having a surface; and
at least one imageable radioisotope;
wherein the substrate comprises at least one non-metal and at least a metalloid or a metal; and
wherein the imageable radioisotope is bound to the surface of the substrate by a chemical bond to an oxygen of an inorganic species.

20. An imageable microsphere, comprising:
an inorganic substrate comprising a surface having one or more electron donating functionalities; and
at least one imageable radioisotope;
wherein the imageable radioisotope is bound directly to the surface and/or is bound to the surface through an inorganic bridge during preparation of the imageable microsphere via chemical coupling with the one or more electron donating functionalities.

21. The imageable microsphere of embodiment 20, wherein the imageable radioisotope is bound directly to the surface of the substrate.

22. The imageable microsphere of any one of embodiments 1 to 21, wherein the substrate comprises a metal oxide, a transition metal oxide, a metalloid oxide, or combinations thereof.

23. The imageable microsphere of any one of embodiments 1 to 22, wherein the imageable radioisotope is bound to the substrate via a chemical bond selected from an ionic bond, a covalent bond, or a coordinate bond.

24. The imageable microsphere of embodiment 23, wherein the imageable radioisotope is bound via a coordinate bond.

25. An imageable microsphere, comprising:
a ceramic microsphere substrate and at least one imageable radioisotope;
wherein the imageable radioisotope is coupled to the surface of the ceramic microsphere substrate as a Lewis acid-base adduct of an inorganic Lewis base.

26. The imageable microsphere of embodiment 25, wherein the inorganic Lewis base is a component of the substrate and the imageable isotope is directly coupled to the substrate surface through the inorganic Lewis base.

27. The imageable microsphere of embodiment 26, wherein the imageable radioisotope is coupled to the surface of the ceramic microsphere substrate through an inorganic linker comprising the Lewis base.

28. The imageable microsphere of embodiment 27, wherein the inorganic linker is a metal oxide.

29. The imageable microsphere of embodiment 28, wherein the metal oxide is a tin oxide.

30. The imageable microsphere of any of embodiments 25 to 29, wherein the Lewis base is an oxygen of a metal oxide or metalloid oxide.

31. The imageable microsphere of any one of embodiments 18 to 30, wherein the Lewis base is the oxygen of a tin oxide.

32. The imageable microsphere of any one of embodiments 1 to 31, wherein the imageable isotope is configured for imaging by an imaging modality selected from single photon imaging and double photon imaging.

33. The imageable microsphere of any one of embodiments 1 to 32, wherein the imageable radioisotope is configured for imaging by an imaging modality selected from positron emission tomography (PET), single photon emission computed tomography (SPECT), and gamma camera imaging.

34. The imageable microsphere of any one of embodiments 1 to 33, wherein the at least one imageable radioisotope is a positron emitter or a gamma emitter.

35. The imageable microsphere of any one of embodiments 1 to 34, wherein the at least one imageable radioisotope is a metallic radioisotope.

36. The imageable microsphere of any one of embodiments 1 to 34, wherein the at least one imageable radioisotope is selected from $^{99m}Tc$, $^{201}Th$, $^{51}Cr$, $^{67}Ga$, $^{68}Ga$, $^{111}In$, $^{64}CU$, $^{89}Zr$, $^{59}Fe$, $^{42}K$, $^{82}Rb$, $^{24}Na$, $^{45}Ti$, $^{4}Sc$, $^{51}Cr$, $^{18}F$, $^{177}Lu$, $Al^{18}F$, and/or combinations thereof.

37. The imageable microsphere of any one of embodiments 1 to 34, wherein the at least one imageable radioisotope is selected from 99mTc and 89Zr.

38. The imageable microsphere of any one of embodiments 1 to 34, comprising a structure of Formula (V):
where

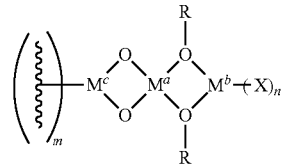

the substrate comprises $M^c$ and $M^c$ is selected from Pb, Al, Si, Y, Mn, Ga, Fe, Sr, and Ti;

m is an integer selected from 1, 2, or 3;

$M^b$ is selected from $^{99m}Tc$, $^{201}Th$, $^{51}Cr$, $^{67}Ga$, $^{68}Ga$, $^{111}In$, $^{64}Cu$, $^{89}Zr$, $^{59}Fe$, $^{42}K$, $^{82}Rb$, $^{24}Na$, $^{45}Ti$, $^{4}Sc$, $^{51}Cr$, $^{18}F$, $^{177}Lu$, $Al^{18}F$, and/or combinations thereof;

$M^a$ is either an atom of the substrate or a bridging metal atom and $M^a$ is selected from Sn, Pb, Al, Si, Y, Mn, Ga, Fe, Sr, and Ti;

each instance of R is not present or is —H;

X is selected from —OH, =O, and —O$^-$; and n is an integer selected from 0, 1, 2, 3, or 4.

39. The imageable microsphere of embodiment 38, wherein:
$M^c$ is Al;
the substrate comprises $M^a$ and $M^a$ is Si;
$M^b$ is $^{89}$Zr;
each X is independently —OH or —O$^-$; and
n is 1 or 2.

40. The imageable microsphere of embodiment 38 or 39, wherein $M^b$ is $^{89}$Zr, X is —OH, and n is 2.

41. The imageable microsphere of embodiment 38, wherein:
$M^c$ is Si;
$M^a$ is Sn;
$M^b$ is $^{99m}$Tc;
each X is independently —OH or —O$^-$; and
n is 2 or 3.

42. The imageable microsphere of embodiment 38, wherein $M^b$ is $^{99m}$Tc, X is —OH, and n is 3.

43. The imageable microsphere of any one of embodiments 1. to 34, comprising a structure of Formula (VIII):

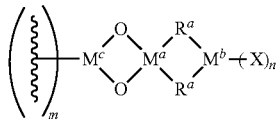

(VIII)

where the substrate comprises $M^a$ and $M^c$ and where $M^a$ and $M^c$ are independently selected from Pb, Al, Si, Y, Mn, Ga, Fe, and Ti;
m is an integer selected from 1, 2, or 3;
$M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof;
each instance of $R^a$ is independently OH, O, or —O—Sn$(X)_n$—O$^-$;
X is selected from —OH, =O, and —O$^-$; and
n is an integer selected from 0, 1, 2, 3, or 4.

44. The imageable microsphere of embodiment 43, wherein M is Al; $M^a$ is Si; $M^b$ is $^{99m}$Tc; each X is independently —OH or =O; and n is 2 or 3.

45. The imageable microsphere of embodiment 43, wherein $M^b$ is $^{99m}$Tc; at least an instance of $R^a$ is —O—Sn$(X)_n$—O—, each X is independently —OH or =O; and n is 2 or 3.

46. The imageable microsphere of embodiment 43, wherein $M^b$ is $^{99m}$Tc; an instance of $R^a$ is —O—Sn—O—; an instance of $R^a$ is —O— or —OH—; each X is independently —OH or =O; and n is 2 or 3.

47. The imageable microsphere of any one of embodiments 1 to 46, wherein the substrate comprises at least one non-metal and a metalloid, a transition metal, and a metal.

48. The imageable microsphere of any one of embodiments 1 to 47, wherein the substrate comprises a ceramic material.

49. The imageable microsphere of embodiment 48, wherein the ceramic comprises at least one element selected from silicon, yttrium, manganese, aluminium, gallium, and titanium.

50. The imageable microsphere of any one of embodiments 1 to 49, wherein the substrate comprises glass.

51. The imageable microsphere of any one of embodiments 1 to 50, wherein the substrate comprises silicon dioxide and at least one other element selected from manganese, aluminium, gallium, yttrium, boron and titanium.

52. The imageable microsphere of any one of embodiments 1 to 51, wherein the substrate comprises $SiO_2$, $Y_2O_3$, $MnO_2$, $AlO_3$, $Ga_2O_3$, $Fe_2O_3$, $TiO_2$, $SrCO_3$, $SrO_2$, or combinations thereof.

53. The imageable microsphere of any one of embodiments 1 to 52, wherein the substrate comprises $SiO_2$ and at least one of $Y_2O_3$, $MnO_2$, $AlO_3$, $Ga_2O_3$, $Fe_2O_3$, $TiO_2$, $SrCO_3$, and $SrO_2$.

54. The imageable microsphere of any of embodiments 1 to 53, wherein the substrate comprises an yttrium aluminum silicon oxide.

55. The imageable microsphere of any one of embodiments 1 to 54, wherein the imageable microsphere lacks a therapeutic radioisotope.

56. The imageable microsphere of any one of embodiments 1 to 55, wherein the imageable microsphere has a diameter of between 5 μm and 1000 μm.

57. The imageable microsphere of any one of embodiments 1 to 56, wherein the substrate is non-porous.

58. The imageable microsphere of any one of embodiments 1 to 56, wherein the substrate is porous.

59. The imageable microsphere of any one of embodiments 1 to 58 made by a method comprising:
providing the substrate;
chemically coupling the at least one imageable radioisotope to the substrate to provide the imageable microsphere.

60. A imageable microsphere made by a method comprising:
providing a substrate comprising:
an inorganic material comprising metal or metalloid atoms bonded to non-metal atoms;
a core comprising a first portion of the non-metal atoms; and
a surface comprising a second portion of the non-metal atoms;
providing at least one imageable radioisotope; and
chemically coupling the at least one imageable radioisotope to the surface of the substrate through the second portion of non-metal atoms to provide the imageable microsphere.

61. The imageable microsphere of embodiments 59 or 60, further comprising providing the at least one imageable radioisotope as a salt prior to chemically coupling the at least one imageable radioisotope to the surface layer of the inorganic substrate.

62. The imageable microsphere of embodiment 61, wherein the salt is an alkali metal salt, an alkali earth metal salt, a halogen salt, a polyatomic salt, or a salt with an organic acid.

63. The imageable microsphere of embodiment of 59 to 62, wherein the chemical functionalization is carried out in the presence of a reducing agent.

64. The imageable microsphere of embodiment 63, wherein the reducing agent is selected from one or more of a stannous salt, a stannous hydrate, concentrated HCl, sodium borohydride, sodium dithionite, ferrous sulfate, ferric chloride plus ascorbic acid, hypophosphorous acid, and/or hydrazine.

65. The imageable microsphere of embodiment of 59 to 63, wherein the radioisotope is $^{99m}$Tc and the chemical functionalization is carried out in the presence of a tin salt.

66. The imageable microsphere of embodiment of 65, wherein the radioisotope is provided in the form of $^{99m}$Tc pertechnetate and the chemical functionalization is carried out in the presence of stannous ions.

67. The imageable microsphere of embodiment of 59 to 62, wherein the $^{89}$Zr is provided in the form of $^{89}$Zr oxalate.

68. The imageable microsphere of embodiment of 67, wherein the $^{89}$Zr is provided in the form of $^{89}$Zr oxalate.

69. A method for preparing an imageable microsphere, comprising providing a ceramic microsphere substrate and reacting the ceramic microsphere substrate with an imageable radioisotope under conditions suitable to couple the radioisotope to the surface of the ceramic microsphere.

70. A method according to embodiment 69, wherein the radioisotope is coupled to the surface of the ceramic microsphere in the form of a Lewis acid-base adduct.

71. A method according to embodiments 69 or 70, wherein the radioisotope is a metallic radio isotope.

72. A method according to any of embodiments 59 to 61, wherein the radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, Al$^{18}$F and/or combinations thereof.

73. A method according to any of embodiments 69 to 72, wherein the radioisotope is provided in the form of a salt.

74. A method according to any of embodiments 69 to 73, wherein the radioisotope is reacted with the ceramic microsphere in the presence of a reducing agent.

75. A method according to embodiment 74, wherein the reducing agent is selected from one or more of a stannous salt, a stannous hydrate, HCl, sodium borohydride, sodium dithionite, ferrous sulfate, ferric chloride plus ascorbic acid, hypophosphorous acid, and/or hydrazine.

76. A method according to any of embodiments 69 to 75, wherein the radioisotope is $^{99m}$Tc.

77. A method according to embodiment 76, wherein the $^{99m}$Tc is provided in the form of a pertechnetate salt.

78. A method according to embodiment 76, wherein the $^{99m}$Tc is provided in the form of a pertechnetate salt and the reaction is carried out in the presence of stannous ions.

79. A method according to any of embodiments 69 to 75, wherein the radioisotope is $^{89}$Zr.

80. A method according to embodiment 79, wherein the 89Zr is provided in the form of $^{89}$Zr oxalate.

81. A method according to embodiment 79 or 80, wherein the reaction is carried out in the presence of a base.

82. A method of making the imageable microsphere of any one of embodiments 1 to 68, the method comprising:
providing the inorganic substrate; and
chemically functionalizing the inorganic substrate with the at least one imageable radioisotope to provide the imageable microsphere.

83. The method of embodiment 82, further comprising providing the at least one imageable radioisotope as a salt prior to chemically functionalizing the at least one imageable radioisotope to a surface of the inorganic substrate.

84. The method of embodiment 83, wherein the salt is an alkali metal salt, an alkali earth metal salt, a halogen salt, a polyatomic salt, or a salt with an organic acid.

85. The method of embodiment 83 or 84, further comprising adding a reducing agent during the chemical functionalization step.

86. The method of embodiment 85, wherein the reducing agent is selected from one or more of a stannous salt, a stannous hydrate, HCl, sodium borohydride, sodium dithionite, ferrous sulfate, ferric chloride plus ascorbic acid, hypophosphorous acid, and/or hydrazine.

87. A method according to any of embodiments 82 to 86, wherein the radioisotope is $^{99m}$Tc.

88. A method according to embodiment 87, wherein the $^{99m}$Tc is provided in the form of a pertechnetate salt.

89. A method according to embodiment 87, wherein the $^{99m}$Tc is provided in the form of a pertechnetate salt and the reaction is carried out in the presence of stannous ions.

90. A method according to any of embodiments 82 to 89, wherein the radioisotope is $^{89}$Zr.

91. A method according to embodiment 90, wherein the $^{89}$Zr is provided in the form of $^{89}$Zr oxalate.

92. A method according to embodiment 90 or 91, wherein the reaction is carried out in the presence of a base.

93. A method according to any one of embodiments 69 to 92, carried out in aqueous conditions.

94. A method according to any one of embodiments 69 to 93, additionally comprising recovering the imageable microsphere and/or washing the microsphere to remove unreacted radioisotope.

95. A method according to any of embodiments 69 to 94, additionally comprising resuspending the imageable microsphere in a pharmaceutically acceptable injectable aqueous medium.

96. An imageable microsphere obtainable by a method according to any of embodiments 69 to 95.

97. A method for determining an amount of therapeutic microspheres to provide to a body of a patient, the method comprising:
providing a population of imageable microspheres;
delivering the population of imageable microspheres to the patient by introducing the population of imageable microspheres to a first position in a vasculature of the patient;
allowing the population of imageable microspheres to distribute within the body of the patient;
determining a distribution of at least a portion of the population of the imageable microspheres within the body of the patient by imaging a portion of the body of the patient using an imaging modality; and
using the distribution of the imageable microspheres to calculate an amount of therapeutic microspheres to be delivered to the body of the patient.

98. The method of embodiment 97, wherein the portion of the body is an off-target area of the patient and the off-target area is a lung of the patient.

99. The method of embodiment 97, wherein the portion of the body is a target area of the patient and the target area is a liver of the patient.

100. The method of any one of embodiments 97 to 99, wherein the target area is divided into tumor and non-tumor tissue.

101. The method of one of embodiments 97 to 100, wherein an amount of therapeutic microspheres to be delivered to the patient is calculated.

102. The method of embodiment 91, wherein the amount calculated is delivered to the patient.

103. The method of any one of embodiments 97 to 102, wherein the imaging modality is SPECT.

104. The method of any one of embodiments 97 to 102, wherein the detection modality is PET.

105. The method of any one of embodiments 97 to 102, wherein the detection modality is gamma camera imaging.

106. The method of any one of embodiments 97 to 102, wherein the imageable microspheres are the imageable microspheres of any one of embodiments 1 to 68.

107. A method for treating a patient, the method comprising:
providing a population of imageable microspheres;
delivering the population of imageable microspheres to the patient by introducing the population of imageable microspheres to a first position in a vasculature of a body of the patient;
allowing the population of imageable microspheres to distribute within the body of the patient;
determining a distribution of at least a portion of the population of the imageable microspheres within the body of the patient by imaging a target section of the body of the patient using an imaging modality; and
using the distribution of the imageable microspheres to calculate an amount of therapeutic microspheres to be delivered to the body of the patient;
obtaining data regarding a distribution of an imageable therapeutic microsphere surrogate in a patient;
using the data to determine a dose of a therapeutic amount of microspheres to administer to the body of the patient;
delivering a population of therapeutic microspheres to the patient by introducing the population of therapeutic microspheres to a second position in the vasculature of the body of the patient;
allowing the population of therapeutic microspheres to distribute within the body of the patient, thereby treating the patient.

108. The method of embodiment 107, wherein the second position in the vasculature of the patient is the same as the first position in the vasculature of the patient.

109. The method of embodiment 107 or 108, wherein the imaging modality is SPECT.

110. The method of embodiment 107 or 108, wherein the detection modality is PET.

111. The method of embodiment 107 or 108, wherein the detection modality is a gamma camera imaging.

112. The method of any one of embodiments 107 or 111, wherein the imageable microspheres are the imageable microspheres of any one of embodiments 1 to 68.

113. A method for treating a patient with therapeutic microspheres, the method comprising:
obtaining data calculated from the distribution of an imageable therapeutic microsphere surrogate in a patient;
using the data to determine an amount of therapeutic microspheres to be dosed to a body of the patient;
delivering the amount of therapeutic microspheres to the patient by introducing the amount of therapeutic microspheres to a first position in a vasculature of the patient;
allowing the therapeutic microspheres to distribute within the body of the patient; and
allowing the therapeutic microspheres to reside in the body of the patient, thereby treating the patient.

114. The method of embodiment 113, further comprising providing a population of imageable microspheres to the patient.

115. The method of embodiment 114, further comprising delivering the population of imageable microspheres to the patient by introducing the population of imageable microspheres to the first position in the vasculature of the body of the patient.

116. The method of embodiment 115, further comprising allowing the population of imageable microspheres to distribute within the body of the patient.

117. The method of embodiment 116, further comprising determining a distribution of at least a portion of the population of the imageable microspheres within the body of the patient by imaging a target section of the body of the patient using an imaging modality; and 118. The method of embodiment 117, further comprising using the distribution of the imageable microspheres to calculate the amount of therapeutic microspheres to be delivered to the body of the patient.

119. A method of treating a tumor in a patient in need of treatment, the method comprising:
introducing a population of imageable microspheres to the patient;
allowing the imageable microspheres to distribute within the patient over a period of time;
determining the distribution of the imageable microspheres at a site within the patient by imaging the imageable microspheres using an imaging modality;
determining an estimated effective dose at the site based on the distribution of the imageable microspheres had the imageable microspheres been replaced by therapeutic microspheres; and
administering an amount of the therapeutic microspheres to the patient based on the estimated effective dose.

120. The method of embodiment 119, wherein the population of imageable microspheres comprises the imageable microsphere of any one of embodiments 1 to 68.

121. The method of embodiment 119 or 120, wherein the site is a malignant or benign tumor and/or a non-tumorous tissue.

122. The method of embodiment 119 or 120, wherein the site is a malignant tumor.

123. The method of embodiment 122, wherein the site is a malignant tumor.

124. A method of predicting the degree of off-target delivery to the lung or the gastrointestinal tract during treatment of a patient in need of radioisotopic cancer treatment, the method comprising:
introducing a population of imageable microspheres to the patient;
allowing the imageable microspheres to distribute within the patient over a period of time;
determining the distribution of the imageable microspheres within a lung of the patient by imaging the imageable microspheres using an imaging modality;
determining an estimated dose of radiation in the lung or gastrointestinal tract respectively of the patient if the imageable microspheres had been replaced by radioisotopic therapeutic microspheres;
determining a dose of the radioisotopic therapeutic microspheres that is sufficient to cause clinically relevant lung or gastro intestinal changes due to off-target delivery; and
administering a dose of the radioisotopic therapeutic microspheres to a patient that is below the dose of the radioisotopic therapeutic microspheres determined to be sufficient to cause clinically relevant lung or gastrointestinal changes due to off-target delivery.

125. The method of embodiment 124, wherein the population of imageable microspheres comprises the imageable microsphere of any one of embodiments 1 to 68.

126. A method of reducing lung or gastrointestinal damage during treatment of a patient in need of radioisotopic cancer treatment, the method comprising:
introducing a population of imageable microspheres to the patient;
allowing the imageable microspheres to distribute within the patient over a period of time;

determining the distribution of the imageable microspheres within a gastrointestinal tract or lung of the patient by imaging the imageable microspheres using an imaging modality;

determining an estimated dose of radiation in the gastrointestinal tract or lung of the patient if the imageable microspheres had been replaced by radioisotopic therapeutic microspheres;

determining a dose of the radioisotopic therapeutic microspheres that is sufficient to cause gastrointestinal tract damage; and administering a dose of the radioisotopic therapeutic microspheres to the patient that is below the dose of the radioisotopic therapeutic microspheres determined to be sufficient to cause damage gastrointestinal tract.

127. The method of embodiment 126, wherein the population of imageable microspheres comprises the imageable microsphere of any one of embodiments 1 to 68.

128. A kit comprising:
a microsphere comprising:
a substrate comprising an inorganic material that comprises metalloid or metal atoms bonded to non-metal atoms, the substrate comprising:
a core extending to a surface, the core comprising a first portion of the metalloid or metal atoms bonded to the non-metal atoms and the surface comprising a second portion of the metalloid or metal atoms bonded to the non-metal atoms; and
instructions for reacting an imageable radioisotope with the substrate such as to bind the imageable radioisotope directly to the substrate through at least a portion of the non-metal atoms at the surface of the substrate.

129. A kit comprising
a microsphere comprising:
an inorganic substrate; wherein the inorganic substrate comprises at least one non-metal, a metalloid, or a transition metal oxide; and
instructions for binding an imageable radioisotope to the surface of the inorganic substrate through a Lewis acid-base coordination bond.

130. A kit comprising a microsphere comprising a ceramic microsphere substrate and instructions for carrying out a reaction in which an imageable radioisotope is coupled to the ceramic microsphere substrate as a Lewis acid base adduct.

131. A kit according to any of embodiments 128 to 130, comprising 10 µl to 2 ml of microspheres by packed volume, in a sealed unit.

132. A kit of any one of embodiments 128 to 131, wherein the microspheres are provided in a vial or a syringe.

133. A kit according to any of embodiments 128 to 132, wherein the imageable radioisotope is selected from one or more of $^{99m}$Tc, $^{201}$Th, $^{51}$Cr, $^{67}$Ga, $^{68}$Ga, $^{111}$In, $^{64}$Cu $^{89}$Zr, $^{59}$Fe, $^{42}$K, $^{82}$Rb, $^{24}$Na, $^{45}$Ti, $^{44}$Sc, $^{51}$Cr, $^{18}$F, Al$^{18}$F.

134. A kit according to any of embodiments 128 to 133, which additionally comprises a reducing agent.

135. A kit according to embodiment 134, wherein the reducing agent is selected from one or more of a stannous salt, a stannous hydrate, concentrated HCl, sodium borohydride, sodium dithionite, ferrous sulfate, ferric chloride plus ascorbic acid, hypophosphorous acid, and/or hydrazine.

136. A kit according to embodiments 134 or 135, wherein the reducing agent is a stannous salt, the radioisotope is $^{99m}$Tc and the radioisotope is in the form of a pertechnetate salt.

137. A kit according to any one of embodiments 128 to 133, wherein the radioisotope is $^{89}$Zr.

138. A kit according to embodiment 137, wherein the radioisotope is in the form of $^{89}$Zr zirconium oxalate or zirconium chloride 139. The kit of any one of embodiments 128 to 138, further comprising therapeutic microspheres.

140. The kit of embodiment 139, wherein the therapeutic microspheres comprise a therapeutic radioisotope.

141. The kit of embodiment 140, wherein the therapeutic microspheres comprise $^{90}$Y, $^{166}$Ho, $^{177}$Lu, $^{131}$I, $^{89}$Sr, $^{153}$Sm, $^{223}$Ra, $^{224}$Ra, $^{211}$At, $^{225}$Ac, $^{227}$Th, $^{212}$Bi, $^{213}$Bi, and/or $^{212}$Pb.

142. The kit of any one of embodiments 139 to 141, wherein the therapeutic microspheres are of the same chemical composition as the imageable microspheres.

143. The kit of any one of embodiments 139 to 142, wherein the therapeutic microspheres comprise an yttrium aluminum silicon oxide.

144. The kit of any one of embodiments 128 to 143, further comprising one or more of a vascular access needle, a vascular guidewire, a vascular sheath (e.g., 4-6Fr), a vascular catheter (4-5Fr), a microcatheter, syringes, and a vial.

145. An imageable microsphere, comprising:
at least one imageable radioisotope; and
a substrate comprising an inorganic material that comprises metalloid or metal atoms bonded to non-metal atoms, the substrate comprising:
a core extending to a surface, the core comprising a first portion of the metalloid or metal atoms bonded to the non-metal atoms and the surface comprising a second portion of the metalloid or metal atoms bonded to the non-metal atoms;
wherein the imageable radioisotope is bound directly to the substrate through non-metal atoms of the surface of the substrate and/or wherein the imageable radioisotope is bound to the substrate through an inorganic bridge comprising non-metal atoms of the surface of the substrate.

146. The imageable microsphere of embodiment 145, wherein the imageable radioisotope is bound directly to the substrate through non-metal atoms of the surface of the substrate.

147. The imageable microsphere of embodiment 145 or 146, wherein the substrate is bound to the substrate through an inorganic bridge through non-metal atoms of the surface of the substrate.

148. The imageable microsphere of any one of embodiments 145 to 147, wherein the substrate comprises a substantially homogeneous mixture of constituent chemical elements.

149. The imageable microsphere of embodiment 148, wherein the surface comprises at least a portion of the constituent chemical elements.

150. The imageable microsphere of any one of embodiments 145 to 149, wherein the non-metal atoms are oxygen atoms.

151. The imageable microsphere of embodiment 150, wherein at least a portion of the oxygen atoms at the surface of the substrate are hydroxyl groups.

152. An imageable microsphere, comprising:
an inorganic substrate with a surface; and
at least one imageable radioisotope;
wherein the substrate comprises at least one non-metal and at least a metalloid or a metal; and
wherein the imageable radioisotope is bound to the surface of the substrate by a Lewis acid-base coordination bond to an inorganic Lewis base.

153. An imageable microsphere, comprising:
an inorganic substrate having a surface; and
at least one imageable radioisotope;
wherein the substrate comprises at least one non-metal and at least a metalloid or a metal; and
wherein the imageable radioisotope is bound to the surface of the substrate by a chemical bond to an oxygen of an inorganic species.

154. An imageable microsphere, comprising:
an inorganic substrate comprising a surface having one or more electron donating functionalities; and
at least one imageable radioisotope;
wherein the imageable radioisotope is bound directly to the surface and/or is bound to the surface through an inorganic bridge during preparation of the imageable microsphere via chemical coupling with the one or more electron donating functionalities.

155. The imageable microsphere of embodiment 154, wherein the imageable radioisotope is bound directly to the surface of the substrate.

156. The imageable microsphere of any one of embodiments 145 to 155, wherein the substrate comprises a metal oxide, a transition metal oxide, a metalloid oxide, or combinations thereof.

157. The imageable microsphere of any one of embodiments 145 to 156, wherein the imageable radioisotope is bound to the substrate via a chemical bond selected from an ionic bond, a covalent bond, or a coordinate bond.

158. The imageable microsphere of embodiment 157, wherein the imageable radioisotope is bound via a coordinate bond.

159. An imageable microsphere, comprising:
a ceramic microsphere substrate and at least one imageable radioisotope;
wherein the imageable radioisotope is coupled to the surface of the ceramic microsphere substrate as a Lewis acid-base adduct of an inorganic Lewis base.

160. The imageable microsphere of embodiment 159, wherein the inorganic Lewis base is a component of the substrate and the imageable isotope is directly coupled to the substrate surface through the inorganic Lewis base.

161. The imageable microsphere of any one of embodiments 159 to 160, wherein the imageable radioisotope is coupled to the surface of the ceramic microsphere substrate through an inorganic linker comprising the Lewis base.

162. The imageable microsphere of embodiment 161, wherein the inorganic linker is a metal oxide.

163. The imageable microsphere of embodiment 162, wherein the metal oxide is a tin oxide.

164. The imageable microsphere of any of embodiments 159 to 163, wherein the Lewis base is an oxygen of a metal oxide or metalloid oxide.

165. The imageable microsphere of any one of embodiments 152 to 164, wherein the Lewis base is the oxygen of a tin oxide.

166. The imageable microsphere of any one of embodiments 145 to 165, wherein the imageable isotope is configured for imaging by an imaging modality selected from single photon imaging and double photon imaging.

167. The imageable microsphere of any one of embodiments 145 to 166, wherein the imageable radioisotope is configured for imaging by an imaging modality selected from positron emission tomography (PET), single photon emission computed tomography (SPECT), and gamma camera imaging.

168. The imageable microsphere of any one of embodiments 145 to 167, wherein the at least one imageable radioisotope is a positron emitter or a gamma emitter.

169. The imageable microsphere of any one of embodiments 145 to 168, wherein the at least one imageable radioisotope is a metallic radioisotope.

170. The imageable microsphere of any one of embodiments 145 to 168, wherein the at least one imageable radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, Al$^{18}$F, and/or combinations thereof.

171. The imageable microsphere of any one of embodiments 145 to 168, wherein the at least one imageable radioisotope is selected from $^{99m}$Tc and $^{89}$Zr.

172. The imageable microsphere of any one of embodiments 145 to 168, comprising a structure of Formula (V):

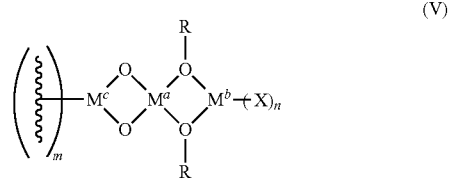

(V)

where
the substrate comprises $M^c$ and $M^c$ is selected from Pb, Al, Si, Y, Mn, Ga, Fe, Sr, and Ti;
m is an integer selected from 1, 2, or 3;
$M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, $^{177}$Lu, Al$^{18}$F, and/or combinations thereof;
$M^a$ is either an atom of the substrate or a bridging metal atom and $M^a$ is selected from Sn, Pb, Al, Si, Y, Mn, Ga, Fe, Sr, and Ti;
each instance of R is not present or is —H;
X is selected from —OH, =O, and —O⁻; and
n is an integer selected from 0, 1, 2, 3, or 4.

173. The imageable microsphere of embodiment 172, wherein:
$M^c$ is Al;
the substrate comprises $M^a$ and $M^a$ is Si;
$M^b$ is $^{89}$Zr;
each X is independently —OH or —O⁻; and
n is 1 or 2.

174. The imageable microsphere of embodiment 172 or 173, wherein $M^b$ is $^{89}$Zr, X is —OH, and n is 2.

175. The imageable microsphere of embodiment 172, wherein:
$M^c$ is Si;
$M^a$ is Sn;
$M^b$ is $^{99m}$Tc;
each X is independently —OH or —O⁻;
and n is 2 or 3.

176. The imageable microsphere of embodiment 172, wherein $M^b$ is $^{99m}$Tc, X is —OH, and n is 3.

177. The imageable microsphere of any one of embodiments 145 to 168, comprising a structure of Formula (VIII):

(VIII)

where the substrate comprises $M^a$ and $M^c$ and where $M^a$ and $M^c$ are independently selected from Pb, Al, Si, Y, Mn, Ga, Fe, Sr, and Ti;
m is an integer selected from 1, 2, or 3; $M^b$ is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{177}$Lu, Al$^{18}$F, and/or combinations thereof;

each instance of R$^a$ is independently OH, O, or —O—Sn(X)$_n$—O—;

X is selected from —OH, =O, and —O$^-$; and n is an integer selected from 0, 1, 2, 3, or 4.

178. The imageable microsphere of embodiment 177, wherein M$^c$ is Al; M$^a$ is Si; M$^b$ is $^{99m}$Tc; each X is independently —OH or =O; and n is 2 or 3.

179. The imageable microsphere of embodiment 177, wherein M$^b$ is $^{99m}$Tc; at least an instance of R$^a$ is —O—Sn(X)$_n$—O—, each X is independently —OH or =O; and n is 2 or 3.

180. The imageable microsphere of embodiment 177, wherein M$^b$ is $^{99m}$Tc; an instance of R$^a$ is —O—Sn—O—; an instance of R$^a$ is —O— or —OH—; each X is independently —OH or =O; and n is 2 or 3.

181. The imageable microsphere of any one of embodiments 145 to 180, wherein the substrate comprises at least one non-metal and a metalloid, a transition metal, and a metal.

182. The imageable microsphere of any one of embodiments 145 to 181, wherein the substrate comprises a ceramic material.

183. The imageable microsphere of embodiment 182, wherein the ceramic comprises at least one element selected from silicon, yttrium, manganese, aluminium, gallium, and titanium.

184. The imageable microsphere of any one of embodiments 145 to 183 or of 182, wherein the substrate comprises glass.

185. The imageable microsphere of any one of embodiments 145 to 184, wherein the substrate comprises silicon dioxide and at least one other element selected from manganese, aluminium, gallium, yttrium, boron and titanium.

186. The imageable microsphere of any one of embodiments 145 to 185, wherein the substrate comprises SiO$_2$, Y$_2$O$_3$, MnO$_2$, AlO$_3$, Ga$_2$O$_3$, Fe$_2$O$_3$, TiO$_2$, SrO$_2$, SrCO$_3$, or combinations thereof.

187. The imageable microsphere of any one of embodiments 145 to 186, wherein the substrate comprises SiO$_2$ and at least one of Y$_2$O$_3$, MnO$_2$, AlO$_3$, Ga$_2$O$_3$, Fe$_2$O$_3$, TiO$_2$, SrCO$_3$, and SrO$_2$.

188. The imageable microsphere of any of embodiments 145 to 187, wherein the substrate comprises an yttrium aluminum silicon oxide.

189. The imageable microsphere of any one of embodiments 145 to 188, wherein the imageable microsphere lacks a therapeutic radioisotope.

190. The imageable microsphere of any one of embodiments 145 to 189, wherein the imageable microsphere has a diameter of between 5 μm and 1000 μm.

191. The imageable microsphere of any one of embodiments 145 to 190, wherein the substrate is non-porous.

192. The imageable microsphere of any one of embodiments 145 to 190, wherein the substrate is porous.

193. The imageable microsphere of any one of embodiments 145 to 192 made by a method comprising:
providing the substrate;
chemically coupling the at least one imageable radioisotope to the substrate to provide the imageable microsphere.

194. A imageable microsphere made by a method comprising:
providing a substrate comprising:
an inorganic material comprising metal or metalloid atoms bonded to non-metal atoms;
a core comprising a first portion of the non-metal atoms; and
a surface comprising a second portion of the non-metal atoms;
providing at least one imageable radioisotope; and
chemically coupling the at least one imageable radioisotope to the surface of the substrate through the second portion of non-metal atoms to provide the imageable microsphere.

195. The imageable microsphere of embodiments 193 or 194, further comprising providing the at least one imageable radioisotope as a salt prior to chemically coupling the at least one imageable radioisotope to the surface layer of the inorganic substrate.

196. The imageable microsphere of embodiment 195, wherein the salt is an alkali metal salt, an alkali earth metal salt, a halogen salt, a polyatomic salt, or a salt with an organic acid.

197. The imageable microsphere of embodiment of 193 to 196, wherein the chemical functionalization is carried out in the presence of a reducing agent.

198. The imageable microsphere of embodiment 197, wherein the reducing agent is selected from one or more of a stannous salt, a stannous hydrate, concentrated HCl, sodium borohydride, sodium dithionite, ferrous sulfate, ferric chloride plus ascorbic acid, hypophosphorous acid, and/or hydrazine.

199. The imageable microsphere of embodiment of 193 to 197, wherein the radioisotope is $^{99m}$Tc and the chemical functionalization is carried out in the presence of a tin salt.

200. The imageable microsphere of embodiment of 199, wherein the radioisotope is provided in the form of $^{99m}$Tc pertechnetate and the chemical functionalization is carried out in the presence of stannous ions.

201. The imageable microsphere of embodiment of 193 to 196, wherein the radioisotope is $^{89}$Zr.

202. The imageable microsphere of embodiment of 201, wherein the $^{89}$Zr is provided in the form of $^{89}$Zr oxalate.

203. A method for preparing an imageable microsphere, comprising providing a ceramic microsphere substrate and reacting the ceramic microsphere substrate with an imageable radioisotope under conditions suitable to couple the radioisotope to the surface of the ceramic microsphere.

204. A method according to embodiment 203, wherein the radioisotope is coupled to the surface of the ceramic microsphere in the form of a Lewis acid-base adduct.

205. A method according to embodiments 203 or 204, wherein the radioisotope is a metallic radio isotope.

206. A method according to any of embodiments 203 to 205, wherein the radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, Al$^{18}$F and/or combinations thereof.

207. A method according to any of embodiments 203 to 206, wherein the radioisotope is provided in the form of a salt.

208. A method according to any of embodiments 203 to 207, wherein the radioisotope is reacted with the ceramic microsphere in the presence of a reducing agent.

209. A method according to embodiment 208, wherein the reducing agent is selected from one or more of a stannous salt, a stannous hydrate, HCl, sodium borohydride, sodium dithionite, ferrous sulfate, ferric chloride plus ascorbic acid, hypophosphorous acid, and/or hydrazine.

210. A method according to any of embodiments 203 to 209, wherein the radioisotope is $^{99m}$Tc.

211. A method according to embodiment 210, wherein the $^{99m}$Tc is provided in the form of a pertechnetate salt.

212. A method according to embodiment 210, wherein the $^{99m}$Tc is provided in the form of a pertechnetate salt and the reaction is carried out in the presence of stannous ions.

213. A method according to any of embodiments 203 to 209, wherein the radioisotope is $^{89}$Zr.

214. A method according to embodiment 213, wherein the $^{89}$Zr is provided in the form of $^{89}$Zr oxalate.

215. A method according to embodiment 213 or 214, wherein the reaction is carried out in the presence of a base.

216. A method of making the imageable microsphere of any one of embodiments 145 to 192, the method comprising:
providing the inorganic substrate; and
chemically functionalizing the inorganic substrate with the at least one imageable radioisotope to provide the imageable microsphere.

217. The method of embodiment 216, in which the at least one imageable radioisotope is provided as a salt prior to chemically functionalizing the at least one imageable radioisotope to a surface of the inorganic substrate.

218. The method of embodiment 217, wherein the salt is an alkali metal salt, an alkali earth metal salt, a halogen salt, a polyatomic salt, or a salt with an organic acid.

219. The method of embodiment 217 or 218, wherein the reaction is carried out in the presence of a reducing agent.

220. The method of embodiment 219, wherein the reducing agent is selected from one or more of a stannous salt, a stannous hydrate, HCl, sodium borohydride, sodium dithionite, ferrous sulfate, ferric chloride plus ascorbic acid, hypophosphorous acid, and/or hydrazine.

221. A method according to any of embodiments 216 to 220, wherein the radioisotope is $^{99m}$Tc.

222. A method according to embodiment 221, wherein the $^{99m}$Tc is provided in the form of a pertechnetate salt.

223. A method according to embodiment 221, wherein the $^{99m}$Tc is provided in the form of a pertechnetate salt and the reaction is carried out in the presence of stannous ions.

224. A method according to any of embodiments 216 to 223, wherein the radioisotope is $^{89}$Zr.

225. A method according to embodiment 224, wherein the $^{89}$Zr is provided in the form of $^{89}$Zr oxalate.

226. A method according to embodiment 224 or 225, wherein the reaction is carried out in the presence of a base.

227. A method according to any one of embodiments 203 to 226, carried out in aqueous conditions.

228. A method according to any one of embodiments 203 to 227, additionally comprising recovering the imageable microsphere and/or washing the microsphere to remove unreacted radioisotope.

229. A method according to any of embodiments 203 to 228, additionally comprising resuspending the imageable microsphere in a pharmaceutically acceptable injectable aqueous medium.

230. An imageable microsphere obtainable by a method according to any of embodiments 203 to 229.

231. A method for determining an amount of therapeutic microspheres to provide to a body of a patient, the method comprising:
providing a population of imageable microspheres;
delivering the population of imageable microspheres to the patient by introducing the population of imageable microspheres to a first position in a vasculature of the patient;
allowing the population of imageable microspheres to distribute within the body of the patient;
determining a distribution of at least a portion of the population of the imageable microspheres within the body of the patient by imaging a portion of the body of the patient using an imaging modality; and
using the distribution of the imageable microspheres to calculate an amount of therapeutic microspheres to be delivered to the body of the patient.

232. The method of embodiment 231, wherein the portion of the body is an off-target area of the patient and the off-target area is a lung of the patient.

233. The method of embodiment 231, wherein the portion of the body is a target area of the patient and the target area is a liver of the patient.

234. The method of any one of embodiments 231 to 233, wherein the target area is divided into tumor and non-tumor tissue.

235. The method of one of embodiments 231 to 234, wherein an amount of therapeutic microspheres to be delivered to the patient is calculated.

236. The method of embodiment 235, wherein the amount calculated is delivered to the patient.

237. The method of any one of embodiments 231 to 236, wherein the imaging modality is SPECT.

238. The method of any one of embodiments 231 to 236, wherein the detection modality is PET.

239. The method of any one of embodiments 231 to 236, wherein the detection modality is gamma camera imaging.

240. The method of any one of embodiments 231 to 239, wherein the imageable microspheres are the imageable microspheres of any one of embodiments 145 to 202.

241. A method for treating a patient, the method comprising:
providing a population of imageable microspheres;
delivering the population of imageable microspheres to the patient by introducing the population of imageable microspheres to a first position in a vasculature of a body of the patient;
allowing the population of imageable microspheres to distribute within the body of the patient;
determining a distribution of at least a portion of the population of the imageable microspheres within the body of the patient by imaging a target section of the body of the patient using an imaging modality; and
using the distribution of the imageable microspheres to calculate an amount of therapeutic microspheres to be delivered to the body of the patient;
obtaining data regarding a distribution of an imageable therapeutic microsphere surrogate in a patient;
using the data to determine a dose of a therapeutic amount of microspheres to administer to the body of the patient;
delivering a population of therapeutic microspheres to the patient by introducing the population of therapeutic microspheres to a second position in the vasculature of the body of the patient;
allowing the population of therapeutic microspheres to distribute within the body of the patient, thereby treating the patient.

242. The method of embodiment 241, wherein the second position in the vasculature of the patient is the same as the first position in the vasculature of the patient or approximately the same position.

243. The method of embodiment 241 or 242, wherein the imaging modality is SPECT.

244. The method of embodiment 241 or 242, wherein the imaging modality is PET.

245. The method of embodiment 241 or 242, wherein the imaging modality is a gamma camera imaging.

246. The method of any one of embodiments 241 to 245, wherein the imageable microspheres are the imageable microspheres of any one of embodiments 145 to 202.

247. A method for treating a patient with therapeutic microspheres, the method comprising:
obtaining data calculated from the distribution of an imageable therapeutic microsphere surrogate in a patient;
using the data to determine an amount of therapeutic microspheres to be dosed to a body of the patient;
delivering the amount of therapeutic microspheres to the patient by introducing the amount of therapeutic microspheres to a first position in a vasculature of the patient;
allowing the therapeutic microspheres to distribute within the body of the patient; and
allowing the therapeutic microspheres to reside in the body of the patient, thereby treating the patient.

248. The method of embodiment 247, further comprising providing a population of imageable microspheres to the patient.

249. The method of embodiment 248, further comprising delivering the population of imageable microspheres to the patient by introducing the population of imageable microspheres to the first position in the vasculature of the body of the patient.

250. The method of embodiment 249, further comprising allowing the population of imageable microspheres to distribute within the body of the patient.

251. The method of embodiment 250, further comprising determining a distribution of at least a portion of the population of the imageable microspheres within the body of the patient by imaging a target section of the body of the patient using an imaging modality.

252. The method of embodiment 251, further comprising using the distribution of the imageable microspheres to calculate the amount of therapeutic microspheres to be delivered to the body of the patient.

253. A method of treating a tumor in a patient in need of treatment, the method comprising:
introducing a population of imageable microspheres to the patient;
allowing the imageable microspheres to distribute within the patient over a period of time;
determining the distribution of the imageable microspheres at a site within the patient by imaging the imageable microspheres using an imaging modality;
determining an estimated effective dose at the site based on the distribution of the imageable microspheres had the imageable microspheres been replaced by therapeutic microspheres; and
administering an amount of the therapeutic microspheres to the patient based on the estimated effective dose.

254. The method of embodiment 253, wherein the population of imageable microspheres comprises the imageable microsphere of any one of embodiments 145 to 202.

255. The method of embodiment 253 or 254, wherein the site is a malignant or benign tumor and/or a non-tumorous tissue.

256. The method of embodiment 253 or 254, wherein the site is a malignant tumor.

257. The method of embodiment 256, wherein the site is a malignant tumor.

258. A method of predicting the degree of off-target delivery to the lung or the gastrointestinal tract during treatment of a patient in need of radioisotopic cancer treatment, the method comprising:
introducing a population of imageable microspheres to the patient;
allowing the imageable microspheres to distribute within the patient over a period of time;
determining the distribution of the imageable microspheres within a lung of the patient by imaging the imageable microspheres using an imaging modality;
determining an estimated dose of radiation in the lung or gastrointestinal tract respectively of the patient if the imageable microspheres had been replaced by radioisotopic therapeutic microspheres;
determining a dose of the radioisotopic therapeutic microspheres that is sufficient to cause clinically relevant lung or gastro intestinal changes due to off-target delivery; and
administering a dose of the radioisotopic therapeutic microspheres to a patient that is below the dose of the radioisotopic therapeutic microspheres determined to be sufficient to cause clinically relevant lung or gastrointestinal changes due to off-target delivery.

259. The method of embodiment 258, wherein the population of imageable microspheres comprises the imageable microsphere of any one of embodiments 145 to 202.

260. A method of reducing lung or gastrointestinal damage during treatment of a patient in need of radioisotopic cancer treatment, the method comprising:
introducing a population of imageable microspheres to the patient;
allowing the imageable microspheres to distribute within the patient over a period of time;
determining the distribution of the imageable microspheres within a gastrointestinal tract or lung of the patient by imaging the imageable microspheres using an imaging modality;
determining an estimated dose of radiation in the gastrointestinal tract or lung of the patient if the imageable microspheres had been replaced by radioisotopic therapeutic microspheres;
determining a dose of the radioisotopic therapeutic microspheres that is sufficient to cause gastrointestinal tract damage; and
administering a dose of the radioisotopic therapeutic microspheres to the patient that is below the dose of the radioisotopic therapeutic microspheres determined to be sufficient to cause damage gastrointestinal tract.

261. The method of embodiment 260, wherein the population of imageable microspheres comprises the imageable microsphere of any one of embodiments 145 to 202.

262. A kit comprising:
a microsphere comprising:
a substrate comprising an inorganic material that comprises metalloid or metal atoms bonded to non-metal atoms, the substrate comprising:
a core extending to a surface, the core comprising a first portion of the metalloid or metal atoms bonded to the non-metal atoms and the surface comprising a second portion of the metalloid or metal atoms bonded to the non-metal atoms; and
instructions for reacting an imageable radioisotope with the substrate such as to bind the imageable radioisotope directly to the substrate through at least a portion of the non-metal atoms at the surface of the substrate.

263. A kit comprising
a microsphere comprising:
an inorganic substrate; wherein the inorganic substrate comprises at least one non-metal, a metalloid, or a transition metal oxide; and instructions for binding an imageable radioisotope to the surface of the inorganic substrate through a Lewis acid-base coordination bond.

264. A kit comprising a microsphere comprising a ceramic microsphere substrate and instructions for carrying out a reaction in which an imageable radioisotope is coupled to the ceramic microsphere substrate as a Lewis acid base adduct.

265. A kit according to any of embodiments 262 to 264, comprising 10 μl to 2 ml of microspheres by packed volume, in a sealed unit.

266. A kit of embodiment 110, wherein the microspheres are provided in a vial or a syringe.

267. A kit according to any of embodiments 262 to 266, wherein the imageable radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K $^{82}$Rb, $^{24}$Na, $^{45}$Ti, $^{44}$Sc, $^{51}$Cr, $^{18}$F, Al$^{18}$F.

268. A kit according to any of embodiments 262 to 267, which additionally comprises a reducing agent.

269. A kit according to embodiment 268, wherein the reducing agent is selected from one or more of a stannous salt, a stannous hydrate, concentrated HCl, sodium borohydride, sodium dithionite, ferrous sulfate, ferric chloride plus ascorbic acid, hypophosphorous acid, and/or hydrazine.

270. A kit according to embodiments 268 or 269, wherein the reducing agent is a stannous salt, the radioisotope is $^{99m}$Tc and the radioisotope is in the form of a pertechnetate salt.

271. A kit according to any one of embodiments 262 to 267, wherein the radioisotope is $^{89}$Zr.

272. A kit according to embodiment 271, wherein the radioisotope is in the form of $^{89}$Zr zirconium oxalate or zirconium chloride 273. The kit of any one of embodiments 262 to 272, further comprising therapeutic microspheres.

274. The kit of embodiment 273, wherein the therapeutic microspheres comprise a therapeutic radioisotope.

275. The kit of embodiment 274 wherein the therapeutic microspheres comprise $^{90}$Y, $^{166}$Ho, $^{177}$Lu, $^{131}$I, $^{89}$Sr, $^{153}$Sm, $^{223}$Ra, $^{224}$Ra, $^{211}$At, $^{225}$Ac, $^{227}$Th, $^{212}$Bi $^{213}$Bi, and/or $^{212}$Pb.

276. The kit of any one of embodiments 273 to 275, wherein the therapeutic microspheres are of the same chemical composition as the imageable microspheres.

277. The kit of any one of embodiments 273 to 276, wherein the therapeutic microspheres comprise an yttrium aluminum silicon oxide.

278. The kit of any one of embodiments 262 to 277, further comprising one or more of a vascular access needle, a vascular guidewire, a vascular sheath (e.g., 4-6Fr), a vascular catheter (4-5Fr), a microcatheter, syringes, and a vial.

EXAMPLES

The following examples provide illustrations of some embodiments disclosed herein and are not intended to be limiting. One skilled in the art will appreciate readily that the present disclosure is well adapted to carry out the objects and obtain the ends and advantages mentioned, as well as those objects, ends and advantages that flow naturally from the embodiments disclosed herein. Changes therein and other uses which are characteristic attributes of the disclosure as defined by the scope of the claims will occur to those skilled in the art.

Example 1: Preparation of Zirconium-89 Coupled Yttrium Aluminum Silicon Oxide (YAS) Microspheres A 4 mL glass vial was charged with yttrium aluminum silicon oxide (YAS) glass beads (TheraSphere®, Biocompatibles UK Ltd, provided as non-radioactive spheres which had not been exposed to neutron bombardment. $Y_2O_3$ was therefore in the form of naturally occurring $^{89}$Y) and suspended in 300 μL of deionized water. Next, a 2 μL aliquot of Zirconium-89 in 1 M oxalic acid (3D imaging, Little Rock, AK)) (about 100 microcuries (μCi)) was added to the reactor vial, followed by 2 μL of 2 M sodium carbonate, followed by a Teflon®-coated magnetic stir bar. The reaction mixture was stirred and heated for 2 hours on a 120° C. aluminum heating block, then removed from the block and allowed to cool to room temperature. The microspheres were suspended in 3.0 mL of deionized water and passed through a 0.22 μm syringe filter to collect the microspheres for labeling analysis. The glass vial was rinsed with an additional 4 mL of deionized water, which was then passed through the syringe filter. The syringe filter (containing the labeled microspheres), the glass vial, and the deionized water filtrate were analyzed by a gamma well counter and the results are summarized in the Table 1 below.

TABLE 1

| Mass of TheraSphere | Filter (microspheres) | Remaining in reactor vial | Deionized water filtrate | Radio-chemical Yield |
|---|---|---|---|---|
| 100 mg | 118 μCi | 30 μCi | 4 μCi | 77% |
| 25 mg | 539 μCi | 310 μCi | 10 μCi | 63% |
| 25 mg* | 122 μCi | 363 μCi | 8 μCi | 25% |
| 10 mg | 46 μCi | 43 μCi | 10 μCi | 46% |
| 10 mg# | 78 μCi | 46 μCi | 6 μCi | 60% |

*Reactor vial was not charged with a Teflon-coated magnetic stir bar.

Example 2: Preparation of $^{99m}$Tc Coupled Yttrium Aluminum Silicon Oxide Microspheres Tin(II) chloride dihydrate (1 mg) was added to a 1 dram vial and dissolved in 400 μL of deionized water. In a separate 1 dram vial, yttrium aluminum silicon oxide glass beads ($^{89}$Y, non-radioactive TheraSphere-TS) were added, followed by 100 μL of [$^{99m}$Tc]sodium pertechnetate (>30 mCi/mL). The tin(II) chloride dihydrate solution was added to the TheraSphere vial, briefly mixed (approximately 3 seconds) and the vial was capped and allowed to react at room temperature for 60 minutes. The microspheres were suspended in 3.0 mL of deionized water and passed through a 0.22 μm syringe filter to collect the microspheres for labeling analysis. The glass vial was rinsed with an additional 4 mL of deionized water, which was then passed through the syringe filter. The syringe filter (containing the labeled microspheres), the glass vial, and the deionized water filtrate were analyzed by a gamma well counter and the results are summarized in the table below.

TABLE 2

| Mass of TheraSphere | Filter (microspheres) | Remaining in reactor vial | Deionized water filtrate | Radio-chemical Yield |
|---|---|---|---|---|
| 100 mg | 4.1 mCi | 0.26 mCi | 1.2 mCi | 73% |
| 25 mg | 1.65 mCi | 0.63 mCi | 0.25 mCi | 63% |

TABLE 2-continued

| Mass of TheraSphere | Filter (microspheres) | Remaining in reactor vial | Deionized water filtrate | Radio-chemical Yield |
|---|---|---|---|---|
| 25 mg* | 2.28 mCi | 0.15 mCi | 0.1 mCi | 90% |
| 10 mg | 1.766 mCi | 0.244 mCi | 0.354 mCi | 75% |

All radiochemical yield (RCY) data are reported as mean of n = 3 runs.
*Reactor vial was not charged with a Teflon-coated magnetic stir bar.

Example 3: [$^{89}$Zr] Microsphere Ligand Challenge with DFO Chelate

YAS microspheres (e.g., Therasphere) (suspended in 200 μL sterile saline, pH 7-8) were mixed with increasing concentrations of desferrioxamine (DFO), ranging from 0.05 to 5 mM, and incubated at 37° C. under constant stirring. At each time point, 5 μL of solution was removed, added to a 0.45 μm spin filter, and diluted with 100 μL of deionized water. The spin filter was centrifuged at 13,200×G for 60 seconds, 100 μL of deionized water was added back to the spin filter and centrifugation repeated. The spin filter was removed from the microcentrifuge tube and the supernatant was analyzed by gamma spectroscopy, then counted in a gamma counter, to detect formation of possible $^{89}$Zr-DFO. Negligible $^{89}$Zr detachment was detected for $^{89}$Zr-TS within 48 h, demonstrating a strong binding affinity of $^{89}$Zr to TS. Results are shown in FIG. 2.

Example 4: Test for Specificity of Tin (II) Chloride as a Reducing Agent

Several oxidants and reducing agents were tested on the premise of understanding the specificity of tin(II) chloride for reducing pertechnetate toward reaction with TheraSphere. Tin is not only expected to actively reduce Tc(VII) to Tc(V), but seems to actively participate in the binding of $^{99m}$Tc to TheraSphere. Several reducing agents were attempted to facilitate TheraSphere/$^{99m}$Tc coupling: FeCl$_2$/ascorbic acid (pH=2); sodium borohydride; and zinc metal. None of the reducing agents yielded substantial radiochemical yield's of $^{99m}$Tc-TheraSphere and were not considered further. This suggests tin plays a role in the binding of $^{99m}$Tc to TheraSphere.

Example 5: Effect of Reaction Volume on the Yield of $^{99M}$Tc Coupled Microspheres Tin(II) chloride dihydrate (1 mg) was added to a 1 dram vial and dissolved in deionized water as indicated in Table 3. In a separate 1 dram vial, 10 mg of yttrium aluminum silicon oxide glass beads (TheraSphere) are added, followed by 100 μL of [$^{99m}$Tc]sodium pertechnetate (>30 mCi/mL). The tin(II) chloride dihydrate solution was added to the TheraSphere vial, briefly mixed (approximately 3 seconds) and the vial was capped and allowed to react at room temperature for 60 minutes. The microspheres were suspended in 3.0 mL of deionized water and passed through a 0.22 μm syringe filter to collect the microspheres for labeling analysis. The glass vial was rinsed with an additional 4 mL of deionized water, which was then passed through the syringe filter. The syringe filter (containing the labeled microspheres), the glass vial, and the deionized water filtrate were analyzed by a gamma well counter and the results are summarized in the table below.

TABLE 3

| Reaction volume (μL) | Filter (microspheres) | Remaining in reactor vial | Deionized water filtrate | Radio-chemical Yield |
|---|---|---|---|---|
| 100 | 0.44 mCi | 0.01 mCi | 0.003 mCi | 95% |
| 200 | 0.055 mCi | 0.015 mCi | 0.01 mCi | 75% |
| 500 | 0.033 mCi | 0.022 mCi | 0.026 mCi | 41% |

Example 6: Coupling to Alternative Ceramic Microparticles

Examples one and two were repeated using silicon oxide and silicon aluminum oxide microparticles. Silicon-aluminum oxide microspheres were obtained from Steag Energo Mineral. Silica microspheres were purchased from EPRUI Biotech Co. Limited (Product #: EPRUI-SI-20), which consisted of SiO$_2$, as monodisperse microspheres having a diameter of 20 μm.

TABLE 4

$^{89}$Zr silicon oxide microparticle

| Mass | Filter (microspheres) | Remaining in reactor vial | Deionized water filtrate | Radio-chemical Yield |
|---|---|---|---|---|
| 25 mg | 138 μCi | 0 μCi | 0 μCi | quantitative |
| 10 mg | 394 μCi | 10 μCi | 0 μCi | >97% |

TABLE 5

$^{99m}$Tc silicon oxide microparticle

| Mass | Filter (microspheres) | Remaining in reactor vial | Deionized water filtrate | Radio-chemical Yield |
|---|---|---|---|---|
| 25 mg | 3.1 mCi | 0.0 mCi | 0.01 mCi | quant. |
| 10 mg | 2.87 mCi | 0.02 mCi | 0.01 mCi | >98% |

TABLE 6

$^{89}$Zr silicon-aluminum oxide microparticle

| Mass | Filter (microspheres) | Remaining in reactor vial | Deionized water filtrate | Radio-chemical Yield |
|---|---|---|---|---|
| 25 mg | 900 μCi | 0 μCi | 0 μCi | quant. |
| 10 mg | 401 μCi | 10 μCi | 0 μCi | quant. |

TABLE 7

$^{99m}$Tc silicon-aluminum oxide microparticle

| Mass | Filter (microspheres) | Remaining in reactor vial | Deionized water filtrate | Radio-chemical Yield |
|---|---|---|---|---|
| 25 mg | 3.5 mCi | 0.0 mCi | 0.01 mCi | quant. |
| 10 mg | 3.2 mCi | 0.02 mCi | 0.01 mCi | quant. |

Example 7: Test for Mutual Dependency of 99mTc and TheraSphere on Tin for Product Formation Several reactions were performed with various conditions as shown below.

General reaction conditions using 10 mg of TheraSphere, 0.5-1.0 mg of $SnCl_2$, 3 mCi of $^{99m}Tc$, and 400 μL of deionized water.

General reaction conditions using 10 mg of TheraSphere, 3 mCi of $^{99m}Tc$, and 400 μL of deionized water. No $SnCl_2$.

General reaction conditions using 25 mg of TheraSphere, 3 mCi of $^{99m}Tc$, and 400 μL of deionized water. No $SnCl_2$.

General reaction conditions using 0.5-1.0 mg of $SnCl_2$, 3 mCi of $^{99m}Tc$, and 400 μL of deionized water. No TheraSphere.

TABLE 8

| Reaction | Filter (microspheres) | Remaining in reactor vial | Deionized water filtrate | Radio-chemical Yield |
|---|---|---|---|---|
| 1 | 2.1 mCi | 0.35 mCi | 0.23 mCi | 80% |
| 2 | 0.1 mCi | 0 mCi | 2.3 mCi | <1% |
| 3 | 0.1 mCi | 0.03 mCi | 2.3 mCi | <1% |
| 4 | 1.2 mCi | 0.2 mCi | 1.1 mCi | 48% |

As demonstrated by Reaction 4, there is an association between some oxidation state of tin and $^{99m}Tc$. However, in the conditions tested, the product degrades in solution over 120 minutes without TheraSphere also being present, which is evident in Reaction 1. Also, there is no reaction when $^{99m}Tc$ is mixed with TheraSphere alone without tin being present. The combination of the three reagents produces a stable product, which is demonstrated in our in vitro stability assay below.

Example 8: Assay for Solution Stability of a $^{99M}Tc$ and $^{89}Zr$ Coupled Yttrium Aluminum Silicon Oxide Spheres Preparation of Sample Solutions Three separate solutions were prepared as follows: 1) Vial #1: 10 mL of PBS and either 3-5 mCi of $^{99m}Tc$-TheraSphere or 100-150 μCi of $^{89}Zr$-TheraSphere, mix for homogeneity; 2) Vial #2: 10 mL of goat serum, 4±1 mCi of $^{99m}Tc$-TheraSphere (suspended in 100 μL of PBS to facilitate transfer) or 125±25 μCi of $^{89}Zr$-TheraSphere, mix for homogeneity; 3) Vial #3: 10 mL of goat serum (other serums can be used, e.g., horse, goat, or other mammal), 4±1 mCi of $^{99m}Tc$-TheraSphere (suspended in 100 μL of PBS to facilitate transfer) or 125±25 μCi of $^{89}Zr$-TheraSphere, 100 μL of 0.1 M HCl (Check pH, should be below 4, if not, add more 0.1M HCl until <4. It is okay if you overshoot pH to between 1 and 3, just note final pH), mix for homogeneity. Each vial was incubated at 37° C. for 8 hours. From each vial: Remove 100 μL, centrifuge and aliquot 10 μL of the supernatant for activity measurement into a 1 dram vial or microcentrifuge tube. To determine any effect of time, samples were withdrawn at selected time points.

Prepare Standards for Gamma Counter

Figure 3A:
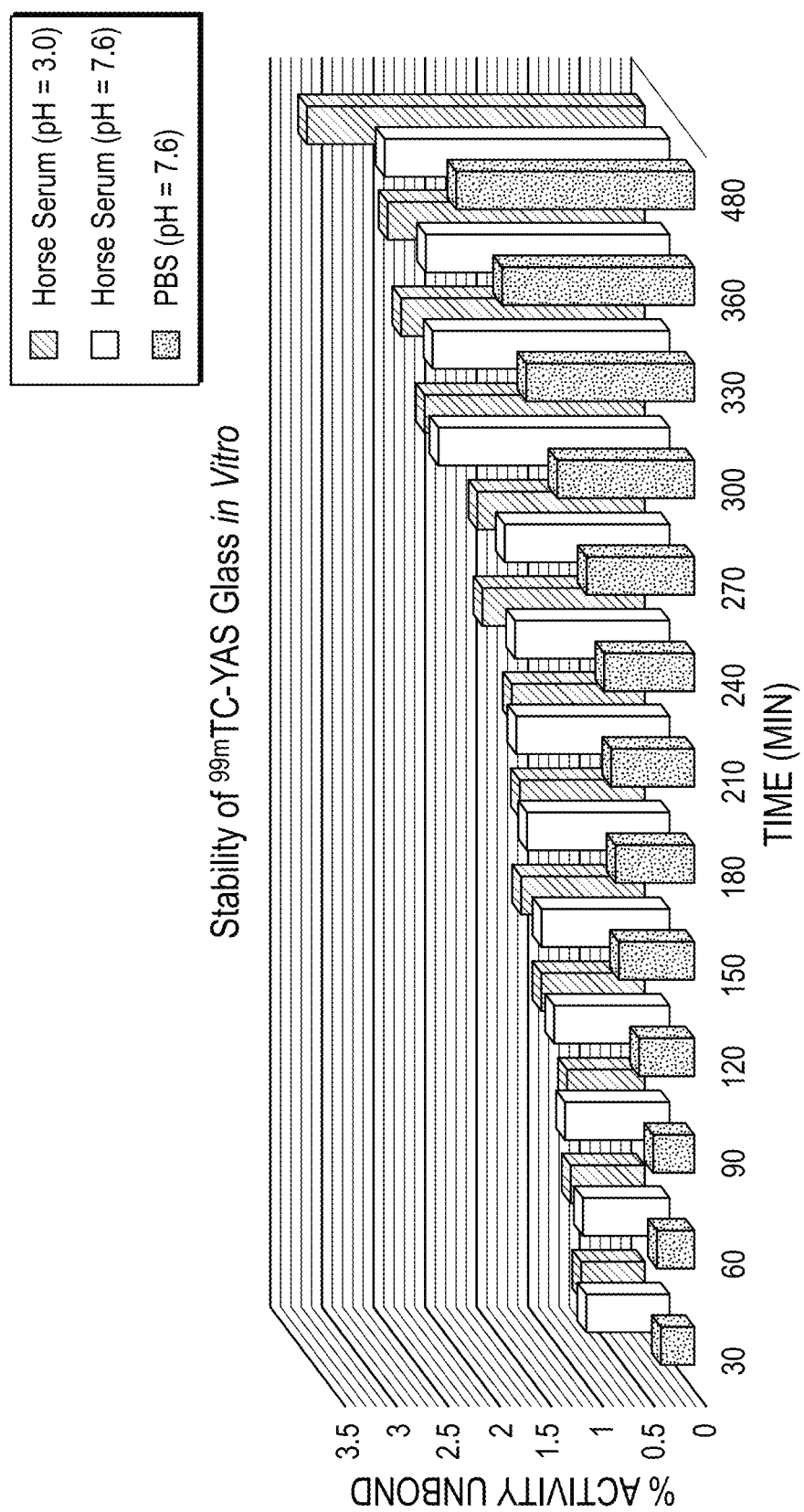
FIG. 3A depicts results for a stability study for an embodiment of an imageable radioisotopic particle with a $^{99m}$Tc microsphere.
Figure 3B:
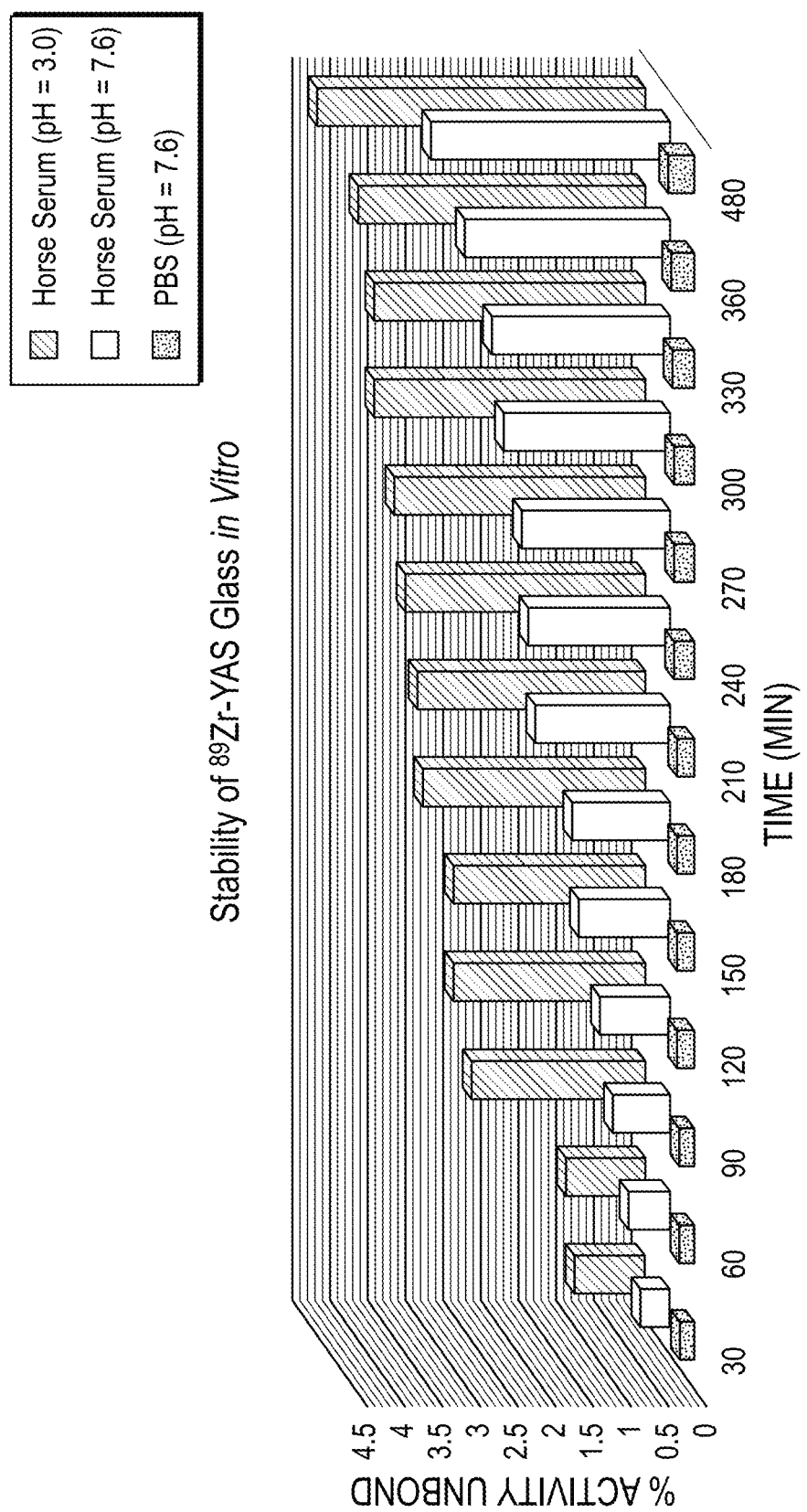
FIG. 3B depicts results for a stability study for an embodiment of an imageable radioisotopic particle with a $^{89}$Zr microsphere.

To a 100 mL volumetric flask was added 4±1 mCi of $^{99m}Tc$-TheraSphere (suspended in 100 μL of PBS to facilitate transfer) or 125±25 μCi of $^{89}Zr$-TheraSphere. The solutions were diluted to 100 mL with deionized water and mixed. From the flask was removed 5×1 mL aliquots which were added into 5 separate vials. Stability data is shown in FIGS. 3A and 3B.

Figure 4A:
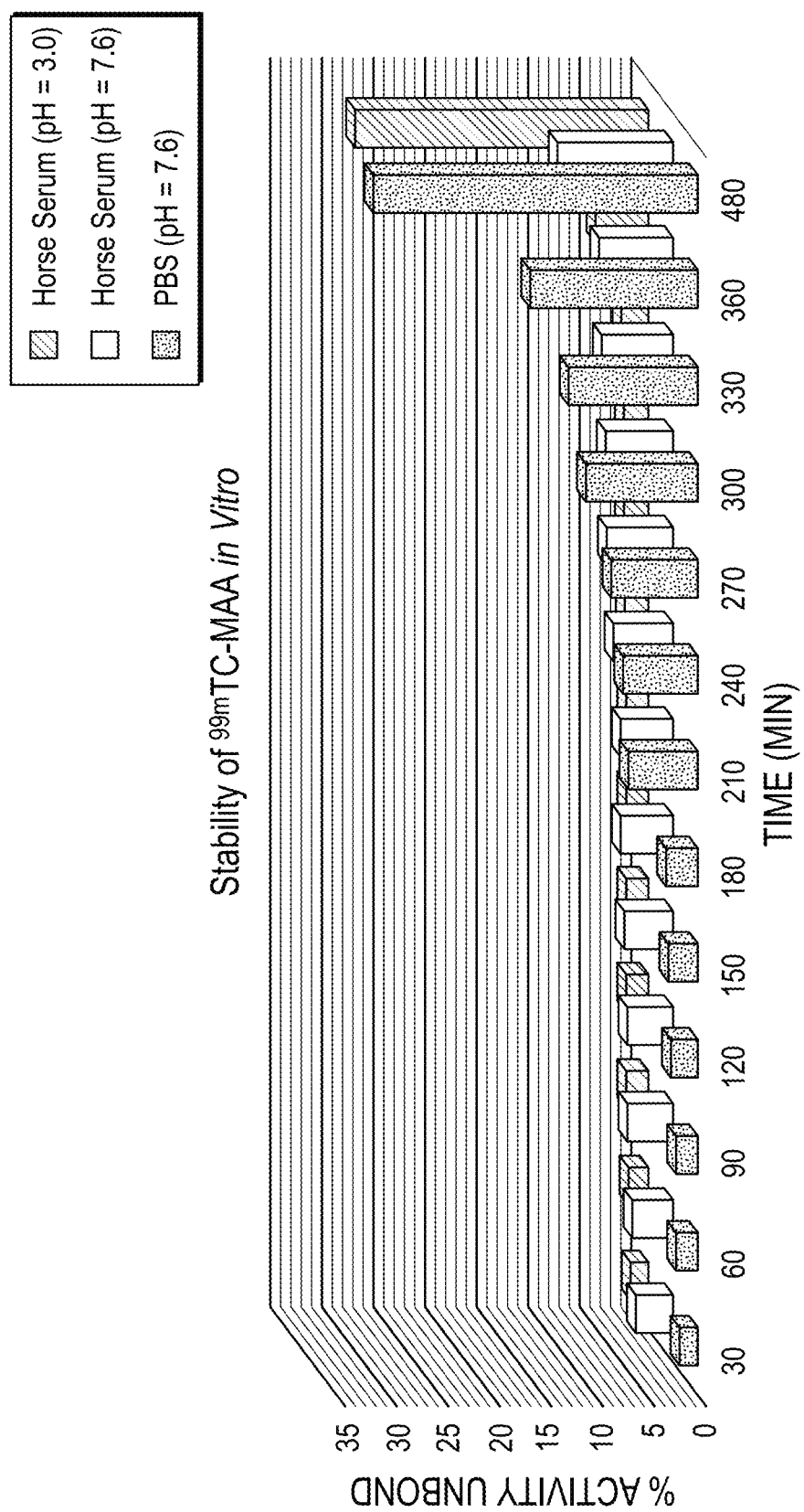
FIG. 4A depicts results for a stability study for a comparator imageable particle comprising macro-aggregated albumen labelled with technetium-99m.

To compare the relative stability of $^{99m}Tc$- and $^{89}Zr$-TheraSphere against the industry standard in vitro, we performed the same serum assay using $^{99m}Tc$-MAA. Three separate solutions were prepared as follows: 1) Vial #1 (Buffer): 10 mL of PBS, 4±1 mCi of $^{99m}Tc$-MAA, mixed for homogeneity; 2) Vial #2 (Serum): 10 mL of goat serum, 4±1 mCi of $^{99m}Tc$-MAA, mixed for homogeneity; 3) Vial #3 (Serum and Acid): 10 mL of goat serum; 4±1 mCi of $^{99m}Tc$-MAA; 100 μL of 0.1 M HCl (Check pH, should be below 4, if not, add more 0.1M HCl until <4. It is okay if you overshoot pH to between 1 and 3, just note final pH), mixed for homogeneity. Each vial was incubated at 37° C. for 8 hours. From each vial: Remove 100 μL, centrifuge and aliquot 10 μL of the supernatant for activity measurement into a 1 dram vial or microcentrifuge tube. To determine any effect of time, samples were withdrawn at selected time points. Results are shown in FIG. 4.

The relative stabilities of all imaging surrogates are summarized below in the following Tables.

TABLE 9

Relative solution stability of TS imaging surrogates

| | 2 hr | 4 hr | 6 hr | 8 hr |
|---|---|---|---|---|
| PET-YAS | >99% | >99% | >99% | >99% |
| SPECT-YAS | >99% | >99% | >98% | >97% |
| Tc-MAA | >97% | >93% | >84% | >68% |

TABLE 10

Relative serum stability of TS imaging surrogates

| | 2 hr | 4 hr | 6 hr | 8 hr |
|---|---|---|---|---|
| PET-YAS | >99% | >98% | >97% | >96% |
| SPECT-YAS | >99% | >98% | >97% | >97% |
| Tc-MAA | >97% | >94% | >92% | >88% |

Example 9: Buffer and pH Studies

To a vial was added 0.5-1.0 mg of $SnCl_2$. 500 uL of buffer solution was added to the vial. The solution was filtered into a clean 1 dram vial. In a separate 1 dram vial (reaction vial), 10 mg of YAS microspheres were added along with 20 uL of Tc-99m stock solution. 380 uL $SnCl_2$ solution was added to the reaction vial, for a total reaction volume of 400 uL. The reaction vial was capped and mixed by hand for 3-5 seconds, then allowed to react at room temperature for 1 hr without stirring. The vial was then mixed the reaction mixture was pulled into a syringe with an 18 G×1.5" needle. The labelled YAS microspheres were trapped on a 0.2 um syringe filter. A rinse reaction of the reaction vial was performed with 400 uL of DI H2O and the was trapped on the syringe filter.

Vial Labelling and Buffer List:
1. Saline (pH 5)
2. PBS (pH 7.4)
3. Acetate Buffer in Saline (pH 5)
4. Citrate Buffer (pH 3)
5. Citrate Buffer (pH 4)
6. Citrate Buffer (pH 5)

Analysis: Count the initial activity in the reaction vial (I), waste vial (W), Syringe Filter (SF), reaction vial (V), and note the background (BKG). Table 11 Provides the results.

TABLE 11

| Vial | I | W | SF |
|---|---|---|---|
| 1 | 2.70 mCi @ 1317 | 42 uCi @ 1327 | 2.27 mCi @ 1327 |
| 2a | 2.63 mCi @ 1328 | 118.6 uCi @ 1331 | 2.51 mCi @ 1330 |
| 2b | 1.96 mCi @ 1556 | 1.06 uCi @ 1558 | 726 uCi @ 1558 |
| 2c | 1.95 mCi @ 1600 | 870 uCi @ 1602 | 885 uCi @ 1603 |
| 3 | 2.60 mCi @ 1333 | 4 uCi @ 1336 | 2 mCi @ 1336 |
| 4 | 2.57 mCi @ 1337 | 2.17 mCi @ 1341 | 230 uCi @ 1341 |
| 5 | 2.58 mCi @ 1343 | 2.29 mCi @ 1346 | 263 uCi @ 1346 |
| 6 | 2.53 mCi @ 1348 | 2.30 mCi @ 1350 | 206 uCi @ 1350 |

| Vial | V | BKG |
|---|---|---|
| 1 | 420 uCi @ 1327 | 3 uCi @ 1328 |
| 2a | 124 uCi @ 1332 | 3 uCi @ 1332 |
| 2b | 174 uCi @ 1559 | 3.8 uCi @ 1559 |
| 2c | 197 uCi @ 1602 | 2.6 uCi @ 1603 |
| 3 | 642 uCi @ 1336 | 3 uCi @ 1337 |
| 4 | 10 uCi @ 1341 | 3 uCi @ 1342 |
| 5 | 12 uCi @ 1346 | 3 uCi @ 1347 |
| 6 | 37 uCi @ 1350 | 2.5 uCi @ 1351 |

Figure 4B:
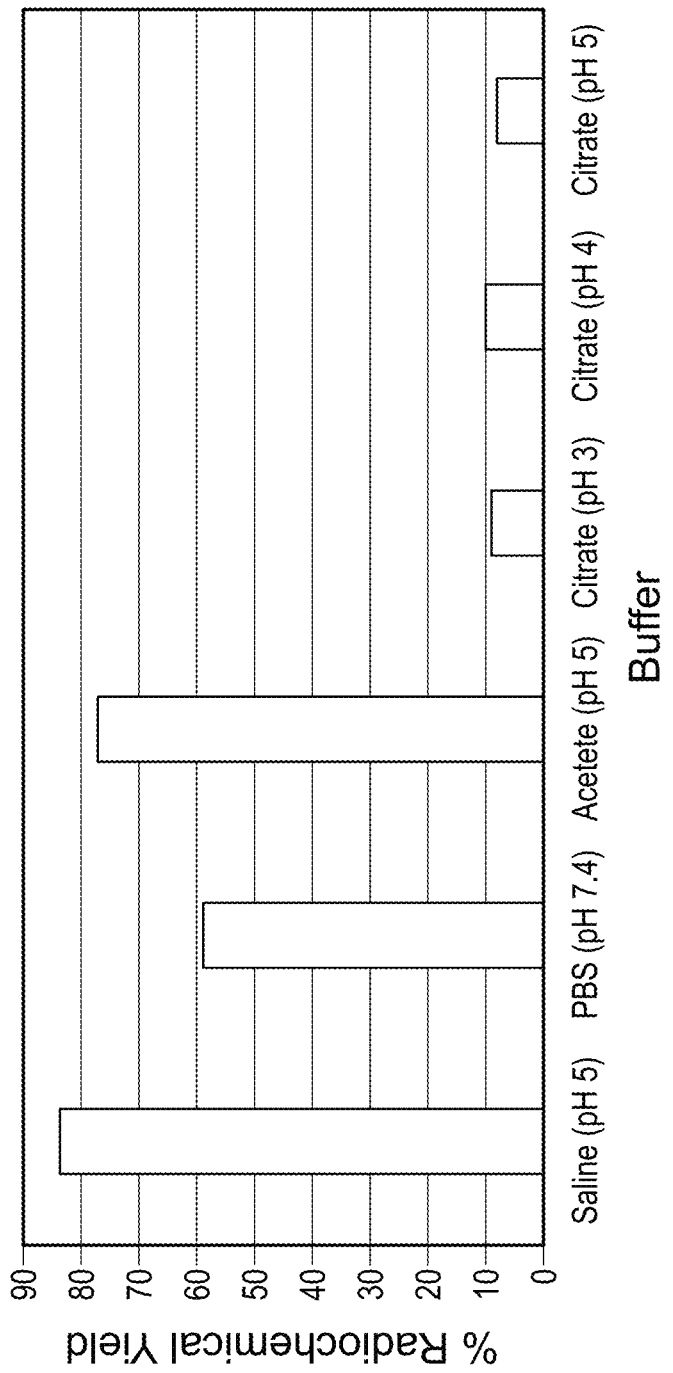
FIG. 4B provides results of radioisotope functionalization performed at varying pH levels and in various buffers.

As shown in FIG. 4B, buffering solutions may have a negative impact on the production of [99mTc] YAS microspheres. The best radiochemical yields were achieved using saline as the reaction solvent. Any attempt to buffer a solution with analyte and varying pH resulted in lower yields.

Example 10: Prophetic Al$^{18}$F Embodiment

Fluoride ion binds most metals, but forms particularly strong bonds with aluminum (III), which has been demonstrated historically to form complexes with metal-binding chelates; resulting in a highly stable (670 kJ/mol) Al—F bond. Aluminum forms octahedral complexes, thus, pentadentate coordination would be preferred for forming in vitro and in vivo stable 18F surrogates. [18F]fluoride is readily commercially available as an aqueous solution and thus, for practical use in a hospital setting, the reagents and reaction conditions should be compatible with aqueous reaction conditions. YAS glass (10 mg) and [18F]fluoride (supplied as an aqueous solution) are mixed with aluminum trichloride hydrate (monohydrate, hexahydrate, or other hydrated species to indicate compatibility with aqueous solutions) in pH 4 acetate buffer and an appropriate chelator (NOTA, NODA, trimethyltriazonane or other chelator species to support an octahedral aluminum-fluoride complex). The solution is heated at 100° C. for 15-30 minutes at which time the [18F]Al-YAS material is removed from heat and purified for use.

Example 11: In Vivo Animal Study

Radioembolization involves the endovascular delivery of particles with embedded radiation producing material through the arterial vasculature for the treatment of malignancy. Current FDA approved methods for radioembolization focus upon treatment of primary or metastatic liver cancer, but other organ systems may potentially serve as targets for therapy. Safe and effective delivery of therapy requires producing a dose that is customized to the target area of treatment. Various dosing methodologies currently exist, which may include variables such as target liver volume and, in some cases, liver tumor volume. No currently approved methodologies factor in patient-specific consideration of preferential vascular flow to tumors or number of radioembolic particles required for complete coverage of tumor. Addressing these last two variables may be best accomplished by the initial administration of a radioembolization dosing surrogate that is as close as possible with respect to size distribution, geometry, and specific gravity to the actual therapeutic radioembolization device. Boston Scientific produces a radioembolization device that is comprised of a glass microsphere with embedded $^{89}$Y that is converted to $^{90}$Y, a primary beta emitting particle. An optimal dosing surrogate would involve labeling the surface of glass microspheres with a radioisotope that may be visualized through positron emission tomography (PET) or single photon emission computed tomography (SPECT). Such a particle could be administered endovascularly during the initial planning procedure for this therapy and could be subsequently visualized by a PET or SPECT scanner to determine optimal dosing parameters for the subsequent administration of this therapy.

Figure 5A:
FIGS. 5A and 5B provide axial images from woodchuck with large bilateral hepatoma.

A series of proof-of-concept experiments were performed at the University of Virginia to explore the distribution of $^{89}$Zr labeled iSpheres (YAS microspheres; as prepared in Example 1) following catheter directed delivery of this agent. The current protocol employed $^{89}$Zr labeled microspheres in a woodchuck hepatoma model to explore the: (i) distribution, (ii) in vivo stability, and (iii) visualization of microspheres administered in a catheter-directed fashion through the hepatic artery. Specific procedures included: (i) magnetic resonance imaging (MRI) of the abdomen and pelvis in multiple phases of intravascular contrast (FIGS. 5A and 6A), (ii) angiography for positioning of a microcatheter within the hepatic artery (FIG. 6B), (iii) positron emission tomography-computed tomography (PET-CT) imaging of a scout dose (1.3 mg) and full dose (13 mg) (FIG. 5B) of $^{89}$Zr labeled microspheres, and (iv) fusion of PET-CT and MRI image datasets with quantitative analysis of uptake in tumor and normal liver (FIGS. 7A and 7B).

Briefly, woodchucks infected with WHV (woodchuck hepatitis virus) were identified by immunoassay by the supplier, Northeastern Wildlife (Harrison, ID). Blood samples were obtained every 3-4 months by the supplier to assess levels of WHV DNA levels to verify that the animals remain virus carriers. Serum gamma-glutamyl transferase (GGT), a serum marker for the presence of hepatocellular tumors was also be determined. Animals with GGT levels greater than 50 IU/dL were sent by the supplier. Woodchucks were evaluated by ultrasound to search for hepatic tumors and evaluate their size and position. A single ultrasound US session was be performed per animal prior to their shipment to UVA to confirm presence of tumors.

Figure 6A:
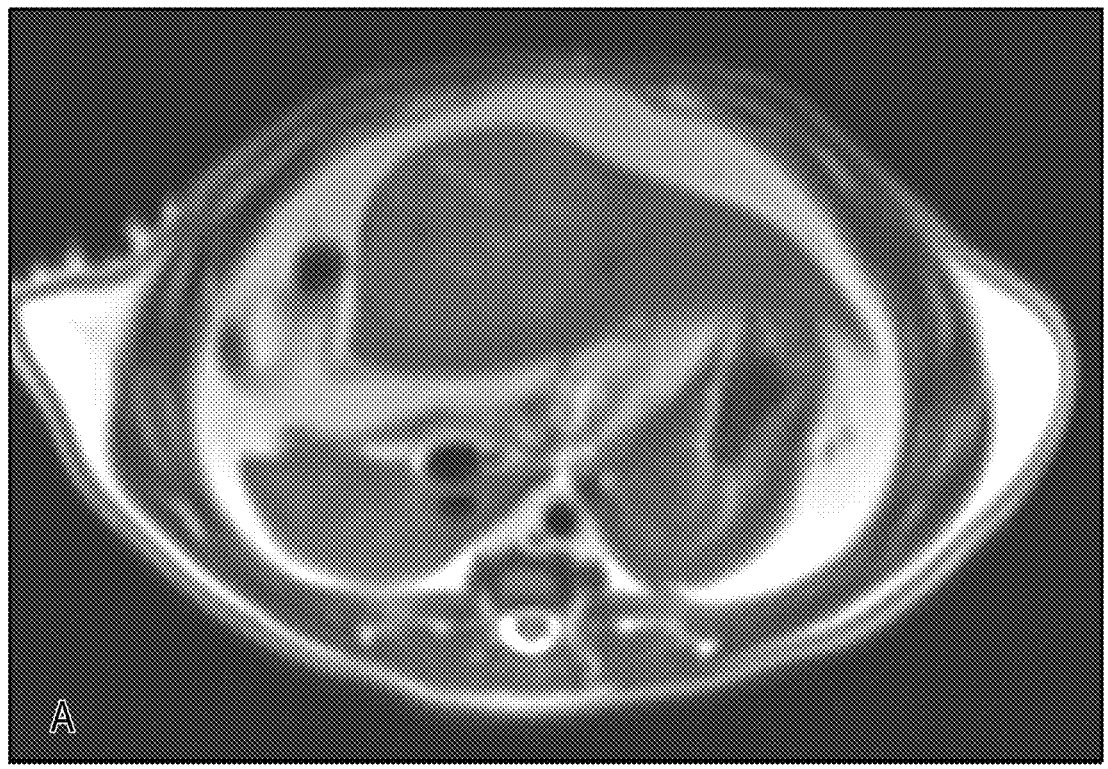
FIGS. 6A and 6B provide images taken of a woodchuck.
Figure 6B:

Prior to embolization, woodchucks were brought to a preparatory area and anesthesia was performed by veterinary staff. They administered ketamine (25-50 mg/kg) and xylazine (1-5 mg/kg) intramuscular. Atropine [0.04 mg/kg] was administered before intubation. The animal was intubated and maintained on a ventilator with isoflurane 1.5-2.5% in oxygen. The animal was placed on a heating pad to maintain body temperature. Animals underwent MRI (FIGS. 5A and 6A) on a Siemens 3 Tesla Prisma scanner (Erlangen, Germany) prior to angiography (FIG. 6B). For the MRI procedure, 1 mg/kg of pharmaceutical grade Magnevist was used.

Immediately following completion of the MRI (shown in FIGS. 5A and 6A), the animal was brought to the angiography suite. Ultrasound was used to gain access into the right common femoral artery using a 4F micropuncture kit (Cook Medical, Bloomington, IN). A 4F Glidesheath Slender Sheath (Terumo Medical, Somerset, NJ) was placed and a 4F angled tip catheter (Cook Medical, Bloomington, IN) was introduced over a wire into the abdominal aorta. Digital subtraction angiography (shown in FIG. 6B) was performed utilizing approximately 10 cc of Omnipaque 350 contrast media (GE Healthcare, Chicago, IL) to delineate the origin of the celiac artery. Next, a Headway Duo microcatheter (Microvention, Aliso Viejo, CA) was advanced into the hepatic arterial system with subsequent 3-5 cc injections of Omnipaque 350 contrast media performed to delineate supply to the tumor visualized on the previous ultrasound and MRI. The microcatheter was then positioned into the proper hepatic, left hepatic, or right hepatic artery for subsequent injection of $^{89}$Zr labeled iSpheres (YAS microspheres labeled with $^{89}$Zr). After establishing access to the intended delivery location, the catheter was secured in position and the animal was transferred under anesthesia to the PET/CT area.

Figure 5B:
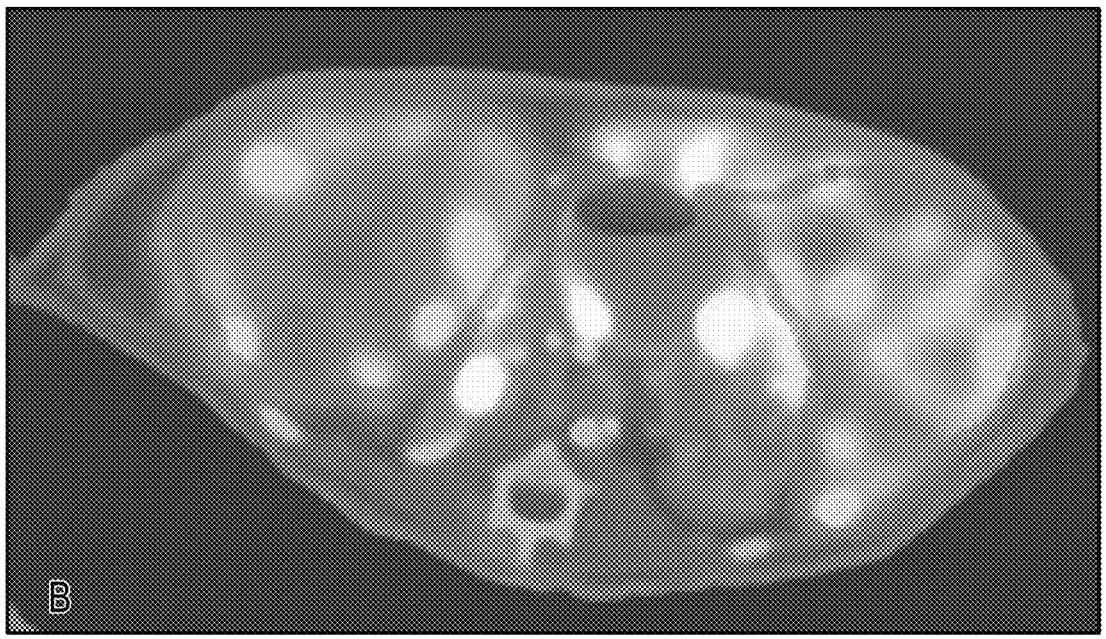

PET/CT imaging was initiated within 5 minutes following microsphere (iSpheres) infusion and followed identical imaging protocols for each animal. Results are shown in FIG. 5B. Two separate injections were performed within the PET/CT area. A customized injection apparatus was utilized for performing injections (Boston Scientific, Marlborough, MA), allowing for the controlled delivery of iSpheres. The first was a "scout dose" injection of up to 1.3 mg of microspheres. Results are shown in FIG. 7A. The second was a dose of up to 13 mg of particles which was designed to model the numbers of particles needed for the therapy procedure (FIGS. 5B and 7B). This second dose was still anticipated to not be significantly embolic in nature, similar to the human imaging procedure. After each injection, 90 minutes of PET/CT imaging was performed (FIG. 5B). Negligible lung uptake is noted, with appreciable differential uptake within tumor vs. normal liver (indicating the patient would be a candidate for SIRT).

A dedicated PET docked with multimodality CT was used for preclinical imaging studies. Starting within 1 h post-injection, dynamic and static scans were acquired. Animals were maintained under anesthesia using isoflurane at 1-5% concentration. CT images were acquired for photon attenuation correction and image co-registration with PET imaging data. The reconstruction algorithms for both PET and CT were provided by the scanner manufacturer. The parameters for CT acquisitions were 120 rotation steps over 220°, continuous acquisition, 80kVp tube voltage, 500 μA tube current, and 175 ms exposure. Image display and analysis were performed using the software package MiM (Cleveland, OH) and Simplicit90Y (Mirada Medical, Denver, CO) (FIGS. 7A and 7B). Volumes of interest (VOIs) were drawn on the co-registered MRI images for tumor, and other organs of interest. VOIs were adjusted to include apparent partial volume spill-outs for organ uptake calculation.

Through this study, it was noted that A) $^{89}$Zr-Spheres can be successfully delivered to the liver in a catheter directed fashion, B) uptake can be successfully visualized utilizing PET-CT, and C) uptake following differential patterns of flow distribution within the liver as suggested by prior, contrast enhanced cross sectional and angiographic imaging.

Example 12: Prophetic Animal Study

Liver tumor bearing animals are used as models for studying diagnostic and therapeutic approaches for managing this condition. Woodchucks with liver tumors from chronic infection with Woodchuck Hepatoma Virus is an example of one such model. After catheterization of the proper hepatic artery of a liver tumor bearing Woodchuck with a microcatheter, imageable radioisotopic microspheres are administered. These distribute in a flow-directed fashion and lodge within the small arteries of the liver. Imageable radioisotopic microspheres are visualized with PET or SPECT and serve as a surrogate for $^{90}$Y-Therasphere, thus allowing the direct mapping of anticipated $^{90}$Y-Therasphere distribution within the liver. This mapping informs choice of a dose that will maximize lethal dose of $^{90}$Y-Therasphere to liver tumor cells while minimizing injury to normal liver cells.

Example 13: Predicting a Dose of Therapeutic Particles Using Surrogates

Based on the inventor's experience, the following prophetic results are projected using controlled studies.

A group of 30 patients suffering from liver cancer are selected for treatment by SIRT with TheraSphere. Prior to treatment, the patients are given a dose of $^{99m}$Tc functionalized yttrium aluminum silicon oxide microspheres (an imageable radioisotopic microsphere as disclosed herein) as a surrogate for $^{90}$Y TheraSphere.

The imageable microspheres have an average diameter of 20-30 m. The dose of the imageable microspheres is dispersed in 0.6 mL pyrogen-free water and is calculated such that approximately 150 MBq is administered. The imageable microspheres are injected into the hepatic artery and allowed to distribute for a period of 15 minutes. At that time, the patients' livers, lungs, and GI tract are imaged using SPECT. From that imaging, the quantity of microspheres reaching each of the liver, the lung, and the GI tract are measured. Patients are categorized for either treatment with TheraSphere or for non-treatment due to risk of lung shunt. Seven patients are eliminated from the treatment category. For the 23 patients that are candidates for treatment, a dose of TheraSphere that will provide 300 Gy to the tumor while maintaining the normal tissue dose <60 Gy based on the proportion of imageable microspheres delivered to the tumor and the normal tissue. For the patients that are candidates for treatment, a dose of TheraSphere that will provide 300 Gy to the liver is calculated based on the proportion of imageable microspheres delivered to the liver. Typically, a target dose of TheraSphere can be anywhere from 80 Gy to 300 Gy. The candidates for treatment are then given a dose of TheraSphere calculated to achieve 300 Gy based on the distribution of imageable radioisotopic microspheres. None of the patients experience lung shunt or significant distribution of damage to the gastrointestinal tract.

For a second group of 30 patients, Tc-99m MAA is administered into the hepatic artery to determine the extent of A-V shunting to the lungs and to confirm the absence of gastric and duodenal flow. At that time, the patients' livers, lungs, and GI tract are imaged. From that imaging, the dose of microspheres reaching each of the liver, the lung, and the GI tract are measured. Patients are categorized for either treatment with TheraSphere or for non-treatment due to risk of lung shunt. Twelve patients are eliminated from the treatment category. The candidates for treatment are then given a dose of TheraSphere calculated to achieve 300 Gy. Four of the patients experience lung shunt and three of the patients have significant distribution of damage to the gastrointestinal tract. Two of the patients receive insufficient treatment based on post treatment evaluation.

The twelve patients removed from the treatment category based on Tc-99m MAA results are administered imageable radioisotopic microspheres as disclosed for the first group. Of these patients, it is found that 8 are actually candidates for treatment with TheraSphere. The candidates for treatment are then given a dose of TheraSphere calculated to achieve 300 Gy based on the distribution of imageable radioisotopic microspheres. None of the patients experience lung shunt or significant distribution of damage to the gastrointestinal tract.

For the third group of 30 patients, a dose of TheraSphere equivalent to 300 Gy to the liver administered. Eight of the patients experience lung shunt and six of the patients have significant distribution of damage to the gastrointestinal tract. Five of the patients receive insufficient treatment based on post treatment evaluation.

What is claimed is:

1. An imageable microsphere, comprising:
   at least one imageable radioisotope; and
   a substrate comprising an inorganic material that comprises metalloid or metal atoms bonded to non-metal atoms, the substrate comprising:
   a core extending to a surface, the core comprising a first portion of the metalloid or metal atoms bonded to the non-metal atoms and the surface comprising a second portion of the metalloid or metal atoms bonded to the nonmetal atoms;
   wherein the at least one imageable radioisotope is bound directly to the substrate through non-metal atoms of the surface of the substrate and/or wherein the at least one imageable radioisotope is bound to the substrate through an inorganic bridge comprising nonmetal atoms of the surface of the substrate;
   wherein the at least one imageable radioisotope is selected from $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr, $^{18}$F, $^{177}$Lu, Al$^{18}$F, and/or combinations thereof; and
   wherein the substrate comprises silicon dioxide and at least one other element selected from manganese, aluminum, gallium, yttrium, boron, strontium, and titanium.

2. The imageable microsphere of claim 1, wherein the at least one imageable radioisotope is bound directly to the substrate through non-metal atoms of the surface of the substrate.

3. The imageable microsphere of claim 1, wherein the at least one imageable radioisotope is bound to the substrate through an inorganic bridge through non-metal atoms of the surface of the substrate.

4. The imageable microsphere of claim 1, wherein the substrate comprises a homogeneous mixture of constituent chemical elements.

5. The imageable microsphere of claim 4, wherein the surface comprises at least a portion of the constituent chemical elements.

6. The imageable microsphere of claim 1, wherein the non-metal atoms are oxygen atoms.

7. The imageable microsphere of claim 6, wherein at least a portion of the oxygen atoms at the surface of the substrate are hydroxyl groups.

8. The imageable microsphere of claim 1, wherein the substrate comprises a metal oxide, a transition metal oxide, a metalloid oxide, or combinations thereof.

9. The imageable microsphere of claim 1, wherein the at least one imageable radioisotope is bound to the substrate via a chemical bond selected from an ionic bond, a covalent bond, or a coordinate bond.

10. The imageable microsphere of claim 9, wherein the at least one imageable radioisotope is bound via a coordinate bond.

11. The imageable microsphere of claim 1, wherein the at least one imageable radioisotope is configured for imaging by an imaging modality selected from single photon imaging and double photon imaging.

12. The imageable microsphere of claim 1, wherein the at least one imageable radioisotope is configured for imaging by an imaging modality selected from positron emission tomography (PET), single photon emission computed tomography (SPECT), and gamma camera imaging.

13. The imageable microsphere of claim 1, wherein the at least one imageable radioisotope is a positron emitter or a gamma emitter.

14. The imageable microsphere of claim 1, wherein the at least one imageable radioisotope is a metallic radioisotope.

15. The imageable microsphere of claim 1, wherein the at least one imageable radioisotope is selected from $^{99m}$Tc and $^{89}$Zr.

16. The imageable microsphere of claim 1 made by a method comprising: providing the substrate; chemically coupling the at least one imageable radioisotope to the substrate to provide the imageable microsphere.

17. A method for determining an amount of therapeutic microspheres to provide to a body of a patient, the method comprising: providing a population of imageable microspheres in accordance with claim 1; delivering the population of imageable microspheres to the patient by introducing the population of imageable microspheres to a first position in a vasculature of the patient; allowing the population of imageable microspheres to distribute within the body of the patient; determining a distribution of at least a portion of the population of the imageable microspheres within the body of the patient by imaging a portion of the body of the patient using an imaging modality; and using the distribution of the imageable microspheres to calculate an amount of therapeutic microspheres to be delivered to the body of the patient.

18. A kit for preparing the imageable microsphere of claim 1, comprising: a microsphere comprising: a substrate comprising an inorganic material that comprises metalloid or metal atoms bonded to non-metal atoms, the substrate comprising: a core extending to a surface, the core comprising a first portion of the metalloid or metal atoms bonded to the non-metal atoms and the surface comprising a second portion of the metalloid or metal atoms bonded to the non-metal atoms; and instructions for reacting an imageable radioisotope with the substrate such as to bind the imageable radioisotope directly to the substrate through at least a portion of the non-metal atoms at the surface of the substrate.

19. The imageable microsphere of claim 1, wherein the substrate comprises yttrium aluminum silicon oxide.

20. The imageable microsphere of claim 19, wherein the at least one imageable radioisotope is selected from $^{99m}$Tc and $^{89}$Zr.

* * * * *